United States Patent [19]

Doetzer et al.

[11] Patent Number: 5,389,619
[45] Date of Patent: Feb. 14, 1995

[54] DERIVATIVES OF PHENYLACETIC ACID, THEIR PREPARATION AND THEIR USE AS PESTICIDES

[75] Inventors: Reinhard Doetzer, Weinheim; Hubert Sauter; Horst Wingert, both of Mannheim; Reinhard Kirstgen, Neustadt; Albrecht Harreus, Ludwigshafen; Gisela Lorenz, Neustadt; Eberhard Ammermann, Heppenheim, all of Germany

[73] Assignee: BASF Aktiengesellschaft, Ludwigshafen, Germany

[21] Appl. No.: 38,862

[22] Filed: Mar. 29, 1993

[30] Foreign Application Priority Data

Apr. 4, 1992 [DE] Germany ............... 4211384

[51] Int. Cl.$^6$ ............... A61K 31/21; A61K 31/235; A61K 31/695; C07C 327/10; C07C 229/28; C07C 229/34

[52] U.S. Cl. .................. 514/63; 514/513; 514/514; 514/530; 514/531; 514/532; 514/533; 514/534; 514/538; 514/539; 514/541; 514/545; 514/520; 514/521; 514/523; 556/414; 556/418; 556/419; 556/420; 558/230; 558/255; 558/389; 558/390; 558/392; 558/393; 558/394; 558/396; 558/398; 560/9; 560/15; 560/16; 560/35; 560/39; 560/45; 560/53; 560/54; 560/60

[58] Field of Search ............... 558/230, 255, 389, 390, 558/392, 393, 394, 396, 398; 556/414, 418, 419, 420; 560/9, 15, 16, 35, 39, 45, 53, 54, 60; 514/63, 513, 514, 530, 531, 532, 533, 534, 538, 539, 541, 545, 520, 521, 523

[56] References Cited

U.S. PATENT DOCUMENTS 4,829,085 5/1989 Wenderoth et al. ............... 514/539
5,147,892 9/1992 Wingert et al. ............... 514/522

FOREIGN PATENT DOCUMENTS 0254426 1/1988 European Pat. Off. .
0354571 2/1990 European Pat. Off. .
0463513 1/1992 European Pat. Off. .
2172595 9/1986 United Kingdom .

*Primary Examiner*—Mary C. Lee
*Assistant Examiner*—Joseph K. McKane
*Attorney, Agent, or Firm*—Oblon, Spivak, McClelland, Maier & Neustadt

[57] ABSTRACT

Compounds of the formula I

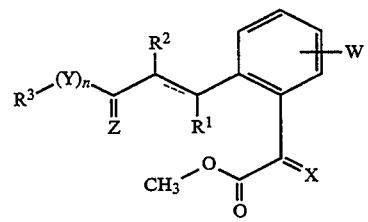

I where n, W, X, Y, Z, $R^1$, $R^2$, and $R^3$ are as defined herein exhibit fungicidal, insecticidal, and acaracidal activity.

26 Claims, No Drawings

DERIVATIVES OF PHENYLACETIC ACID, THEIR PREPARATION AND THEIR USE AS PESTICIDES

The present invention relates to novel phenylacetic acetic acid derivatives having fungicidal, insecticidal and acaricidal activity, fungicides containing these compounds and methods for controlling the fungi.

It is known (for example from European Patents 178,826, 253,213 and 280,185) that esters of acrylic acid, crotonic acid or methoxyiminoacetic acid can be used as fungicides. However, the action of these compounds is unsatisfactory in many cases.

We have found that novel phenylacetic acid derivatives of the general formula I have excellent fungicidal activity and in addition insecticidal and acaricidal activity.

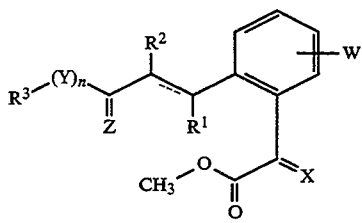

In formula I, n is 0 or 1,

W may occupy any free position on the benzene ring and is hydrogen, halogen, such as fluorine, chlorine, bromine or iodine, unsubstituted or substituted $C_1$–$C_4$-alkyl, such as methyl, ethyl, n-propyl, isopropyl, n-butyl, isobutyl, sec-butyl or tert-butyl, unsubstituted or substituted $C_1$–$C_4$-alkoxy, such as methoxy, ethoxy, n-propoxy, isopropoxy, n-butoxy, isobutoxy, sec-butoxy or tert-butoxy, preferably hydrogen, chlorine, methyl or methoxy, particularly preferably hydrogen, X is $CHOCH_3$, $NOCH_3$, $CHCH_3$ or $CHC_2H_5$, Y is oxygen, sulfur or $NR^4$, —O—$NR^4$, —$NR^4$—O— or $NR^4$—$NR^5$, preferably oxygen, sulfur or $NR^4$, particularly preferably oxygen or $NR^4$, Z is oxygen, $NR^6$, $NOR^7$ or N—$NR^8R^9$ or, if n is 1, furthermore sulfur, preferably oxygen or $NOR^7$ or N—$NR^8R^9$, particularly preferably oxygen or $NOR^7$, $R^1$ is hydrogen or unsubstituted or substituted $C_1$–$C_4$-alkyl as stated above, preferably hydrogen or methyl, particularly preferably hydrogen, $R^2$ is independent of $R^1$ and is hydrogen, unsubstituted or substituted $C_1$–$C_4$-alkyl as stated above, unsubstituted or substituted $C_3$–$C_6$-cycloalkyl, such as cyclopropyl, cyclobutyl, cyclopentyl and cyclohexyl, unsubstituted or substituted and/or fused aryl, such as phenyl, naphthyl, anthryl or phenanthryl, unsubstituted or substituted and/or fused hetaryl, such as 2-pyridyl, 3-pyridyl, 4-pyridyl, 2-quinolyl, 1-isoquinolyl, pyrazinyl, 2-pyrimidinyl, 4-pyrimidinyl, 2-quinoxalinyl, 1-pyrrolyl, 2-pyrrolyl, 3-pyrrolyl, 2-furyl, 3-thienyl, 3-pyrazolyl, 5-pyrazolyl, 1-imidazolyl, 4-imidazolyl, 1,2,4-triazol-3-yl, 2-oxazolyl, 4-oxazolyl, 5-oxazolyl, 3-isoxazolyl, 2-thiazolyl, 4-isothiazolyl, 1,3,4-oxadiazolyl, 1,3,4-thiadiazolyl, 2-indolyl, 3-indolyl, 2-benzothiazolyl, 9-carbazolyl or 2-pteridinyl, $C_1$–$C_4$-perfluoroalkyl, such as trifluoromethyl, pentafluoroethyl, heptafluoroisopropyl or nonafluoro-n-butyl, or CO—V.

$R^2$ is preferably hydrogen, $C_1$–$C_4$-alkyl or CO—V, particularly preferably hydrogen.

$R^3$ is hydrogen, unsubstituted or substituted $C_1$–$C_4$-alkyl as stated above, unsubstituted or substituted $C_2$–$C_4$-alkenyl, such as ethenyl, propen-1-yl, propen-2-yl, propen-3-yl, 2-buten-1-yl or 2-methylpropen-1-yl, unsubstituted or substituted $C_3$–$C_6$-cycloalkyl as stated above, unsubstituted or substituted 3-membered to 6-membered heterocyclyl, such as oxiranyl, azetidinyl, tetrahydrofuran-2-yl, pyrrolidin-1-yl or thiopyran-4-yl, unsubstituted or substituted and/or fused aryl as stated above, unsubstituted or substituted and/or fused hetaryl as stated above, unsubstituted or substituted aryl-$C_1$–$C_4$-alkyl, such as benzyl, 1-phenylethyl, 2-phenylethyl, 4-phenyl-n-butyl, 2-phenyl-2-methylprop-1-yl or naphthylmethyl, unsubstituted or substituted hetaryl-$C_1$–$C_4$-alkyl, such as pyrid-2-ylmethyl, 2-fur-3-ylethyl, 3-isoxazol-5-ylpropyl or 1-indolylmethyl, unsubstituted or substituted aryl-$C_2$–$C_4$-alkenyl, such as 1-phenylethenyl or 1-naphth-3-ylprop-1-en-3-yl, or unsubstituted or substituted hetaryl-$C_2$–$C_4$-alkenyl, such as 2-pyrid-4-ylethenyl or 1-thien-3-ylethenyl, or, if n is 0, furthermore cyano, $C_1$–$C_4$-perfluoroalkyl or unsubstituted or substituted $C_2$–$C_4$-alkynyl, such as ethynyl, propyn-1-yl, propyn-3-yl, 1-butyn-4-yl or 2-butyn-1-yl or, if n is 1 and Y is oxygen, furthermore unsubstituted or substituted trialkylsilyl, such as trimethylsilyl, triethylsilyl, tert-butyldimethylsilyl or di-tert-butylmethylsilyl.

$R^3$ is preferably hydrogen, unsubstituted or substituted $C_1$–$C_4$-alkyl, unsubstituted or substituted and/or fused aryl, unsubstituted or substituted and/or fused hetaryl or unsubstituted or substituted aryl-$C_1$–$C_4$-alkyl, particularly preferably hydrogen, $C_1$–$C_4$-alkyl, unsubstituted or substituted phenyl or unsubstituted or substituted benzyl, $R^4$ and $R^5$ are independent of one another and are each hydrogen, unsubstituted or substituted $C_1$–$C_4$-alkyl as stated above or unsubstituted or substituted $C_3$–$C_6$-cycloalkyl as stated above, preferably hydrogen, methyl or ethyl, $R^6$ is unsubstituted or substituted $C_1$–$C_4$-alkyl as stated above or unsubstituted or substituted and/or fused aryl or hetaryl as stated above, preferably substituted phenyl, $R^7$ and $R^8$ are each hydrogen, unsubstituted or substituted $C_1$–$C_4$-alkyl as stated above, unsubstituted or substituted $C_2$–$C_4$-alkenyl as stated above, unsubstituted or substituted $C_2$–$C_4$-alkynyl as stated above, unsubstituted or substituted $C_3$–$C_6$-cycloalkyl as stated above, unsubstituted or substituted and/or fused aryl as stated above, unsubstituted or substituted and/or fused hetaryl as stated above, unsubstituted or substituted aryl-$C_1$-$C_4$-alkyl as stated above, unsubstituted or substituted hetaryl-$C_1$-$C_4$-alkyl as stated above, or $COR^{10}$.

$R^7$ is preferably hydrogen, unsubstituted or substituted $C_1$-$C_4$-alkyl, unsubstituted or substituted $C_2$-$C_4$-alkenyl, unsubstituted or substituted aryl-$C_1$-$C_4$-alkyl or unsubstituted or substituted hetaryl-$C_1$-$C_4$-alkyl, particularly preferably $C_1$-$C_4$-alkyl or unsubstituted or substituted benzyl, and $R^8$ is preferably hydrogen, unsubstituted or substituted $C_1$-$C_4$-alkyl or unsubstituted or substituted aryl, particularly preferably unsubstituted or substituted phenyl, $R^9$ has the same general and preferred meanings as $R^4$ and is independent of $R^8$, $R^{10}$ is unsubstituted or substituted $C_1$-$C_4$-alkyl as stated above, unsubstituted or substituted $C_3$-$C_6$-cycloalkyl as stated above, unsubstituted or substituted aryl as stated above or unsubstituted or substituted hetaryl as stated above, preferably unsubstituted or substituted $C_1$-$C_4$-alkyl or unsubstituted or substituted aryl, particularly preferably methyl or unsubstituted or substituted phenyl, V is unsubstituted or substituted $C_1$-$C_4$-alkyl as stated above, unsubstituted or substituted aryl as stated above, unsubstituted or substituted hetaryl as stated above, hydroxyl, unsubstituted or substituted $C_1$-$C_4$-alkoxy as stated above, unsubstituted or substituted allyloxy, unsubstituted or substituted benzyloxy or unsubstituted or substituted trimethylsilyloxy.

The bond ⋯⋯ between the two carbon atoms carrying $R^1$ and $R^2$ may be a single or a double bond. The double bond is preferred.

The radicals indicated as being unsubstituted or substituted can carry, in any position, one or more, preferably one to three, substituents, which are identical or different. These substituents are hydrogen, halogen, cyano, nitro, alkyl, alkenyl, alkynyl, cycloalkyl, aryl, heteroaryl, heterocyclyl, haloalkyl, hydroxyl, alkoxy, alkenyloxy, alkynyloxy, cycloalkyloxy, aryloxy, heteroaryloxy, heterocyclyloxy, haloalkoxy, mercapto, alkylthio, alkenylthio, alkynylthio, cycloalkylthio, arylthio, heteroarylthio, heterocyclylthio, haloalkylthio, amino, alkylamino, alkenylamino, alkynylamino, cycloalkylamino, arylamino, heteroarylamino, heterocyclylamino, dialkylamino, N-alkylarylamino, N-alkyl-heteroarylamino, formyl, alkylcarbonyl, alkenylcarbonyl, alkynylcarbonyl, cycloalkylcarbonyl, arylcarbonyl, heteroarylcarbonyl, heterocyclylcarbonyl, carboxyl, alkoxycarbonyl, alkenyloxycarbonyl, alkynyloxycarbonyl, cycloalkyloxycarbonyl, aryloxycarbonyl, heteroaryloxycarbonyl, heterocyclyloxy-carbonyl, formyloxy, alkylcarbonyloxy, alkenylcarbonyloxy, alkynylcarbonyloxy, cycloalkylcarbonyloxy, arylcarbonyloxy, heteroarylcarbonyloxy, heterocyclylcarbonyloxy, aminocarbonyl, alkylaminocarbonyl, alkenylaminocarbonyl, alkynylaminocarbonyl, cycloalkylamino-carbonyl, arylaminocarbonyl, heteroarylaminocarbonyl, heterocyclylaminocarbonyl, dialkylaminocarbonyl, N-alkyl-arylaminocarbonyl, N-alkyl-heteroarylaminocarbonyl, hydroxylaminocarbonyl, alkoxyaminocarbonyl, alkenyloxyaminocarbonyl, alkynyloxyaminocarbonyl, formamido, alkyl-carbonylamino, alkenylcarbonylamino, alkynylcarbonyl-amino, cycloalkylcarbonylamino, arylcarbonylamino, heteroarylcarbonylamino, heterocyclylcarbonylamino, alkylcarbonyl-N-alkylamino, arylcarbonyl-N-alkylamino, heteroarylcarbonyl-N-alkylamino, aminothiocarbonyl, alkylamino-thiocarbonyl, dialkylaminothiocarbonyl, alkylsulfoxyl, arylsulfoxyl, heteroarylsulfoxyl, alkylsulfonyl, aryl-sulfonyl, heteroarylsulfonyl, hydroxysulfinyl, alkoxysulfinyl, hydroxysulfonyl, alkoxysulfonyl, alkylsulfinyloxy, arylsulfinyloxy, heteroarylsulfinyloxy, alkyl-sulfonyloxy, arylsulfonyloxy, heteroaryl sulfonyloxy, dialkoxyphosphinyl, bis(aryloxy)phosphinyl, trialkylsilyl, trialkylsilyloxy, or a fragment of the formula R'—O—N=CR", in which R' and R" independently of one another are hydrogen, alkyl, alkenyl or alkynyl and, is R' is not hydrogen, R" can also be alkoxy.

In the abovementioned substituents, halogen and the organic substructures, for example ethyl, each have the abovementioned meanings. The substituents can in turn be substituted by one or more of the abovementioned radicals.

The novel compounds of the formula I may be obtained in the preparation as mixtures of stereoisomers (E/Z isomers at C=C or C=N double bonds, diastereomers, enantiomers), which can be separated into their individual components in a conventional manner, for example by crystallization or chromatography. Both the individual isomers and the mixtures thereof can be used as fungicides, insecticides or acaricides, and the present invention relates to all of them. The fungicidal activity is preferred.

The present invention preferably relates to novel compounds of the general formula II

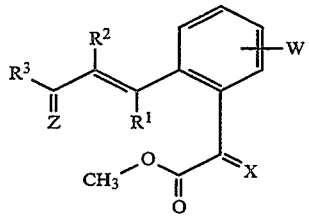

where

W may occupy any free position on the benzene ring and is hydrogen, chlorine, methyl or methoxy, preferably hydrogen, X is $CHOCH_3$, $NOCH_3$, $CHCH_3$ or $CHC_2H_5$, Z is oxygen, $NR^6$, $NOR^7$ or $N-NR^8R^9$, preferably oxygen or $NOR^7$, $R^1$ and $R^2$ are independent of one another and are each hydrogen or $C_1$–$C_4$-alkyl as stated above, preferably hydrogen, $R^3$ is hydrogen, unsubstituted or substituted $C_1$–$C_4$-alkyl, unsubstituted or substituted $C_2$–$C_4$-alkenyl, unsubstituted or substituted $C_2$–$C_4$-alkynyl, unsubstituted or substituted $C_3$–$C_6$-cycloalkyl, unsubstituted or substituted 3-membered to 6-membered heterocyclyl, unsubstituted or substituted and/or fused aryl, unsubstituted or substituted and/or fused hetaryl, unsubstituted or substituted aryl-$C_1$–$C_4$-alkyl, unsubstituted or substituted hetaryl-$C_1$–$C_4$-alkyl, unsubstituted or substituted aryl-$C_2$–$C_4$-alkenyl or unsubstituted or substituted hetaryl-$C_2$–$C_4$-alkenyl, in each case as stated above, preferably hydrogen, unsubstituted or substituted $C_1$–$C_4$-alkyl, unsubstituted or substituted aryl, unsubstituted or substituted hetaryl, particularly preferably $C_1$–$C_4$-alkyl or unsubstituted or substituted phenyl, $R^4$ is hydrogen unsubstituted or substituted $C_1$–$C_4$-alkyl or unsubstituted or substituted $C_3$–$C_6$-cycloalkyl, in each case as stated above, preferably hydrogen, methyl or ethyl, $R^6$ is unsubstituted or substituted $C_1$–$C_4$-alkyl or unsubstituted or substituted and/or fused aryl or hetaryl, in each case as stated above, preferably unsubstituted or substituted phenyl, $R^7$ and $R^8$ are each hydrogen, unsubstituted or substituted $C_1$–$C_4$-alkyl, unsubstituted or substituted $C_2$–$C_4$-alkenyl, unsubstituted or substituted $C_2$–$C_4$-alkynyl, unsubstituted or substituted $C_3$–$C_6$-cycloalkyl, unsubstituted or substituted and/or fused aryl, unsubstituted or substituted and/or fused hetaryl, unsubstituted or substituted aryl-$C_1$–$C_4$-alkyl, unsubstituted or substituted hetaryl-$C_1$–$C_4$-alkyl, in each case as stated above, or $COR^{10}$, $R^7$ preferably being hydrogen, unsubstituted or substituted $C_1$–$C_4$-alkyl, unsubstituted or substituted $C_2$–$C_4$-alkenyl, or unsubstituted or substituted aryl-$C_1$–$C_4$-alkyl, particularly preferably $C_1$–$C_4$-alkyl or unsubstituted or substituted benzyl, and $R^8$ preferably being unsubstituted or substituted $C_1$–$C_4$-alkyl or unsubstituted or substituted aryl-$C_1$–$C_4$-alkyl, particularly preferably $C_1$–$C_4$-alkyl or unsubstituted or substituted benzyl, $R^9$ has the same general and preferred meanings as $R^4$ and is independent of $R^8$ and $R^{10}$ is unsubstituted or substituted $C_1$–$C_4$-alkyl, unsubstituted or substituted $C_3$–$C_6$-cycloalkyl, unsubstituted or substituted aryl or unsubstituted or substituted hetaryl, in each case as stated above, preferably $C_1$–$C_4$-alkyl or unsubstituted or substituted phenyl.

The present invention furthermore preferably relates to novel compounds of the general formula III

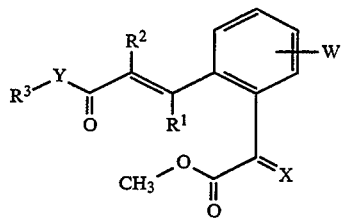

where

W may occupy any free position on the benzene ring and is hydrogen, chlorine, methyl or methoxy, preferably hydrogen, X is $CHOCH_3$, $NOCH_3$, $CHCH_3$ or $CHC_2H_5$, Y is oxygen, sulfur or $NR^4$, preferably oxygen or $NR^4$, $R^1$ is hydrogen or $C_1$–$C_4$-alkyl, preferably hydrogen, $R^2$ is hydrogen, $C_1$–$C_4$-alkyl or CO—V, preferably hydrogen, $R^3$ is hydrogen, unsubstituted or substituted $C_1$–$C_4$-alkyl, unsubstituted or substituted $C_1$–$C_4$-alkenyl, unsubstituted or substituted and/or fused aryl, unsubstituted or substituted and/or fused hetaryl, unsubstituted or substituted aryl-$C_1$–$C_4$-alkyl or unsubstituted or substituted hetaryl-$C_1$–$C_4$-alkyl or, if Y is oxygen, furthermore trialkylsilyl, in each case as stated above, preferably $C_1$–$C_4$-alkyl, unsubstituted or substituted phenyl or unsubstituted or substituted benzyl, $R^4$ is hydrogen, unsubstituted or substituted $C_1$–$C_4$-alkyl or unsubstituted or substituted $C_3$–$C_6$-cycloalkyl, in each case as stated above, preferably hydrogen, methyl or ethyl, and V is hydroxyl, $C_1$–$C_4$-alkoxy, allyloxy, trialkylsilyloxy or unsubstituted or substituted benzyloxy, in each case as stated above.

In one aspect, the present invention particularly preferably relates to novel compounds of the general formula IV

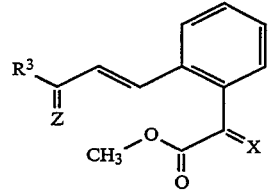

where

X is $CHOCH_3$, $NOCH_3$, $CHCH_3$ or $CHC_2H_5$,

Z is oxygen or $NOR^7$, $R^3$ is hydrogen, unsubstituted or substituted $C_1$–$C_4$-alkyl, unsubstituted or substituted $C_2$–$C_4$-alkenyl, unsubstituted or substituted and/or fused aryl or unsubstituted or substituted and/or fused hetaryl, in each case as stated above, preferably hydrogen, $C_1$–$C_4$-alkyl or unsubstituted or substituted aryl, particularly preferably hydrogen, methyl or unsubstituted or substituted phenyl, $R^7$ is hydrogen, unsubstituted or substituted $C_1$–$C_4$-alkyl, unsubstituted or substituted $C_2$–$C_4$-alkenyl, unsubstituted or substituted aryl-$C_1$–$C_4$-alkyl, preferably unsubstitued or substituted benzyl, unsubstituted or substituted hetaryl-C$_1$-C$_4$-alkyl, preferably methyl substituted by five-membered hetaryl, in each case as stated above, or COR$^{10}$, R$^{10}$ is unsubstituted or substituted C$_1$-C$_4$-alkyl, unsubstituted or substituted aryl or unsubstituted or substituted hetaryl, in each case as stated above, preferably C$_1$-C$_4$-alkyl or unsubstituted or substituted phenyl.

The present invention furthermore particularly pref-

-continued

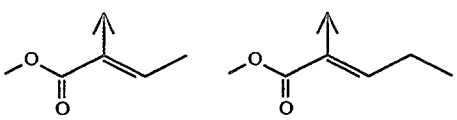

or a fragment from which one of these groups can be synthesized.

Scheme I

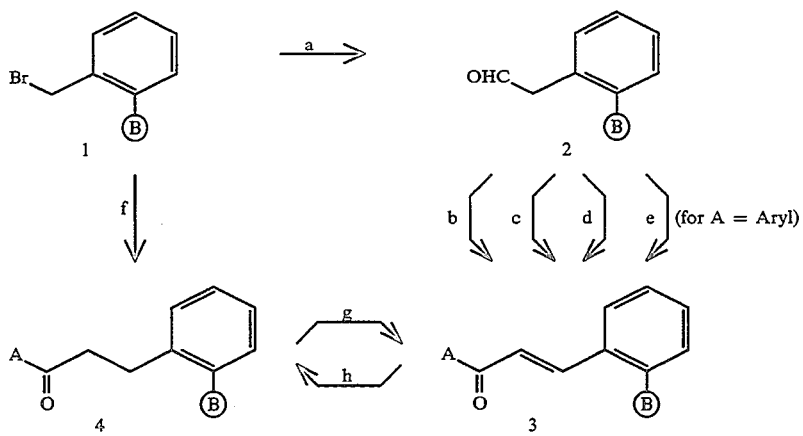

erably relates to novel compounds of the general formula V

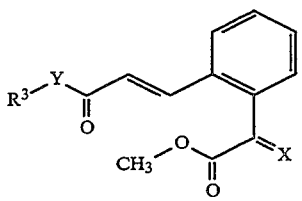

where

X is CHOCH$_3$, NOCH$_3$, CHCH$_3$ or CHC$_2$H$_5$,

Y is oxygen or NR$^4$,

R$^3$ is unsubstituted or substituted C$_1$-C$_4$-alkyl, unsubstituted or substituted and/or fused aryl, unsubstituted or substituted and/or fused hetaryl, unsubstituted or substituted aryl-C$_1$-C$_4$-alkyl or unsubstituted or substituted hetaryl-C$_1$-C$_4$-alkyl, in each case as stated above, and R$^4$ is hydrogen or C$_1$-C$_4$-alkyl, preferably hydrogen, methyl or ethyl.

The novel compounds can be prepared, for example, by the methods shown in the synthesis schemes below. In all schemes, unless restrictions are specifically mentioned, A is an abbreviation for the group R$^3$—(Y)$_n$— defined in claim 1, R is an aliphatic, aromatic or heterocyclic radical and R' may furthermore be hydrogen. B is one of the groups

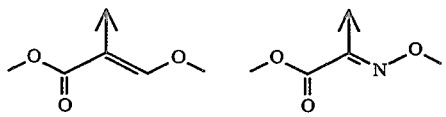

a N-methylmorpholine N-oxide, ΔT b A—COCH$_3$, base or acid, if necessary a dehydrating agent e.g. A—CO—CH$_2$—COOtBu, piperidine/p-TsOH, then CF$_3$COOH, then ΔT d A—CO—CH=PR$_3$ or A—CO—CH$_2$P(=O)Z$_2$ (Z=Ar, O-Alkyl)/base e LiCH$_2$PO(OR)$_2$, A—CN f A—CO—CH$_2$—CO—A, NaOMe g H$_2$, Pd/C h PdCl$_2$(PhCN)$_2$, AgOSO$_2$CF$_3$ or Sn(OSO$_2$CF$_3$)$_2$, N-methylmorpholine ΔT=elevated temperatures, p-TsOH=p-toluenesulfonic acid.

Scheme I shows methods for synthesizing the carbonyl compounds of type 3 or 4 (A=H, alkyl, aryl, hetaryl, organyloxy, organylthio or mono- or diorganylamino). The α,β-unsaturated compounds 3 can advantageously be synthesized from aldehydes 2, which can be achieved by aldol [Org. Synth. Coll. I (1941), 77] or Knoevenagel condensation with subsequent elimination of a carbonyl or carboxyl function [Acta Chem. Scand. 17 (1963), 2316], as well as by Wittig [J. Chem. Soc. (1961), 1266] or Horner-Wadsworth-Emmons olefination [Review Org. React. 25 (1977), 73]. Chalcones (i.e. A=aryl) can also be synthesized in a one-vessel reaction by reacting lithiomethanephosphonic esters with aromatic nitriles and the aldehydes 2 [Synthesis (1991), 213].

The aldehydes of type 2 can be prepared by the method described in European Patent 393,428 from the benzyl bromides 1 [for preparation, see European Patents 226,917, 337,211 and 363,818]. The ketones, esters and 1,3-dicarbonyl compounds required for the condensation reactions are generally known building blocks of organic synthesis; the carbonyl-substituted Wittig and Horner reagents are either known or can be synthesized by methods known from the literature [Ang. Chem. 72

(1960), 572 and 73 (1961), 27; Chem. Ber. 95 (1962), 1513; Org. Synth. Coll. VI (1988), 448].

The saturated carbonyl compounds 4 can be prepared from the benzyl bromides 1 by reaction with β-dicarbonyl compounds with elimination of one of the two carbonyl groups (J. Org. Chem. 30 (1965), 3321]; on the other hand, they can be synthesized from the unsaturated analogs 3, for example by hydrogenation [Org. Synth. Coll. I (1941), 101; J. Am. Chem. Soc.111 (1989), 1063]. Conversely, the preparation of carbonyl-substituted alkenes 3 from the analogous alkanes 4 is also possible [Chem. Lett. (1983), 1207].

The methods denoted by a, b, d, f and g in Scheme I are also suitable for the preparation of the substances which are analogous to the compounds 2, 3 and 4 and in which $R^1$ and $R^2$ (cf. claim 1, 7 or 8) are not hydrogen.

d H$_2$NOR.HCl, ΔT and/or auxiliary base (e.g. pyridine)

e R—Br, base (eg. NaOCH$_3$, K$_2$CO$_3$)

f R—COCl, pyridine

Scheme II shows possibilities for converting the aldehdyes and ketones of type 3a (A=H, organyl) into the N-functional derivatives by standard methods. Thus, imines 5 [Bull. Soc. Chim. Belg. 81 (1972), 643], hydrazones 6 [J. Am. Chem. Soc. 90 (1968), 6821] and oximes [Helv. Chim. Acta 60 (1977), 2294] 7b and oxime ethers 7b [J. Org. Chem. 38 (1973), 3749] are obtainable by condensation of the carbonyl compounds 3a with amines, hydrazines and hydroxylamines or alkoxyamines. For the preparation of the oxime ethers 7b, a two-stage synthesis (conversion of 3a to free oxime 7a, followed by O-alkylation [Helv. Chim. Acta 60 (1977), 2294]) may be advantageous. Oxime esters 7c can like-

Scheme II

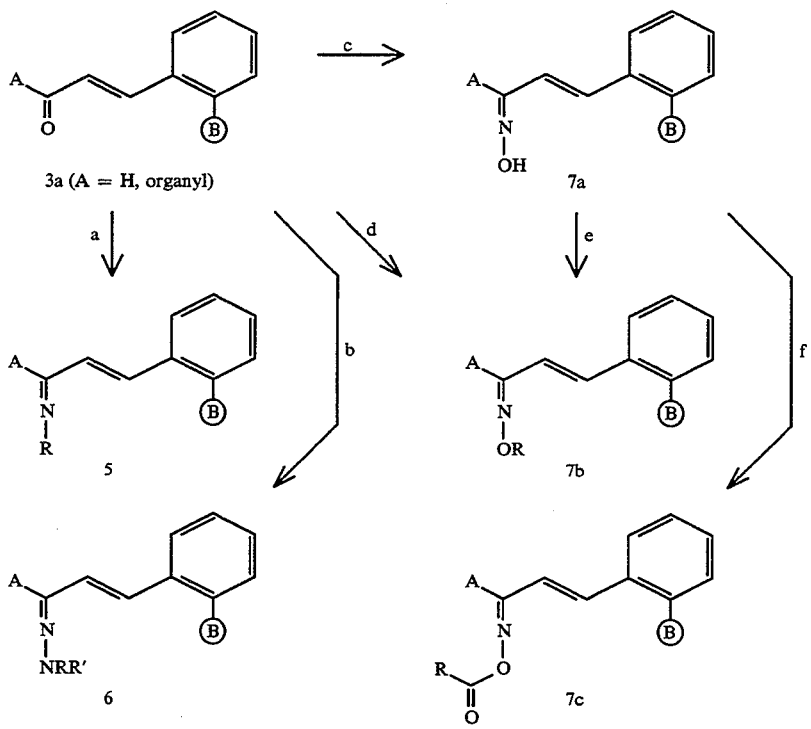

a RNH$_2$, H$^+$, dehydration (azeotropic distillation, molecular sieve)

b RR'N—NH$_2$.HCl or .H$_2$SO$_4$, ΔT c H$_2$NOH.HCl, ΔT and/or wise be obtained from the oximes 7a by reaction with an acyl chloride/pyridine [J. Org. Chem. 33 (1968), 150].

The reactions described in Scheme II are also suitable for the preparation of analogous compounds in which $R^1$ and/or $R^2$ are not H.

Scheme III

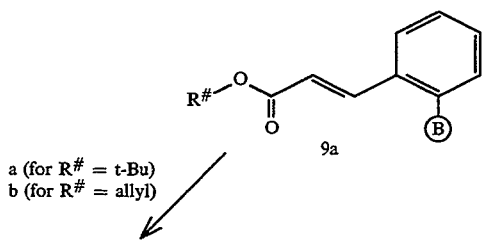

a (for R$^\#$ = t-Bu)
b (for R$^\#$ = allyl)

Scheme III

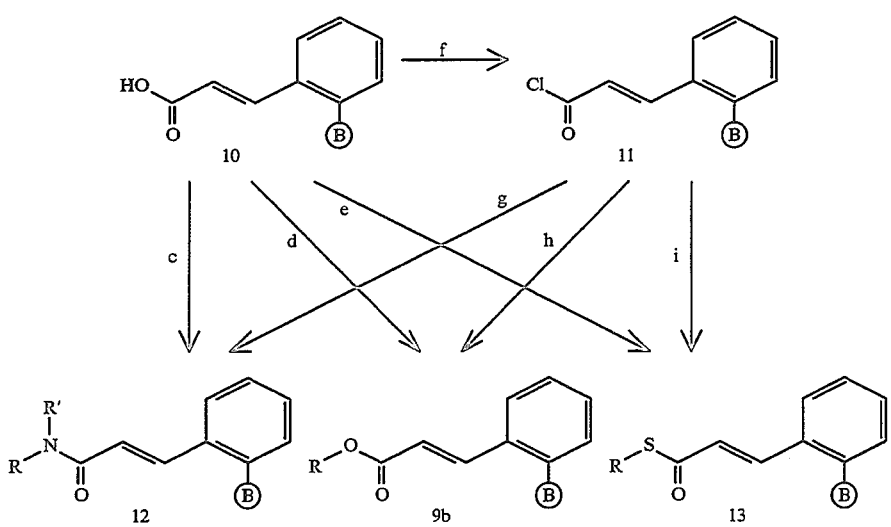

a CF₃COOH, ΔT
b PdCl₂ or Pd(OOCCH₃)₂, PPh₃
c RR'NH, carboxyl-activating agent (eg. di-2-pyridyl disulfide or Ph₂P(=O)Cl)
d R—Br, base (eg. K₂CO₃)
  RSH, carboxyl-activating agent (eg. dicyclohexylcarbodiimide)
f chlorinating agent (eg. SOCl₂), ΔT
g RR'NH; if necessary+pyridine, N(C₂H₅)₃
h ROH, pyridine N(C₂H₅)₃
i RSH, pyridine, N(C₂H₅)₃

The synthesis of cinnamic acid derivatives of type 3 (A=OR, SR, NRR') is illustrated in Scheme III. It is advantageously carried out via carboxylic esters 9a (corresponding to type 3 with A=OR) which can be prepared according to Scheme I and can be hydrolyzed under nonbasic conditions to give the acid 10, for example tert-butyl esters [in acidic medium, J. Am. Chem. Soc. 99 (1977), 2353] or allyl esters [with palladium compounds, Tetrahedron Lett. (1979), 613]. The carboxylic acids 10 can be converted by known methods to, inter alia, mono- or disubstitutedamides 12 [Tetrahedron Lett. (1970), 1901; Synthesis (1980), 385], other esters 9b [European Patent 310,954 and Synthesis (1975), 805] or thioesters 13 [J. Chem. Soc. (C) (1966), 540]. The preparation of such derivatives can also be carried out by the generally known method via the acyl chloride 11 (obtainable by reacting the carboxylic acid 10 with a chlorinating agent, such as thionyl chloride, phosphorus trichloride, phosphoryl chloride or phosgene) by a nucleophilic substitution of the chlorine atom in 11.

The reactions described in Scheme III are also suitable for the preparation of analogous compounds in which R¹ and/or R² are not H.

The reaction routes shown in Schemes II and III are also suitable for converting the saturated carbonyl compounds 4 into the corresponding derivatives. Conversion of the (α,β-unsaturated) products described in the two schemes into their saturated analogs is also possible under suitable hydrogenating or reduction conditions.

Preparation Examples for selected compounds

EXAMPLE 1

Methyl 2-methoximino-2-{2-[3-oxoprop-(E)1-enyl]-phenyl}-acetate (compound No. 77 from Table I)

26.4 g (120 mmol) of methyl 2-methoximino-2-(2-formylphenyl)-acetate (for preparation, see European Patent 393,428, page 3) and 45.6 g of triphenylphosphoranylideneacetaldehyde in 500 ml of toluene are stirred under nitrogen for 20 hours at 60° C. The mixture is cooled and then evaporated down, the residue is taken up in tert-butyl methyl ether/n-hexane, the insoluble substance (triphenylphosphine oxide) is filtered off under suction, the filtrate is evaporated down, diethyl ether is added and the flask is placed in an ice bath. Precipitated Ph₃PO is likewise filtered off under suction, and the filtrate is evaporated down. Column chromatography (from 95:5 to 90:10 cyclohexane/ethyl acetate) gives 23.8 g (80%) of the title compound as yellowish crystals of melting point 90°–94° C. The product is contaminated with about 10% of the vinylog methyl 2-methoximino-2-{2-[5-oxopenta-(E)1,(E)3-dienyl]-phenyl}-acetate.

¹H-NMR (CDCl₃, δ scale): 3.88 and 4.04 (2 s, each 3H, COOCH₃ and NOCH₃); 6.70 (dd, 1H, CH=CH—CHO), 7.1–7.7 (m, together 5H, aromatic protons and CH=CH—CHO); 9.66 (d, 1H, CHO)

EXAMPLE 2

Methyl 2-methoximino-2-{2-[3-(2-chloroprop-2-enyloximino-prop-(E)1-enyl]-phenyl}-acetate (compound No. 57 from Table VI)

3.7 g (15 mmol) of methyl 2-methoximino-2-{2-[3-oxoprop-(E)1-enyl]-phenyl}-acetate (Example 1) and 2.3 g (15mmol) of 2-chloroprop-2-enyloxyamine hydrochloride in 200 ml of tetrahydrofuran (THF) are refluxed for 1 hour. The mixture is allowed to cool, washed twice with saturated sodium chloride solution, dried over magnesium sulfate and evaporated down. Purification by column chromatography (9:1 cyclohexane/ethyl acetate, KG 60) gives the title compound (yellow oil, 2.9 g/58%) as a 4:1 mixture of the anti and syn isomers of the oxime ether.

$^1$H-NMR (CDCl$_3$, δ scale), anti-isomer: 3.88 and 4.04 (2 s, each 3H, COOCH$_3$ and NOCH$_3$); 4.76 (s, 2H, H$_2$C=CCl—CH$_2$O); 5.42 and 5.48 (2 s, each 1H, H$_2$C=CCl); 6.60 and 6.82 (2 d, each 1H, CH=CH—C=N), 7.1–7.8 (m, 4H, aromatic protons); 7.92 (d, 1H, CH=N)

EXAMPLE 3

Methyl 2-{2-[3-oxobut-(E)1-enyl]-phenyl}-3-methoxyprop-(E)2-enoate (compound No. 2 from Table I)

29 g (130 mmol) of methyl (2-formylphenyl)-3-methoxyprop-(E)2-enoate (for preparation, see European Patent 393,428, page 3) and 3.9 g (120 mmol) of triphenylphosphoranylideneacetone in 500 ml of toluene are stirred under nitrogen for 14 hours at 65° C. The mixture is allowed to cool and is evaporated down, the residue is taken up in diethyl ether, the solid (mainly Ph$_3$PO) is filtered off under suction and the solvent is stripped off under reduced pressure. Column chromatography gives the title compound (21.4 g/69%) as a brownish oil, sufficiently pure for further reactions. A crystalline product (mp. 69°–71° C.) is obtained by recrystallization from ether/pentane.

$^1$H-NMR (CDCl$_3$, d scale): 2.32 (s, 3H, CH$_3$—C=O); 3.71 and 3.81 (2 s, each 3H, COOCH$_3$ and CH—OCH$_3$); 6.70 (d, 1H, CH=CH—C=O), 7.2–7.5 (m, together 3H) and 7.72 (d, 1H; aromatic protons); 7.53 (d, 1H, CH=CH—C=O); 7.68 (s, 1H, CH—OCH$_3$)

EXAMPLE 4

Methyl 2-{2-[3-methoximinobut-(E)1-enyl]-phenyl}-3-methoxyprop-(E)2-enoate (compound No. 22 from Table VI)

4.0 g (15 mmol) of methyl 2-{2-[3-oxobut-(E)1-enyl]-phenyl}-3-methoxyprop-(E)2-enoate (Example 3) and 1.3 g (15 mmol) of methoxyamine hydrochloride in 100 ml of methanol are refluxed for 1 hour. The mixture is cooled, after which the methanol is stripped off, the residue is taken up in diethyl ether and the solution is washed with water, dried over magnesium sulfate and evaporated down. The title compound is purified by column chromatography (95:5 cyclohexane/ethyl acetate) and is separated into its C=N double bond isomers (less polar: anti-oxime ether, oil, 1.4 g; more polar: synoxime ether, oil, 0.5 g; together 1.9 g/44%).

(m, together 3H) and 7.67 (d, 1H; aromatic protons); 7.60 (s, 1H, CH—OCH$_3$)

EXAMPLE 5

Methyl 2-methoximino-2-{2-[3-oxobut-(E)1-enyl]-phenyl}-acetate (compound No. 78 from Table I)

50 g (226 mmol) of methyl 2-methoximino-2-(2-formylphenyl)-acetate (European Patent 393,428, page 3) and 72 g (227 mmol) of triphenylphosphoranylideneacetone in 1000 ml of toluene are stirred under nitrogen for 5 hours at 65° C. The mixture is allowed to cool, the solvent is stripped off in a rotary evaporator and the title compound (46.9 g/80%) is obtained as yellowish crystals of melting point 115°–117° C. by recrystallization from isopropanol.

$^1$H-NMR (CDCl$_3$, d scale): 2.35 (s, 3H, CH$_3$—C=O); 3.92 and 4.04 (2 s, each 3H, COOCH$_3$ and NOCH$_3$); 6.69 (d, 1H, CH=CH—C=O); 7.26 (mc, 1H), 7.47 (mc, 2H) and 7.75 (mc, 1H; aromatic protons); 7.31 (d, 1H, CH=CH—C=O)

EXAMPLE 6

Methyl 2-methoximino-2-{2-[3-hydroxyiminobut-(E)1-enyl]-phenyl}-acetate (compound No. 71 from Table VI)

10.4 g (40 mmol) of methyl 2-methoximino-2-{2-[3-oxobut-(E)1-enyl]-phenyl}-acetate (Example 5) and 3.1 g (44 mmol) of hydroxylamine hydrochloride in 200 ml of methanol are refluxed for 1 hour. After cooling, the reaction mixture is evaporated down, the residue is digested in diethyl ether and the solid is filtered off under suction. Column chromatography gives the title compound as separate C=N double bond isomers (less polar: syn-oxime, 2.5 g, colorless crystals, mp. 127°–130° C.; more polar: anti-oxime, 5.0 g, mp. 136°–138° C.; together 7.5 g/68%).

$^1$H-NMR (CDCl$_3$, d scale): syn-isomer, 2.07 (s, 3H, CH$_3$—C=N); 3.98 and 4.06 (2 s, each 3H, COOCH$_3$ and NOCH$_3$); 6.72 (d, 1H, CH=CH—C=N); 7.00 (mc, 1H), 7.3–7.5 (m, 2H) and 7.80 (mc, 1H; aromatic protons), 7.54 (d, 1H, CH=CH—C=N); 8.45 (br, 1H, N—OH)/anti-isomer, 2.08 (s, 3 H, CH$_3$—C=N); 3.90 and 4.05 (2 s, each 3H, COOCH$_3$ and NOCH$_3$); 6.73 (d, 1H, CH=CH—C=N; 7.20 (mc, 1H), 7.43 (mc, 2H) and 7.79 (mc, 1H; aromatic protons), 7.53 (d, 1H, CH=CH—C=N); 8.45 (br, 1H, N—OH)

EXAMPLE 7

Methyl 2-methoximino-2-{2-[3-anti-2,6-difluorobenzyloximinobut-(E)1-enyl]-phenyl}-acetate (compound No. 107 from Table VII)

0.9 g (15.2 mmol) of powdered potassium hydroxide is added to 4.0 g (15.2 mmol) of methyl 2-methoximino-2-{2-[3-anti-hydroximinobut-(E)1-enyl]-phenyl}-acetate (Example 6) in 60 ml of dimethylformamide at +5° C. and a solution of 3.1 g (15.2 mmol) of 2,6-difluorobenzyl bromide in 20 ml of dimethylformamide is added dropwise at this temperature. Stirring is carried out for a further hour at +5° C. and the reaction mixture is poured into ice water, extracted 3 times with diethyl ether, dried over magnesium sulfate and evaporated down. Chromatography (9:1 cyclohexane/ethyl acetate, KG 60) gives the title compound (1.2 g/20%) as colorless crystals of melting point 120°–122° C. $^1$H-NMR (CDCl$_3$, d scale): 1.98 (s, 3H, CH$_3$—C=N); 3.87 and 4.01 (2 s, each 3H, COOCH$_3$ and NOCH$_3$; 5.24 (s, 2H, Ar—CH$_2$—O); 6.60 and 6.80 (2 d, each 1H, CH—CH=C=N); 6.93 (mc, 2H), 7.1–7.5 (m, 6H) and 7.70 (mc, 1H; aromatic protons)

EXAMPLE 8

Methyl 2-methoximino-2-{2-[3-benzyloximinobut-(E)1-enyl]-phenyl}-acetate (compound No. 83 from Table VI)

2.0 g (7.6 mmol) of methyl 2-methoximino-2-{2-[3-oxobut-(E)1-enyl]-phenyl}-acetate (Example 5) and 1.2 g (7.6 mmol) of benzyloxyamine are dissolved in 60 ml of methanol, 1 ml of concentrated hydrochloric acid is added and the reaction mixture is refluxed for 1 hour. It is allowed to cool and is evaporated down, the residue is taken up in diethyl ether, the solution is washed with water and dried over magnesium sulfate and the solvent is stripped off. Column chromatography (from 95:5 to 90:10 cyclohexane/ethyl acetate) gives the title compound as separate C=N double bond isomers (less polar: anti-oxime ether, 1.1 g, oil; more polar: syn-oxime ether, 0.6 g, oil; together 1.7 g/61%).

¹H-NMR (CDCl₃, d scale): anti-isomer: 2.04 (s, 3H, C$\underline{H}_3$—C=N); 3.88 and 4.03 (2 s, each 3H, COOC$\underline{H}_3$ and NOC$\underline{H}_3$); 5.24 (s, 2H, Ar—C$\underline{H}_2$—O); 6.62 and 6.$\overline{82}$ (2 d, each 1H, C$\underline{H}$=CH—C=N); 7.17 (mc, 1H), 7.3–7.5 (m, 7H) and 7.$\overline{69}$ (mc, 1H; aromatic protons)

EXAMPLE 9

Methyl 2-methoximino-2-{2-[3-anti-phenylhydrazonobut-(E)1-enyl]-phenyl}-acetate (compound No. 68 from Table VII)

2.6 g (10 mmol) of methyl 2-methoximino-2-{2-[3-oxobut-(E)1-enyl]-phenyl}-acetate (Example 5) and 1.08 g (10 mmol) of phenylhydrazine in 50 ml of methanol are refluxed for 4 hours. The mixture is allowed to cool, the solvent is stripped off and the product is purified by column chromatography (80:20 cyclohexane/ethyl acetate, KG 60). The anti-hydrazone (oil, 1.5 g/43%) is obtained as the only defined product in the form of yellow crystals from diethyl ether (mp. 155°–158° C.).

¹H-NMR (CDCl₃, d scale): 1.99 (s, 3H, C$\underline{H}_3$—C=N); 3.86 and 4.05 (2 s, each 3H, COOC$\underline{H}_3$ and NOC$\underline{H}_3$); 6.48 (d, 1H, C$\underline{H}$=CH—C=N); 6.86 (t, 1H), 7.1–7.5 (m, 7H) and 7.74 (d, 1$\overline{H}$; aromatic protons); 7.02 (d, 1H, CH=C$\underline{H}$—C=N)

EXAMPLE 10

Methyl 2-methoximino-2-{2-[3-oxo-3-(4-methoxyphenyl)prop-(E)1-enyl]-phenyl}-acetate (compound No. 57 from Table II)

7.7 g (35 mmol) of Methyl 2-methoximino-2-(2-formylphenyl)-acetate (European Patent 393,428, page 3) and 15.5 g (38 mmol) of triphenylphosphoranylidene-4-methoxyacetophenone in 300 ml of toluene are refluxed for 2 hours. The mixture is cooled and then evaporated down and the residue is subjected to column chromatography (from 95:5 to 85:15 cyclohexane/ethyl acetate, KG 60). The title compound (9.7 g/69%) is obtained as virtually colorless crystals (mp. 137°–141° C.).

¹H-NMR (CDCl, d scale): 3.86, 3.91 and 4.10 (3 s, each 3H, COOC$\underline{H}_3$, NOC$\underline{H}_3$ and Ar—OC$\underline{H}_3$); 7.00 and 8.02 (2 d, each 2$\overline{H}$, protons in p-disubstituted aromatics); 7.2–7.9 (m, 6H, protons in o-disubstituted aromatics and C$\underline{H}$=C$\underline{H}$—C=O)

EXAMPLE 11

Methyl 2-methoximino-2-{2-[3-methoximino-3-(4-methoxyphenyl)-prop-(E)1-enyl]-phenyl}-acetate (compound No. 97 from Table VI)

3.5 g (10 mmol) of methyl 2-methoximino-2-{2-[3-oxo-3-(4-methoxyphenyl)-prop-(E)1-enyl]-phenyl}-acetate (Example 10) and 1.0 g (12 mmol) of methoxyamine hydrochloride are refluxed for 2 hours. The mixture is allowed to reach room temperature (20° C., RT) and the methanol is stripped off. Column chromatography (9:1 cyclohexane/ethyl acetate, KG 60) is the title compound (anti/syn isomer mixture, 0.9 g/24%) as a brownish oil which can be crystallized from pentane/diethyl ether (mp. 100°–104° C.).

¹H-NMR (CDCl₃, d scale): 3.80, 3.82, 3.94 and 4.01 (4 s, each 3H, COOC$\underline{H}_3$, both NOC$\underline{H}_3$ and Ar—OC$\underline{H}_3$ in anti-isomer); 3.78, $\overline{3.83}$, 3.90 and $\overline{3.92}$ (4 s, each 3H, COOC$\underline{H}_3$, both NOC$\underline{H}_3$ and Ar—OC$\underline{H}_3$ in syn-isomer); 6.30 (d, 1H, C$\underline{H}$=CH—C=N in syn-isomer); 6.60 (d, 1H, CH=C$\underline{H}$—C=$\overline{N}$ in anti-isomer); 6.85–7.9 (m, 9H, aromatic protons and C$\underline{H}$=CH—C=N in both isomers)

EXAMPLE 12

Methyl 2-methoximino-2-{2-[2-tert-butoxycarbonyl-(E)-ethenyl]-phenyl}-acetate (compound No. 112 from Table I)

17.6 g (80 mmol) of methyl 2-methoximino-2-(2-formylphenyl)-acetate (European Patent 393,428, page 3) and 33 g (88 mmol) of tert-butyl triphenylphosphoranylideneacetate in 500 ml of toluene are stirred under nitrogen for 1 hour at 60° C. The mixture is allowed to cool, the solvent is stripped off, diethyl ether is added to the residue and the mixture is placed in an ice bath. The major amount of triphenylphosphine oxide separates out and is filtered off under suction. The filtrate is evaporated down and the residue is purified by column chromatography (from 95:5 to 93:7 cyclohexane/ethyl acetate). The title compound (24 g/94%) is obtained as a brownish oil.

¹H-NMR (CDCl₃, d scale): 1.53 (s, 9H, (C$\underline{H}_3$)₃CO); 3.85 and 4.03 (2 s, each 3H, COOC$\underline{H}_3$ and NOC$\underline{H}_3$); 6.33 (d, 1H, CH=C$\underline{H}$—C=O); 7.1–$\overline{7.75}$ (m, 5H, aromatic protons and C$\underline{H}$=CH—C=O)

EXAMPLE 13

Methyl 2-methoximino-2-{2-[2-carboxyl-(E)ethenyl]-phenyl}-acetate (compound No. 109 from Table I)

A solution of 18 g (48 mmol) of methyl 2-methoximino-2-{2-[2-tert-butoxycarbonyl-(E)ethenyl]phenyl}-acetate (Example 12) in 100 ml of THF is stirred with 20 ml of concentrated hydrochloric acid for 45 minutes at 65° C. The mixture is allowed to cool, the solvent is stripped off, the remaining crystal slurry is triturated with diisopropyl ether/pentane and the solid is filtered off under suction and dried. The title compound (12 g/81%) is obtained as beige crystals (mp. 178°–182° C.).

¹H-NMR (CDCl₃, d scale): 3.93 and 4.09 (2 s, each 3H, COOC$\underline{H}_3$ and NOC$\underline{H}_3$); 6.48, d, 1H, CH=C$\underline{H}$—C=O); 7.23 (mc, 1$\overline{H}$), 7.50 (mc, 2H) and 7.78 (mc, 1H; aromatic protons); 7.59 (d, 1H, C$\underline{H}$=CH—C=O); 10.8 (broad, 1H, COO$\underline{H}$)

EXAMPLE 14

Methyl 2-methoximino-2-{2-[2-(2,6-difluorobenzyloxy-carbonyl-(E)ethenyl]-phenyl}-acetate (compound No. 37 from Table III)

3.4 g (13 mmol) of methyl 2-methoximino-2-{2-[2-carboxyl-(E)ethenyl]-phenyl}-acetate (Example 13) are dissolved in 50 ml of dimethylformamide, the solution is cooled to +5° C. and 0.75 g (13 mmol) of powdered potassium hydroxide is added. A solution of 2.7 g (13 mmol) of 2,6-difluorobenzyl bromide in 15 ml of dimethylformamide is added dropwise at the same temperature, after which the reaction mixture is allowed to reach room temperature and is stirred for a further hour. The reaction mixture is stirred into ice water and extracted 3 times with diethyl ether and the combined extracts are washed with water, dried and evaporated down. Trituration of the oily residue with diisopropyl ether gives the title compound (3.2 g/63%) in crystalline form (mp. 108°-110° C.).

$^1$H-NMR (CDCl$_3$, d scale): 3.91 and 4.06 (2 s, each 3H, COOC$\underline{H}_3$ and NOC$\underline{H}_3$); 5.31 (s, 2H, Ar—C$\underline{H}_2$—O); 6.42 (d, 1H, CH=C$\underline{H}$—C=O); 6.95 (mc, 2H) and 7.1-7.8 (m, 6H; aromatic protons and C$\underline{H}$=CH—C=O)

EXAMPLE 15

Methyl 2-methoximino-2-{2-[3-oxo-3-phenyl)propyl]-phenyl}-acetate (compound No. 50 from Table X)

5.0 g (17.5 mmol) of methyl 2-methoximino-2-(2-bromomethylphenyl)-acetate (European Patent 363,818, page 3) and 3.9 g (17.5 mmol) of dibenzoylmethane are dissolved in 50 ml of methanol, and 2.7 g (19.3 mmol) of potassium carbonate and a pinch of potassium iodide are added. Stirring is carried out for 90 minutes under reflux, the mixture is allowed to cool and the solvent is stripped off. Water is added to the residue, the latter is extracted twice with methylene chloride and the combined extracts are dried over magnesium sulfate and evaporated down. Flash chromatography (from 90:10 to 75:25 n-hexane/ethyl acetate) gives the title compound (1.4 g/25%) as a deep red oil.

IR (KBr, ~, in cm$^{-1}$): 1722, 1689, 1218, 1205, 1067, 1049, 1015, 957, 748, 689

Examples of compounds preferred because of their action as pesticides are shown in the Tables below.

The double bond C=X in the Tables below has an E (or anti) configuration, unless stated otherwise, and has a double bond between the carbon atoms substituted by R$^1$ and R$^2$ in the general formula I. If only one stereoisomer was isolated in the compounds having a C=N double bond in the side chain (ie. Z=N—R$^6$, N—OR$^7$ or N—NR$^8$R$^9$), or if the isomers were separated, the configuration is specified in a column headed Isomer by the letters a (for anti) and s (for syn). Mixtures of the two forms which have not been separated appear in this column as percentages: a(70) and s(30) means a mixture of 70% of anti-isomer and 30% of syn-isomer.

The chemical shift (solvent CDCl$_3$, standard TMS, δ scale) of protons corresponding to R$^1$ and R$^2$ was used for characterizing compounds obtained in noncrystalline form.

TABLE I

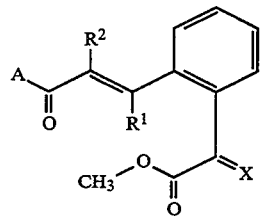

| No. | A | R$^1$ | R$^2$ | X | m.p. (°C.) | δ (C=C$\underline{H}$) |
|---|---|---|---|---|---|---|
| 1 | H | H | H | CHOCH$_3$ | | |
| 2 | CH$_3$ | H | H | CHOCH$_3$ | 69-71 | |
| 3 | C$_2$H$_5$ | H | H | CHOCH$_3$ | | |
| 4 | i-C$_3$H$_7$ | H | H | CHOCH$_3$ | | |
| 5 | n-C$_4$H$_9$ | H | H | CHOCH$_3$ | | |
| 6 | t-C$_4$H$_9$ | H | H | CHOCH$_3$ | oil | 7.07/7.67 |
| 7 | H$_2$C=CH | H | H | CHOCH$_3$ | | |
| 8 | CH$_3$C≡C | H | H | CHOCH$_3$ | | |
| 9 | Cyclopropyl | H | H | CHOCH$_3$ | | |
| 10 | Cyclohexyl | H | H | CHOCH$_3$ | | |
| 11 | N-Methylpiperidin-2-yl | H | H | CHOCH$_3$ | | |
| 12 | C$_6$H$_5$ | H | H | CHOCH$_3$ | oil | |
| 13 | α-Naphthyl | H | H | CHOCH$_3$ | | |
| 14 | β-Naphthyl | H | H | CHOCH$_3$ | | |
| 15 | 2-Pyridyl | H | H | CHOCH$_3$ | | |
| 16 | 3-Pyridyl | H | H | CHOCH$_3$ | | |
| 17 | 4-Pyridyl | H | H | CHOCH$_3$ | | |
| 18 | 6-Chloro-2-pyridyl | H | H | CHOCH$_3$ | | |
| 19 | 2-Pyrazinyl | H | H | CHOCH$_3$ | | |
| 20 | 2-Quinolinyl | H | H | CHOCH$_3$ | | |
| 21 | 2-Furyl | H | H | CHOCH$_3$ | | |
| 22 | 3-Thienyl | H | H | CHOCH$_3$ | | |
| 23 | N-Methyl-3-Pyrryl | H | H | CHOCH$_3$ | | |
| 24 | N-Methyl-2-Indolyl | H | H | CHOCH$_3$ | | |
| 25 | C$_6$H$_5$CH$_2$ | H | H | CHOCH$_3$ | | |
| 26 | β-Naphthylmethyl | H | H | CHOCH$_3$ | | |
| 27 | 2-Pyridylmethyl | H | H | CHOCH$_3$ | | |
| 28 | 2-Furylmethyl | H | H | CHOCH$_3$ | | |
| 29 | 3-Indolylmethyl | H | H | CHOCH$_3$ | | |
| 30 | C$_6$H$_5$CH=CH | H | H | CHOCH$_3$ | | |
| 31 | 2-(2-Furyl)ethenyl | H | H | CHOCH$_3$ | | |
| 32 | CF$_2$ | H | H | CHOCH$_3$ | | |
| 33 | HO | H | H | CHOCH$_3$ | 140-143 | |
| 34 | CH$_3$O | H | H | CHOCH$_3$ | | |
| 35 | C$_2$H$_5$O | H | H | CHOCH$_3$ | | |
| 36 | t-C$_4$H$_9$O | H | H | CHOCH$_3$ | oil | 6.30/7.58 |
| 37 | H$_2$C=CHCH$_2$O | H | H | CHOCH$_3$ | oil | 6.44/7.72 |
| 38 | C$_6$H$_5$O | H | H | CHOCH$_3$ | 103-104 | |

TABLE I-continued

| No. | A | R¹ | R² | X | m.p. (°C.) | δ (C=CH) |
|---|---|---|---|---|---|---|
| 39 | $C_6H_5CH_2O$ | H | H | $CHOCH_3$ | 111–112 | |
| 40 | $(CH_3)_3SiO$ | H | H | $CHOCH_3$ | | |
| 41 | $t-C_4H_9-(CH_3)_2SiO$ | H | H | $CHOCH_3$ | | |
| 42 | $H_2N$ | H | H | $CHOCH_3$ | | |
| 43 | $CH_3NH$ | H | H | $CHOCH_3$ | | |
| 44 | $(CH_3)_2N$ | H | H | $CHOCH_3$ | | |
| 45 | $C_6H_5NH$ | H | H | $CHOCH_3$ | 155 (oil) | |
| 46 | $C_6H_5NCH_3$ | H | H | $CHOCH_3$ | | |
| 47 | $C_6H_5CH_2NH$ | H | H | $CHOCH_3$ | | |
| 48 | $2-CH_3C_6H_4CH_2NH$ | H | H | $CHOCH_3$ | | |
| 49 | $2-ClC_6H_4CH_2NH$ | H | H | $CHOCH_3$ | | |
| 50 | $3-CH_3OC_6H_4CH_2NH$ | H | H | $CHOCH_3$ | | |
| 51 | $4-Cyano-C_6H_4-CH_2NH$ | H | H | $CHOCH_3$ | | |
| 52 | $2,6-F_2-C_6H_3-CH_2NH$ | H | H | $CHOCH_3$ | | |
| 53 | $C_6H_5CH_2NCH_3$ | H | H | $CHOCH_3$ | 122–124 | |
| 54 | $2-CH_3C_6H_4CH_2NCH_3$ | H | H | $CHOCH_3$ | | |
| 55 | $2-ClC_6H_4CH_2NCH_3$ | H | H | $CHOCH_3$ | | |
| 56 | $3-CH_3OC_6H_4CH_2NCH_3$ | H | H | $CHOCH_3$ | | |
| 57 | $4-Cyano-C_6H_4CH_2NCH_3$ | H | H | $CHOCH_3$ | | |
| 58 | N-Morpholinyl | H | H | $CHOCH_3$ | 149–152 | |
| 59 | HS | H | H | $CHOCH_3$ | | |
| 60 | $C_6H_5CH_2S$ | H | H | $CHOCH_3$ | | |
| 61 | $CH_3$ | $CH_3$ | H | $CHOCH_3$ | | |
| 62 | $C_6H_5$ | $CH_3$ | H | $CHOCH_3$ | | |
| 63 | $t-C_4H_9O$ | $CH_3$ | H | $CHOCH_3$ | | |
| 64 | $C_6H_5CH_2O$ | $CH_3$ | H | $CHOCH_3$ | | |
| 65 | $CH_3NH$ | $CH_3$ | H | $CHOCH_3$ | | |
| 66 | $C_6H_5NCH_3$ | $CH_3$ | H | $CHOCH_3$ | | |
| 67 | $C_6H_5CH_2NCH_3$ | $CH_3$ | H | $CHOCH_3$ | | |
| 68 | $C_6H_5CH_2S$ | $CH_3$ | H | $CHOCH_3$ | | |
| 69 | $CH_3$ | H | $CH_3$ | $CHOCH_3$ | 77–79 | |
| 70 | $C_6H_5$ | H | $CH_3$ | $CHOCH_3$ | | |
| 71 | $t-C_4H_9O$ | H | $CH_3$ | $CHOCH_3$ | oil | 7.46 |
| 72 | $C_6H_5CH_2O$ | H | $CH_3$ | $CHOCH_3$ | | |
| 73 | $CH_3NH$ | H | $CH_3$ | $CHOCH_3$ | | |
| 74 | $C_6H_5NCH_3$ | H | $CH_3$ | $CHOCH_3$ | | |
| 75 | $C_6H_5CH_2NCH_3$ | H | $CH_3$ | $CHOCH_3$ | | |
| 76 | $C_6H_5CH_2S$ | H | $CH_3$ | $CHOCH_3$ | | |
| 77 | H | H | H | $NOCH_3$ | 90–94 | |
| 78 | $CH_3$ | H | H | $NOCH_3$ | 115–117 | |
| 79 | $C_2H_5$ | H | H | $NOCH_3$ | | |
| 80 | $i-C_3H_7$ | H | H | $NOCH_3$ | | |
| 81 | $n-C_4H_9$ | H | H | $NOCH_3$ | | |
| 82 | $t-C_4H_9$ | H | H | $NOCH_3$ | 67–69 | |
| 83 | $H_2C=CH$ | H | H | $NOCH_3$ | | |
| 84 | $CH_3C\equiv C$ | H | H | $NOCH_3$ | | |
| 85 | Cyclopropyl | H | H | $NOCH_3$ | | |
| 86 | Cyclohexyl | H | H | $NOCH_3$ | | |
| 87 | N-Methylpiperidin-2-yl | H | H | $NOCH_3$ | | |
| 88 | $C_6H_5$ | H | H | $NOCH_3$ | 98–102 | |
| 89 | α-Naphthyl | H | H | $NOCH_3$ | | |
| 90 | β-Naphthyl | H | H | $NOCH_3$ | | |
| 91 | 2-Pyridyl | H | H | $NOCH_3$ | | |
| 92 | 3-Pyridyl | H | H | $NOCH_3$ | | |
| 93 | 4-Pyridyl | H | H | $NOCH_3$ | | |
| 94 | 6-Chloro-2-pyridyl | H | H | $NOCH_3$ | | |
| 95 | 2-Pyrazinyl | H | H | $NOCH_3$ | | |
| 96 | 2-Quinolinyl | H | H | $NOCH_3$ | | |
| 97 | 2-Furyl | H | H | $NOCH_3$ | | |
| 98 | 3-Thienyl | H | H | $NOCH_3$ | | |
| 99 | N-Methyl-3-Pyrryl | H | H | $NOCH_3$ | | |
| 100 | N-Methyl-2-Indolyl | H | H | $NOCH_3$ | | |
| 101 | $C_6H_5CH_2$ | H | H | $NOCH_3$ | | |
| 102 | β-Naphthylmethyl | H | H | $NOCH_3$ | | |
| 103 | 2-Pyridylmethyl | H | H | $NOCH_3$ | | |
| 104 | 2-Furylmethyl | H | H | $NOCH_3$ | | |
| 105 | 3-Indolylmethyl | H | H | $NOCH_3$ | | |

TABLE I-continued

| No. | A | R¹ | R² | X | m.p. (°C.) | δ (C=CH) |
|---|---|---|---|---|---|---|
| 106 | C₆H₅CH=CH | H | H | NOCH₃ | | |
| 107 | 2-(2-Furyl)ethenyl | H | H | NOCH₃ | | |
| 108 | CF₃ | H | H | NOCH₃ | | |
| 109 | HO | H | H | NOCH₃ | 178–182 | |
| 110 | CH₃O | H | H | NOCH₃ | oil | 6.40/7.10 |
| 111 | C₂H₅O | H | H | NOCH₃ | | |
| 112 | t-C₄H₉O | H | H | NOCH₃ | oil | 6.33/7.39 |
| 113 | H₂C=CHCH₂O | H | H | NOCH₃ | oil | 6.45/7.52 |
| 114 | C₆H₅O | H | H | NOCH₃ | 110 | |
| 115 | C₆H₅CH₂O | H | H | NOCH₃ | oil | 6.49/7.54 |
| 116 | (CH₃)₃SiO | H | H | NOCH₃ | | |
| 117 | t-C₄H₉—(CH₃)₂SiO | H | H | NOCH₃ | | |
| 118 | H₂N | H | H | NOCH₃ | | |
| 119 | CH₃NH | H | H | NOCH₃ | | |
| 120 | (CH₃)₂N | H | H | NOCH₃ | | |
| 121 | C₆H₅NH | H | H | NOCH₃ | 115–117 | |
| 112 | C₆H₅NCH₃ | H | H | NOCH₃ | 136–138 | |
| 123 | C₆H₅CH₂NH | H | H | NOCH₃ | 107–110 | |
| 124 | 2-CH₃C₆H₄CH₂NH | H | H | NOCH₃ | | |
| 125 | 2-ClC₆H₄CH₂NH | H | H | NOCH₃ | | |
| 126 | 3-CH₃OC₆H₄CH₂NH | H | H | NOCH₃ | | |
| 127 | 4-Cyano-C₆H₄—CH₂NH | H | H | NOCH₃ | | |
| 128 | 2,6-F₂—C₆H₃—CH₂NH | H | H | NOCH₃ | | |
| 129 | C₆H₅CH₂NCH₃ | H | H | NOCH₃ | 98–101 | |
| 130 | 2-CH₃C₆H₄CH₂NCH₃ | H | H | NOCH₃ | | |
| 131 | 2-ClC₆H₄CH₂NCH₃ | H | H | NOCH₃ | | |
| 132 | 3-CH₃OC₆H₄CH₂NCH₃ | H | H | NOCH₃ | | |
| 133 | 4-Cyano-C₆H₄CH₂NCH₃ | H | H | NOCH₃ | | |
| 134 | N-Morpholinyl | H | H | NOCH₃ | 132–134 | |
| 135 | HS | H | H | NOCH₃ | | |
| 136 | C₆H₅CH₂S | H | H | NOCH₃ | | |
| 137 | CH₃ | CH₃ | H | NOCH₃ | | |
| 138 | C₆H₅ | CH₃ | H | NOCH₃ | | |
| 139 | t-C₄H₉O | CH₃ | H | NOCH₃ | | |
| 140 | C₆H₅CH₂O | CH₃ | H | NOCH₃ | | |
| 141 | CH₃NH | CH₃ | H | NOCH₃ | | |
| 142 | C₆H₅NCH₃ | CH₃ | H | NOCH₃ | | |
| 143 | C₆H₅CH₂NCH₃ | CH₃ | H | NOCH₃ | | |
| 144 | C₆H₅CH₂S | CH₃ | H | NOCH₃ | | |
| 145 | CH₃ | H | CH₃ | NOCH₃ | oil | 7.33 |
| 146 | C₆H₅ | H | CH₃ | NOCH₃ | | |
| 147 | t-C₄H₉O | H | CH₃ | NOCH₃ | oil | 7.28 |
| 148 | C₆H₅CH₂O | H | CH₃ | NOCH₃ | | |
| 149 | CH₃NH | H | CH₃ | NOCH₃ | | |
| 150 | C₆H₅NCH₃ | H | CH₃ | NOCH₃ | | |
| 151 | C₆H₅CH₂NCH₃ | H | CH₃ | NOCH₃ | | |
| 152 | C₆H₅CH₂S | H | CH₃ | NOCH₃ | | |
| 153 | H | H | H | CHCH₃ | | |
| 154 | CH₃ | H | H | CHCH₃ | | |
| 155 | C₂H₅ | H | H | CHCH₃ | | |
| 156 | i-C₃H₇ | H | H | CHCH₃ | | |
| 157 | n-C₄H₉ | H | H | CHCH₃ | | |
| 158 | t-C₄H₉ | H | H | CHCH₃ | | |
| 159 | H₂C=CH | H | H | CHCH₃ | | |
| 160 | CH₃C≡C | H | H | CHCH₃ | | |
| 161 | Cyclopropyl | H | H | CHCH₃ | | |
| 162 | Cyclohexyl | H | H | CHCH₃ | | |
| 163 | N-Methylpiperidin-2-yl | H | H | CHCH₃ | | |
| 164 | C₆H₅ | H | H | CHCH₃ | | |
| 165 | α-Naphthyl | H | H | CHCH₃ | | |
| 166 | β-Naphthyl | H | H | CHCH₃ | | |
| 167 | 2-Pyridyl | H | H | CHCH₃ | | |
| 168 | 3-Pyridyl | H | H | CHCH₃ | | |
| 169 | 4-Pyridyl | H | H | CHCH₃ | | |
| 170 | 6-Chloro-2-pyridyl | H | H | CHCH₃ | | |
| 171 | 2-Pyrazinyl | H | H | CHCH₃ | | |
| 172 | 2-Quinolinyl | H | H | CHCH₃ | | |
| 173 | 2-Furyl | H | H | CHCH₃ | | |

TABLE I-continued

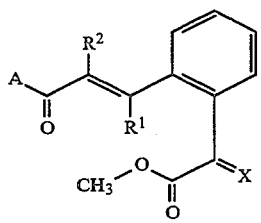

| No. | A | R¹ | R² | X | m.p. (°C.) | δ (C=CH) |
|---|---|---|---|---|---|---|
| 174 | 3-Thienyl | H | H | CHCH$_3$ | | |
| 175 | N-Methyl-3-pyrryl | H | H | CHCH$_3$ | | |
| 176 | N-Methyl-2-indolyl | H | H | CHCH$_3$ | | |
| 177 | C$_6$H$_5$CH$_2$ | H | H | CHCH$_3$ | | |
| 178 | β-Naphthylmethyl | H | H | CHCH$_3$ | | |
| 179 | 2-Pyridylmethyl | H | H | CHCH$_3$ | | |
| 180 | 2-Furylmethyl | H | H | CHCH$_3$ | | |
| 181 | 3-Indolylmethyl | H | H | CHCH$_3$ | | |
| 182 | C$_6$H$_5$CH=CH | H | H | CHCH$_3$ | | |
| 183 | 2-(2-Furyl)ethenyl | H | H | CHCH$_3$ | | |
| 184 | CF$_3$ | H | H | CHCH$_3$ | | |
| 185 | HO | H | H | CHCH$_3$ | | |
| 186 | CH$_3$O | H | H | CHCH$_3$ | | |
| 187 | C$_2$H$_5$O | H | H | CHCH$_3$ | | |
| 188 | t-C$_4$H$_9$O | H | H | CHCH$_3$ | | |
| 189 | H$_2$C=CHCH$_2$O | H | H | CHCH$_3$ | | |
| 190 | C$_6$H$_5$O | H | H | CHCH$_3$ | | |
| 191 | C$_6$H$_5$CH$_2$O | H | H | CHCH$_3$ | | |
| 192 | (CH$_3$)$_3$SiO | H | H | CHCH$_3$ | | |
| 193 | t-C$_4$H$_9$—(CH$_3$)$_2$SiO | H | H | CHCH$_3$ | | |
| 194 | H$_2$N | H | H | CHCH$_3$ | | |
| 195 | CH$_3$NH | H | H | CHCH$_3$ | | |
| 196 | (CH$_3$)$_2$N | H | H | CHCH$_3$ | | |
| 197 | C$_6$H$_5$NH | H | H | CHCH$_3$ | | |
| 198 | C$_6$H$_5$NCH$_3$ | H | H | CHCH$_3$ | | |
| 199 | C$_6$H$_5$CH$_2$NH | H | H | CHCH$_3$ | | |
| 200 | 2-CH$_3$C$_6$H$_4$CH$_2$NH | H | H | CHCH$_3$ | | |
| 201 | 2-ClC$_6$H$_4$CH$_2$NH | H | H | CHCH$_3$ | | |
| 202 | 3-CH$_3$OC$_6$H$_4$CH$_2$NH | H | H | CHCH$_3$ | | |
| 203 | 4-Cyano-C$_6$H$_4$—CH$_2$NH | H | H | CHCH$_3$ | | |
| 204 | 2,6-F$_2$—C$_6$H$_3$—CH$_2$NH | H | H | CHCH$_3$ | | |
| 205 | C$_6$H$_5$CH$_2$NCH$_3$ | H | H | CHCH$_3$ | | |
| 206 | 2-CH$_3$C$_6$H$_4$CH$_2$NCH$_3$ | H | H | CHCH$_3$ | | |
| 207 | 2-ClC$_6$H$_4$CH$_2$NCH$_3$ | H | H | CHCH$_3$ | | |
| 208 | 3-CH$_3$OC$_6$H$_4$CH$_2$NCH$_3$ | H | H | CHCH$_3$ | | |
| 209 | 4-Cyano-C$_6$H$_4$CH$_2$NCH$_3$ | H | H | CHCH$_3$ | | |
| 210 | N-Morpholinyl | H | H | CHCH$_3$ | | |
| 211 | HS | H | H | CHCH$_3$ | | |
| 212 | C$_6$H$_5$CH$_2$S | H | H | CHCH$_3$ | | |
| 213 | CH$_3$ | CH$_3$ | H | CHCH$_3$ | | |
| 214 | C$_6$H$_5$ | CH$_3$ | H | CHCH$_3$ | | |
| 215 | t-C$_4$H$_9$O | CH$_3$ | H | CHCH$_3$ | | |
| 216 | C$_6$H$_5$CH$_2$O | CH$_3$ | H | CHCH$_3$ | | |
| 217 | CH$_3$NH | CH$_3$ | H | CHCH$_3$ | | |
| 218 | C$_6$H$_5$NCH$_3$ | CH$_3$ | H | CHCH$_3$ | | |
| 219 | C$_6$H$_5$CH$_2$NCH$_3$ | CH$_3$ | H | CHCH$_3$ | | |
| 220 | C$_6$H$_5$CH$_2$S | CH$_3$ | H | CHCH$_3$ | | |
| 221 | CH$_3$ | H | CH$_3$ | CHCH$_3$ | | |
| 222 | C$_6$H$_5$ | H | CH$_3$ | CHCH$_3$ | | |
| 223 | t-C$_4$H$_9$O | H | CH$_3$ | CHCH$_3$ | | |
| 224 | C$_6$H$_5$CH$_2$O | H | CH$_3$ | CHCH$_3$ | | |
| 225 | CH$_3$NH | H | CH$_3$ | CHCH$_3$ | | |
| 226 | C$_6$H$_5$NCH$_3$ | H | CH$_3$ | CHCH$_3$ | | |
| 227 | C$_6$H$_5$CH$_2$NCH$_3$ | H | CH$_3$ | CHCH$_3$ | | |
| 228 | C$_6$H$_5$CH$_2$S | H | CH$_3$ | CHCH$_3$ | | |
| 229 | H | H | H | CHC$_2$H$_5$ | | |
| 230 | CH$_3$ | H | H | CHC$_2$H$_5$ | | |
| 231 | C$_2$H$_5$ | H | H | CHC$_2$H$_5$ | | |
| 232 | i-C$_3$H$_7$ | H | H | CHC$_2$H$_5$ | | |
| 233 | n-C$_4$H$_9$ | H | H | CHC$_2$H$_5$ | | |
| 234 | t-C$_4$H$_9$ | H | H | CHC$_2$H$_5$ | | |
| 235 | H$_2$C=CH | H | H | CHC$_2$H$_5$ | | |
| 236 | CH$_3$C≡C | H | H | CHC$_2$H$_5$ | | |
| 237 | Cyclopropyl | H | H | CHC$_2$H$_5$ | | |
| 238 | Cyclohexyl | H | H | CHC$_2$H$_5$ | | |
| 239 | N-Methylpiperidin-2-yl | H | H | CHC$_2$H$_5$ | | |
| 240 | C$_6$H$_5$ | H | H | CHC$_2$H$_5$ | | |
| 241 | α-Naphthyl | H | H | CHC$_2$H$_5$ | | |

TABLE I-continued

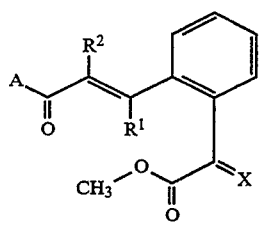

| No. | A | R¹ | R² | X | m.p. (°C.) | δ (C=C$\underline{H}$) |
|---|---|---|---|---|---|---|
| 242 | β-Naphthyl | H | H | CHC$_2$H$_5$ | | |
| 243 | 2-Pyridyl | H | H | CHC$_2$H$_5$ | | |
| 244 | 3-Pyridyl | H | H | CHC$_2$H$_5$ | | |
| 245 | 4-Pyridyl | H | H | CHC$_2$H$_5$ | | |
| 246 | 6-Chloro-2-pyridyl | H | H | CHC$_2$H$_5$ | | |
| 247 | 2-Pyrazinyl | H | H | CHC$_2$H$_5$ | | |
| 248 | 2-Quinolinyl | H | H | CHC$_2$H$_5$ | | |
| 249 | 2-Furyl | H | H | CHC$_2$H$_5$ | | |
| 250 | 3-Thienyl | H | H | CHC$_2$H$_5$ | | |
| 251 | N-Methyl-3-pyrryl | H | H | CHC$_2$H$_5$ | | |
| 252 | N-Methyl-2-indolyl | H | H | CHC$_2$H$_5$ | | |
| 253 | C$_6$H$_5$CH$_2$ | H | H | CHC$_2$H$_5$ | | |
| 254 | β-Naphthylmethyl | H | H | CHC$_2$H$_5$ | | |
| 255 | 2-Pyridylmethyl | H | H | CHC$_2$H$_5$ | | |
| 256 | 2-Furylmethyl | H | H | CHC$_2$H$_5$ | | |
| 257 | 3-Indolylmethyl | H | H | CHC$_2$H$_5$ | | |
| 258 | C$_6$H$_5$CH=CH | H | H | CHC$_2$H$_5$ | | |
| 259 | 2-(2-Furyl)ethenyl | H | H | CHC$_2$H$_5$ | | |
| 260 | CF$_3$ | H | H | CHC$_2$H$_5$ | | |
| 261 | HO | H | H | CHC$_2$H$_5$ | | |
| 262 | CH$_3$O | H | H | CHC$_2$H$_5$ | | |
| 263 | C$_2$H$_5$O | H | H | CHC$_2$H$_5$ | | |
| 264 | t-C$_4$H$_9$O | H | H | CHC$_2$H$_5$ | | |
| 265 | H$_2$C=CHCH$_2$O | H | H | CHC$_2$H$_5$ | | |
| 266 | C$_6$H$_5$O | H | H | CHC$_2$H$_5$ | | |
| 267 | C$_6$H$_5$CH$_2$O | H | H | CHC$_2$H$_5$ | | |
| 268 | (CH$_3$)$_3$SiO | H | H | CHC$_2$H$_5$ | | |
| 269 | t-C$_4$H$_9$—(CH$_3$)$_2$SiO | H | H | CHC$_2$H$_5$ | | |
| 270 | H$_2$N | H | H | CHC$_2$H$_5$ | | |
| 271 | CH$_3$NH | H | H | CHC$_2$H$_5$ | | |
| 272 | (CH$_3$)$_2$N | H | H | CHC$_2$H$_5$ | | |
| 273 | C$_6$H$_5$NH | H | H | CHC$_2$H$_5$ | | |
| 274 | C$_6$H$_5$NCH$_3$ | H | H | CHC$_2$H$_5$ | | |
| 275 | C$_6$H$_5$CH$_2$NH | H | H | CHC$_2$H$_5$ | | |
| 276 | 2-CH$_3$C$_6$H$_4$CH$_2$NH | H | H | CHC$_2$H$_5$ | | |
| 277 | 2-ClC$_6$H$_4$CH$_2$NH | H | H | CHC$_2$H$_5$ | | |
| 278 | 3-CH$_3$OC$_6$H$_4$CH$_2$NH | H | H | CHC$_2$H$_5$ | | |
| 279 | 4-Cyano-C$_6$H$_4$—CH$_2$NH | H | H | CHC$_2$H$_5$ | | |
| 280 | 2,6-F$_2$—C$_6$H$_3$—CH$_2$NH | H | H | CHC$_2$H$_5$ | | |
| 281 | C$_6$H$_5$CH$_2$NCH$_3$ | H | H | CHC$_2$H$_5$ | | |
| 282 | 2-CH$_3$C$_6$H$_4$CH$_2$NCH$_3$ | H | H | CHC$_2$H$_5$ | | |
| 283 | 2-ClC$_6$H$_4$CH$_2$NCH$_3$ | H | H | CHC$_3$H$_5$ | | |
| 284 | 3-CH$_3$OC$_6$H$_4$CH$_2$NCH$_3$ | H | H | CHC$_2$H$_5$ | | |
| 285 | 4-Cyano-C$_6$H$_4$CH$_2$NCH$_3$ | H | H | CHC$_2$H$_5$ | | |
| 286 | N-Morpholinyl | H | H | CHC$_2$H$_5$ | | |
| 287 | HS | H | H | CHC$_2$H$_5$ | | |
| 288 | C$_6$H$_5$CH$_2$S | H | H | CHC$_2$H$_5$ | | |
| 289 | CH$_3$ | CH$_3$ | H | CHC$_2$H$_5$ | | |
| 290 | C$_6$H$_5$ | CH$_3$ | H | CHC$_2$H$_5$ | | |
| 291 | t-C$_4$H$_9$O | CH$_3$ | H | CHC$_2$H$_5$ | | |
| 292 | C$_6$H$_5$CH$_2$O | CH$_3$ | H | CHC$_2$H$_5$ | | |
| 293 | CH$_3$NH | CH$_3$ | H | CHC$_2$H$_5$ | | |
| 294 | C$_6$H$_5$NCH$_3$ | CH$_3$ | H | CHC$_2$H$_5$ | | |
| 295 | C$_6$H$_5$CH$_2$NCH$_3$ | CH$_3$ | H | CHC$_2$H$_5$ | | |
| 296 | C$_6$H$_5$CH$_2$S | CH$_3$ | H | CHC$_2$H$_5$ | | |
| 297 | CH$_3$ | H | CH$_3$ | CHC$_2$H$_5$ | | |
| 298 | C$_6$H$_5$ | H | CH$_3$ | CHC$_2$H$_5$ | | |
| 299 | t-C$_4$H$_9$O | H | CH$_3$ | CHC$_2$H$_5$ | | |
| 300 | C$_6$H$_5$CH$_2$O | H | CH$_3$ | CHC$_2$H$_5$ | | |
| 301 | CH$_3$NH | H | CH$_3$ | CHC$_2$H$_5$ | | |
| 302 | C$_6$H$_5$NCH$_3$ | H | CH$_3$ | CHC$_2$H$_5$ | | |
| 303 | C$_6$H$_5$CH$_2$NCH$_3$ | H | CH$_3$ | CHC$_2$H$_5$ | | |
| 304 | C$_6$H$_5$CH$_2$S | H | CH$_3$ | CHC$_2$H$_5$ | | |
| 305 | 2-CH$_3$—C$_6$H$_4$O— | H | H | CHOCH$_3$ | oil | 6.61/7.89 |
| 306 | 3-CH$_3$—C$_6$H$_4$O— | H | H | CHOCH$_3$ | oil | 6.60/7.87 |
| 307 | 4-CH$_3$—C$_6$H$_4$O— | H | H | CHOCH$_3$ | | |
| 308 | 3-CF$_3$—C$_6$H$_4$O— | H | H | CHOCH$_3$ | oil | 6.60/7.88 |
| 309 | 4-Cl—C$_6$H$_4$O— | H | H | CHOCH$_3$ | | |

TABLE I-continued

| No. | A | R¹ | R² | X | m.p. (°C.) | δ (C=C$\underline{H}$) |
|---|---|---|---|---|---|---|
| 310 | 4-t-C₄H₉—C₆H₄O— | H | H | CHOCH₃ | 106–107 | |
| 311 | 4-CH₃ON=C(CH₃)—C₆H₄O— | H | H | CHOCH₃ | 136–138 | |
| 312 | 3,4-Cl₂—C₆H₃O— | H | H | CHOCH₃ | 88–90 | |
| 313 | 3,5-Cl₂—C₆H₃O— | H | H | CHOCH₃ | 93–95 | |
| 314 | 2-Phenyloxazol-4-yl-methoxy | H | H | CHOCH₃ | oil | 6.48/7.33 |
| 315 | CH₃OOC—CH₂O— | H | H | CHOCH₃ | oil | 6.47/7.78 |
| 316 | t-C₄H₉OOC—CH₂O— | H | H | CHOCH₃ | oil | 6.47/7.76 |
| 317 | t-C₄H₉NH— | H | H | CHOCH₃ | 168–169 | |
| 318 | CH₃OOO—CH(CH₃)NH— | H | H | CHOCH₃ | 130–133 | |
| 319 | CH₃OOC—CH(i-C₄H₉)—NH— | H | H | CHOCH₃ | 142–144 | |
| 320 | Piperidin-1-yl | H | H | CHOCH₃ | 134–135 | |
| 321 | CH₂=C(CH₃)CH₂ONH | H | H | CHOCH₃ | | |
| 322 | CH₂=CCl—CH₂ONH | H | H | CHOCH₃ | | |
| 323 | 3',4'-Cl₂—C₆H₃—CH₂ONH | H | H | CHOCH₃ | 112–114 | |
| 324 | HO— | H | CH₃ | CHOCH₃ | | 7.73 |
| 325 | 2-CH₃—C₆H₄O— | H | CH₃ | CHOCH₃ | | |
| 326 | 3-CF₃—C₆H₄O— | H | CH₃ | CHOCH₃ | | |
| 327 | 4-Cl—C₆H₄O— | H | CH₃ | CHOCH₃ | | |
| 328 | 3,5-Cl₂—C₆H₄O— | H | CH₃ | CHOCH₃ | | |
| 329 | 2-CH₃—C₆H₄O— | H | H | NOCH₃ | oil | 6.63/7.69 |
| 330 | 3-CH₃—C₆H₄O— | H | H | NOCH₃ | 86–87 | |
| 331 | 4-CH₃C₆H₄O— | H | H | NOCH₃ | | |
| 332 | 3-CF₃—C₆H₄O— | H | H | NOCH₃ | 96–98 | |
| 333 | 4-Cl—C₆H₄O— | H | H | NOCH₃ | | |
| 334 | 4-t-C₄H₉—C₆H₄O— | H | H | NOCH₃ | 139–140 | |
| 335 | 4-CH₃ON=C(CH₃)—C₆H₄O— | H | H | NOCH₃ | 79–81 | |
| 336 | 3,4-Cl₂—C₆H₃O— | H | H | NOCH₃ | 136–138 | |
| 337 | 3,5-Cl₂—C₆H₃O— | H | H | NOCH₃ | 115–116 | |
| 338 | 2-Phenyloxazol-4-yl-methoxy | H | H | NOCH₃ | 134–135 | |
| 339 | CH₃OOC—CH₂O— | H | H | NOCH₃ | oil | 6.50/7.77 |
| 340 | t-C₄H₉OOC—CH₂O— | H | H | NOCH₃ | oil | 6.48/7.53 |
| 341 | t-C₄H₉NH— | H | H | NOCH₃ | 199–202 | |
| 342 | CH₃OOO—CH(CH₃)NH— | H | H | NOCH₃ | | |
| 343 | CH₃OOC—CH(i-C₄H₉)—NH— | H | H | NOCH₃ | | |
| 344 | Piperidin-1-yl | H | H | NOCH₃ | 122–124 | |
| 345 | CH₂=C(CH₃)CH₂ONH | H | H | NOCH₃ | 133–136 | |
| 346 | CH₂=CCl—CH₂ONH | H | H | NOCH₃ | | |
| 347 | 3',4'-Cl₂—C₆H₃—CH₂ONH | H | H | NOCH₃ | 119–120 | |
| 348 | HO— | H | CH₃ | NOCH₃ | | |
| 349 | 2-CH₃—C₆H₄O— | H | CH₃ | NOCH₃ | | |
| 350 | 3-CF₃—C₆H₄O— | H | CH₃ | NOCH₃ | | |
| 351 | 4-Cl—C₆H₄O— | H | CH₃ | NOCH₃ | | |
| 352 | 3,5-Cl₂—C₆H₃O— | H | CH₃ | NOCH₃ | | |
| 353 | i-C₃H₇O | H | H | CHOCH₃ | 75–76 | |
| 354 | i-C₃H₇O | H | CH₃ | CHOCH₃ | | |
| 355 | i-C₃H₇O | H | H | NOCH₃ | | |
| 356 | i-C₃H₇O | H | CH₃ | NOCH₃ | | |

TABLE II

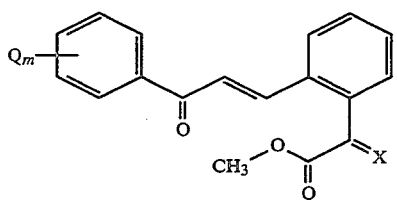

| No. | Q$_m$ | X | m.p. (°C.) | δ (C=C$\underline{H}$) |
|---|---|---|---|---|
| 1 | 3-F | CHOCH₃ | | |
| 2 | 2,6-F₂ | CHOCH₃ | | |

TABLE II-continued

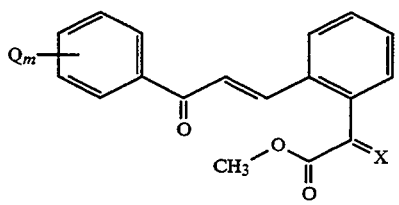

| No. | $Q_m$ | X | m.p. (°C.) | δ (C=CH) |
|---|---|---|---|---|
| 3 | 2-Cl | CHOCH$_3$ | | |
| 4 | 3-Cl | CHOCH$_3$ | | |
| 5 | 4-Cl | CHOCH$_3$ | | |
| 6 | 2,6-Cl$_2$ | CHOCH$_3$ | | |
| 7 | 3,4-Cl$_2$ | CHOCH$_3$ | | |
| 8 | 3-Br | CHOCH$_3$ | | |
| 9 | 4-I | CHOCH$_3$ | | |
| 10 | 2-Cl, 6-F | CHOCH$_3$ | | |
| 11 | 2-CH$_3$ | CHOCH$_3$ | | |
| 12 | 3-CH$_3$ | CHOCH$_3$ | | |
| 13 | 4-CH$_3$ | CHOCH$_3$ | | |
| 14 | 2,4-(CH$_3$)$_2$ | CHOCH$_3$ | | |
| 15 | 2,4,6-(CH$_3$)$_3$ | CHOCH$_3$ | | |
| 16 | 3-C$_2$H$_5$ | CHOCH$_3$ | | |
| 17 | R-t-C$_4$H$_9$ | CHOCH$_3$ | | |
| 18 | 4-Cyclohexyl | CHOCH$_3$ | | |
| 19 | 3-CH$_2$C$_6$H$_5$ | CHOCH$_3$ | | |
| 20 | 2-OCH$_3$ | CHOCH$_3$ | | |
| 21 | 3-OCH$_3$ | CHOCH$_3$ | | |
| 22 | 4-OCH$_3$ | CHOCH$_3$ | Oil | 7.50/ 7.81 |
| 23 | 2-O-i-C$_3$H$_7$ | CHOCH$_3$ | | |
| 24 | 3-OCH$_2$C$_6$H$_5$ | CHOCH$_3$ | | |
| 25 | 3-CF$_3$ | CHOCH$_3$ | | |
| 26 | 3-NO$_2$ | CHOCH$_3$ | | |
| 27 | 4-NO$_2$ | CHOCH$_3$ | | |
| 28 | 3-Cyano | CHOCH$_3$ | | |
| 29 | 2-Cl, 4-CH$_3$ | CHOCH$_3$ | | |
| 30 | 2-COOCH$_3$ | CHOCH$_3$ | | |
| 31 | 4-CH$_2$OCH$_3$ | CHOCH$_3$ | | |
| 32 | 4-COCH$_3$ | CHOCH$_3$ | | |
| 33 | 2-CH$_3$-4-COCH$_3$ | CHOCH$_3$ | | |
| 34 | 4-C(CH$_3$)=NOCH$_2$CH=CH$_2$ | CHOCH$_3$ | | |
| 35 | 2-CH$_3$-4-C(CH$_3$)=NOCH$_2$CH=CH$_2$ | CHOCH$_3$ | | |
| 36 | 3-F | NOCH$_3$ | | |
| 37 | 2,6-F$_2$ | NOCH$_3$ | | |
| 38 | 2-Cl | NOCH$_3$ | | |
| 39 | 3-Cl | NOCH$_3$ | | |
| 40 | 4-Cl | NOCH$_3$ | 104–107 | |
| 41 | 2,6-Cl$_2$ | NOCH$_3$ | | |
| 42 | 3,4-Cl$_2$ | NOCH$_3$ | | |
| 43 | 3-Br | NOCH$_3$ | | |
| 44 | 4-I | NOCH$_3$ | | |
| 45 | 2-Cl, 6-F | NOCH$_3$ | | |
| 46 | 2-CH$_3$ | NOCH$_3$ | | |
| 47 | 3-CH$_3$ | NOCH$_3$ | | |
| 48 | 4-CH$_3$ | NOCH$_3$ | | |
| 49 | 2,4-(CH$_3$)$_2$ | NOCH$_3$ | | |
| 50 | 2,4,6-(CH$_3$)$_3$ | NOCH$_3$ | | |
| 51 | 3-C$_2$H$_5$ | NOCH$_3$ | | |
| 52 | 4-t-C$_4$H$_9$ | NOCH$_3$ | | |
| 53 | 4-Cyclohexyl | NOCH$_3$ | | |
| 54 | 3-CH$_2$C$_6$H$_5$ | NOCH$_3$ | | |
| 55 | 2-OCH$_3$ | NOCH$_3$ | | |
| 56 | 3-OCH$_3$ | NOCH$_3$ | 98–102 | |
| 57 | 4-OCH$_3$ | NOCH$_3$ | 137–141 | |
| 58 | 2-O-i-C$_3$H$_7$ | NOCH$_3$ | | |
| 59 | 3-OCH$_2$C$_6$H$_5$ | NOCH$_3$ | | |
| 60 | 3-CF$_3$ | NOCH$_3$ | | |
| 61 | 3-NO$_2$ | NOCH$_3$ | | |
| 62 | 4-NO$_2$ | NOCH$_3$ | | |
| 63 | 3-Cyano | NOCH$_3$ | | |
| 64 | 2-Cl, 4-CH$_3$ | NOCH$_3$ | | |
| 65 | 2-COOCH$_3$ | NOCH$_3$ | | |
| 66 | 4-CH$_2$OCH$_3$ | NOCH$_3$ | | |
| 67 | 4-COCH$_3$ | NOCH$_3$ | | |
| 68 | 2-CH$_3$-4-COCH$_3$ | NOCH$_3$ | | |
| 69 | 4-C(CH$_3$)=NOCH$_2$CH=CH$_2$ | NOCH$_3$ | | |
| 70 | 2-CH$_3$-4-C(CH$_3$)=NOCH$_2$CH=CH$_2$ | NOCH$_3$ | | |

TABLE II-continued

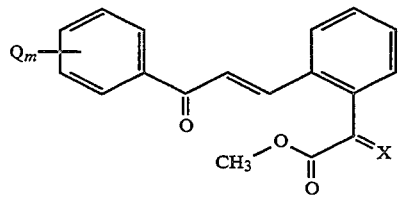

| No. | $Q_m$ | X | m.p. (°C.) | δ (C=CH) |
|---|---|---|---|---|
| 71 | 3-F | CHCH$_3$ | | |
| 72 | 2,6-F$_2$ | CHCH$_3$ | | |
| 73 | 2-Cl | CHCH$_3$ | | |
| 74 | 3-Cl | CHCH$_3$ | | |
| 75 | 4-Cl | CHCH$_3$ | | |
| 76 | 2,6-Cl$_2$ | CHCH$_3$ | | |
| 77 | 3,4-Cl$_2$ | CHCH$_3$ | | |
| 78 | 3-Br | CHCH$_3$ | | |
| 79 | R-I | CHCH$_3$ | | |
| 80 | 2-Cl, 6-F | CHCH$_3$ | | |
| 81 | 2-CH$_3$ | CHCH$_3$ | | |
| 82 | 3-CH$_3$ | CHCH$_3$ | | |
| 83 | 4-CH$_3$ | CHCH$_3$ | | |
| 84 | 2,4-(CH$_3$)$_2$ | CHCH$_3$ | | |
| 85 | 2,4,6-(CH$_3$)$_3$ | CHCH$_3$ | | |
| 86 | 3-C$_2$H$_5$ | CHCH$_3$ | | |
| 87 | 4-t-C$_4$H$_9$ | CHCH$_3$ | | |
| 88 | 4-Cyclohexyl | CHCH$_3$ | | |
| 89 | 3-CH$_2$C$_6$H$_5$ | CHCH$_3$ | | |
| 90 | 2-OCH$_3$ | CHCH$_3$ | | |
| 91 | 3-OCH$_3$ | CHCH$_3$ | | |
| 92 | 4-OCH$_3$ | CHCH$_3$ | | |
| 93 | 2-O-i-C$_3$H$_7$ | CHCH$_3$ | | |
| 94 | 3-OCH$_2$C$_6$H$_5$ | CHCH$_3$ | | |
| 95 | 3-CF$_3$ | CHCH$_3$ | | |
| 96 | 3-NO$_2$ | CHCH$_3$ | | |
| 97 | 4-NO$_2$ | CHCH$_3$ | | |
| 98 | 3-Cyano | CHCH$_3$ | | |
| 99 | 2-Cl, 4-CH$_3$ | CHCH$_3$ | | |
| 100 | 2-COOCH$_3$ | CHCH$_3$ | | |
| 101 | 4-CH$_2$OCH$_3$ | CHCH$_3$ | | |
| 102 | 4-COCH$_3$ | CHCH$_3$ | | |
| 103 | 2-CH$_3$-4-COCH$_3$ | CHCH$_3$ | | |
| 104 | 4-C(CH$_3$)=NOCH$_2$CH=CH$_2$ | CHCH$_3$ | | |
| 105 | 2-CH$_3$-4-C(CH$_3$)=NOCH$_2$CH=CH$_2$ | CHCH$_3$ | | |
| 106 | 3-F | CHC$_2$H$_5$ | | |
| 107 | 2,6-F$_2$ | CHC$_2$H$_5$ | | |
| 108 | 2-Cl | CHC$_2$H$_5$ | | |
| 109 | 3-Cl | CHC$_2$H$_5$ | | |
| 110 | 4-Cl | CHC$_2$H$_5$ | | |
| 111 | 2,6-Cl$_2$ | CHC$_2$H$_5$ | | |
| 112 | 3,4-Cl$_2$ | CHC$_2$H$_5$ | | |
| 113 | 3-Br | CHC$_2$H$_5$ | | |
| 114 | 4-I | CHC$_2$H$_5$ | | |
| 115 | 2-Cl, 6-F | CHC$_2$H$_5$ | | |
| 116 | 2-CH$_3$ | CHC$_2$H$_5$ | | |
| 117 | 3-CH$_3$ | CHC$_2$H$_5$ | | |
| 118 | 4-CH$_3$ | CHC$_2$H$_5$ | | |
| 119 | 2,4-(CH$_3$)$_2$ | CHC$_2$H$_5$ | | |
| 120 | 2,4,6-(CH$_3$)$_3$ | CHC$_2$H$_5$ | | |
| 121 | 3-C$_2$H$_5$ | CHC$_2$H$_5$ | | |
| 122 | 4-t-C$_4$H$_9$ | CHC$_2$H$_5$ | | |
| 123 | 4-Cyclohexyl | CHC$_2$H$_5$ | | |
| 124 | 3-CH$_2$C$_6$H$_5$ | CHC$_2$H$_5$ | | |
| 125 | 2-OCH$_3$ | CHC$_2$H$_5$ | | |
| 126 | 3-OCH$_3$ | CHC$_2$H$_5$ | | |
| 127 | 4-OCH$_3$ | CHC$_2$H$_5$ | | |
| 128 | 2-O-i-C$_3$H$_7$ | CHC$_2$H$_5$ | | |
| 129 | 3-OCH$_2$C$_6$H$_5$ | CHC$_2$H$_5$ | | |
| 130 | 3-CF$_3$ | CHC$_2$H$_5$ | | |
| 131 | 3-NO$_2$ | CHC$_2$H$_5$ | | |
| 132 | 4-NO$_2$ | CHC$_2$H$_5$ | | |
| 133 | 3-Cyano | CHC$_2$H$_5$ | | |
| 134 | 2-Cl, 4-CH$_3$ | CHC$_2$H$_5$ | | |
| 135 | 2-COOCH$_3$ | CHC$_2$H$_5$ | | |
| 136 | 4-CH$_2$OCH$_3$ | CHC$_2$H$_5$ | | |
| 137 | 4-COCH$_3$ | CHC$_2$H$_5$ | | |
| 138 | 2-CH$_3$-4-COCH$_3$ | CHC$_2$H$_5$ | | |
| 139 | 4-C(CH$_3$)=NOCH$_2$CH=CH$_2$ | CHC$_2$H$_5$ | | |

TABLE II-continued

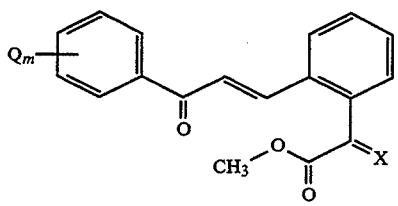

| No. | $Q_m$ | X | m.p. (°C.) | δ (C=CH) |
|---|---|---|---|---|
| 140 | 2-CH₃-4-C(CH₃)=NOCH₂CH=CH₂ | CHC₂H₅ | | |

TABLE III

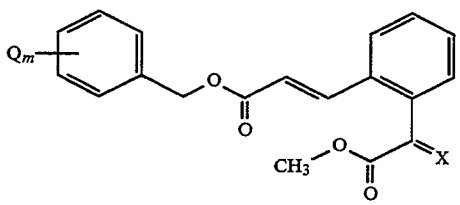

| No. | $Q_m$ | X | m.p. (°C.) | δ (C=CH) |
|---|---|---|---|---|
| 1 | 3-F | CHOCH₃ | | |
| 2 | 2,6-F₂₉ | CHOCH₃ | 114–116 | |
| 3 | 2-Cl | CHOCH₃ | | |
| 4 | 3-Cl | CHOCH₃ | | |
| 5 | 4-Cl | CHOCH₃ | | |
| 6 | 2,6-Cl₂ | CHOCH₃ | | |
| 7 | 3,4-Cl₂ | CHOCH₃ | | |
| 8 | 3-Br | CHOCH₃ | | |
| 9 | 4-I | CHOCH₃ | | |
| 10 | 2-Cl, 6-F | CHOCH₃ | | |
| 11 | 2-CH₃ | CHOCH₃ | 110–112 | |
| 12 | 3-CH₃ | CHOCH₃ | oil | 6.44/ 6.73 |
| 13 | 4-CH₃ | CHOCH₃ | | |
| 14 | 2,4-(CH₃)₂ | CHOCH₃ | | |
| 15 | 2,4,6-(CH₃)₃ | CHOCH₃ | | |
| 16 | 3-C₂H₅ | CHOCH₃ | | |
| 17 | 4-t-C₄H₉ | CHOCH₃ | | |
| 18 | 4-Cyclohexyl | CHOCH₃ | | |
| 19 | 3-CH₂C₆H₅ | CHOCH₃ | | |
| 20 | 2-OCH₃ | CHOCH₃ | | |
| 21 | 3-OCH₃ | CHOCH₃ | | |
| 22 | 4-OCH₃ | CHOCH₃ | | |
| 23 | 2-O-i-C₃H₇ | CHOCH₃ | | |
| 24 | 3-OCH₂C₆H₅ | CHOCH₃ | | |
| 25 | 3-CF₃ | CHOCH₃ | | |
| 26 | 3-NO₂ | CHOCH₃ | | |
| 27 | 2-Cyano | CHOCH₃ | 141–142 | |
| 28 | 3-Cyano | CHOCH₃ | 93–94 | |
| 29 | 2-Cl, 4-CH₃ | CHOCH₃ | | |
| 30 | 2-COOCH₃ | CHOCH₃ | | |
| 31 | 4-CH₂OCH₃ | CHOCH₃ | | |
| 32 | 4-COCH₃ | CHOCH₃ | | |
| 33 | 2-CH₃-4-COCH₃ | CHOCH₃ | | |
| 34 | 4-C(CH₃)=NOCH₂CH=CH₂ | CHOCH₃ | | |
| 35 | 2-CH₃-4-C(CH₃)=NOCH₂CH=CH₂ | CHOCH₃ | | |
| 36 | 3-F | NOCH₃ | | |
| 37 | 2,6-F₂ | NOCH₃ | 108–110 | |
| 38 | 2-Cl | NOCH₃ | | |
| 39 | 3-Cl | NOCH₃ | | |
| 40 | 4-Cl | NOCH₃ | | |
| 41 | 2,6-Cl₂ | NOCH₃ | | |
| 42 | 3,4-Cl₂ | NOCH₃ | | |
| 43 | 3-Br | NOCH₃ | | |
| 44 | 4-I | NOCH₃ | | |
| 45 | 2-Cl, 6-F | NOCH₃ | | |
| 46 | 2-CH₃ | NOCH₃ | 91–94 | |
| 47 | 3-CH₃ | NOCH₃ | oil | 6.45/ 7.51 |
| 48 | 4-CH₃ | NOCH₃ | | |
| 49 | 2,4-(CH₃)₂ | NOCH₃ | | |

TABLE III-continued

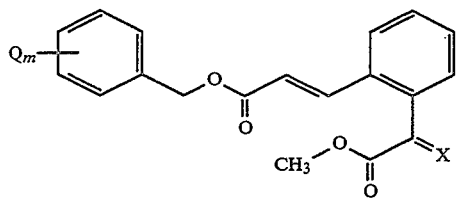

| No. | $Q_m$ | X | m.p. (°C.) | δ (C=C$\underline{H}$) |
|---|---|---|---|---|
| 50 | 2,4,6-(CH$_3$)$_3$ | NOCH$_3$ | | |
| 51 | 3-C$_2$H$_5$ | NOCH$_3$ | | |
| 52 | 4-t-C$_4$H$_9$ | NOCH$_3$ | | |
| 53 | 4-Cyclohexyl | NOCH$_3$ | | |
| 54 | 3-CH$_2$C$_6$H$_5$ | NOCH$_3$ | | |
| 55 | 2-OCH$_3$ | NOCH$_3$ | 87–88 | |
| 56 | 3-OCH$_3$ | NOCH$_3$ | | |
| 57 | 4-OCH$_3$ | NOCH$_3$ | | |
| 58 | 2-O-i-C$_3$H$_7$ | NOCH$_3$ | | |
| 59 | 3-OCH$_2$C$_6$H$_5$ | NOCH$_3$ | | |
| 60 | 3-CF$_3$ | NOCH$_3$ | | |
| 61 | 3-NO$_2$ | NOCH$_3$ | | |
| 62 | 2-Cyano | NOCH$_3$ | 127–129 | |
| 63 | 3-Cyano | NOCH$_3$ | 104–106 | |
| 64 | 2-Cl, 4-CH$_3$ | NOCH$_3$ | | |
| 65 | 2-COOCH$_3$ | NOCH$_3$ | | |
| 66 | 4-CH$_2$OCH$_3$ | NOCH$_3$ | | |
| 67 | 4-COCH$_3$ | NOCH$_3$ | | |
| 68 | 2-CH$_3$-4-COCH$_3$ | NOCH$_3$ | | |
| 69 | 4-C(CH$_3$)=NOCH$_2$CH=CH$_2$ | NOCH$_3$ | | |
| 70 | 2-CH$_3$-4-C(CH$_3$)=NOCH$_2$CH=CH$_2$ | NOCH$_3$ | | |
| 71 | 3-F | CHCH$_3$ | | |
| 72 | 2,6-F$_2$ | CHCH$_3$ | | |
| 73 | 2-Cl | CHCH$_3$ | | |
| 74 | 3-Cl | CHCH$_3$ | | |
| 75 | 4-Cl | CHCH$_3$ | | |
| 76 | 2,6-Cl$_2$ | CHCH$_3$ | | |
| 77 | 3,4-Cl$_2$ | CHCH$_3$ | | |
| 78 | 3-Br | CHCH$_3$ | | |
| 79 | 4-I | CHCH$_3$ | | |
| 80 | 2-Cl, 6-F | CHCH$_3$ | | |
| 81 | 2-CH$_3$ | CHCH$_3$ | | |
| 82 | 3-CH$_3$ | CHCH$_3$ | | |
| 83 | 4-CH$_3$ | CHCH$_3$ | | |
| 84 | 2,4-(CH$_3$)$_2$ | CHCH$_3$ | | |
| 85 | 2,4,6-(CH$_3$)$_3$ | CHCH$_3$ | | |
| 86 | 3-C$_2$H$_5$ | CHCH$_3$ | | |
| 87 | 4-t-C$_4$H$_9$ | CHCH$_3$ | | |
| 88 | 4-Cyclohexyl | CHCH$_3$ | | |
| 89 | 3-CH$_2$C$_6$H$_5$ | CHCH$_3$ | | |
| 90 | 2-OCH$_3$ | CHCH$_3$ | | |
| 91 | 3-OCH$_3$ | CHCH$_3$ | | |
| 92 | 4-OCH$_3$ | CHCH$_3$ | | |
| 93 | 2-O-i-C$_3$H$_7$ | CHCH$_3$ | | |
| 94 | 3-OCH$_2$C$_6$H$_5$ | CHCH$_3$ | | |
| 95 | 3-CF$_3$ | CHCH$_3$ | | |
| 96 | 3-NO$_2$ | CHCH$_3$ | | |
| 97 | 2-Cyano | CHCH$_3$ | | |
| 98 | 3-Cyano | CHCH$_3$ | | |
| 99 | 2-Cl, 4-CH$_3$ | CHCH$_3$ | | |
| 100 | 2-COOCH$_3$ | CHCH$_3$ | | |
| 101 | 4-CH$_2$OCH$_3$ | CHCH$_3$ | | |
| 102 | 4-COCH$_3$ | CHCH$_3$ | | |
| 103 | 2-CH$_3$-4-COCH$_3$ | CHCH$_3$ | | |
| 104 | 4-C(CH$_3$)=NOCH$_2$CH=CH$_2$ | CHCH$_3$ | | |
| 105 | 2-CH$_3$-4-C(CH$_3$)=NOCH$_2$CH=CH$_2$ | CHCH$_3$ | | |
| 106 | 3-F | CHC$_2$H$_5$ | | |
| 107 | 2,6-F$_2$ | CHC$_2$H$_5$ | | |
| 108 | 2-Cl | CHC$_2$H$_5$ | | |
| 109 | 3-Cl | CHC$_2$H$_5$ | | |
| 110 | 4-Cl | CHC$_2$H$_5$ | | |
| 111 | 2,6-Cl$_2$ | CHC$_2$H$_5$ | | |
| 112 | 3,4-Cl$_2$ | CHC$_2$H$_5$ | | |
| 113 | 3-Br | CHC$_2$H$_5$ | | |
| 114 | 4-I | CHC$_2$H$_5$ | | |
| 115 | 2-Cl, 6-F | CHC$_2$H$_5$ | | |
| 116 | 2-CH$_3$ | CHC$_2$H$_5$ | | |
| 117 | 3-CH$_3$ | CHC$_2$H$_5$ | | |
| 118 | 4-CH$_3$ | CHC$_2$H$_5$ | | |

TABLE III-continued

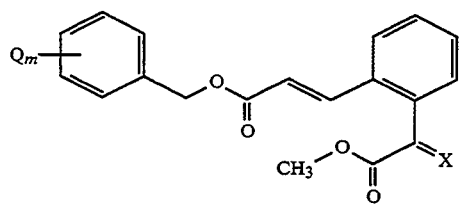

| No. | $Q_m$ | X | m.p. (°C.) | δ (C=C$\underline{H}$) |
|---|---|---|---|---|
| 119 | 2,4-$(CH_3)_2$ | $CHC_2H_5$ | | |
| 120 | 2,4,6-$(CH_3)_3$ | $CHC_2H_5$ | | |
| 121 | 3-$C_2H_5$ | $CHC_2H_5$ | | |
| 122 | 4-t-$C_4H_9$ | $CHC_2H_5$ | | |
| 123 | 4-Cyclohexyl | $CHC_2H_5$ | | |
| 124 | 3-$CH_2C_6H_5$ | $CHC_2H_5$ | | |
| 125 | 2-$OCH_3$ | $CHC_2H_5$ | | |
| 126 | 3-$OCH_3$ | $CHC_2H_5$ | | |
| 127 | 4-$OCH_3$ | $CHC_2H_5$ | | |
| 128 | 2-O-i-$C_3H_7$ | $CHC_2H_5$ | | |
| 129 | 3-$OCH_2C_6H_5$ | $CHC_2H_5$ | | |
| 130 | 3-$CF_3$ | $CHC_2H_5$ | | |
| 131 | 3-$NO_2$ | $CHC_2H_5$ | | |
| 132 | 2-Cyano | $CHC_2H_5$ | | |
| 133 | 3-Cyano | $CHC_2H_5$ | | |
| 134 | 2-Cl, 4-$CH_3$ | $CHC_2H_5$ | | |
| 135 | 2-$COOCH_3$ | $CHC_2H_5$ | | |
| 136 | 4-$CH_2OCH_3$ | $CHC_2H_5$ | | |
| 137 | 4-$COCH_3$ | $CHC_2H_5$ | | |
| 138 | 2-$CH_3$-4-$COCH_3$ | $CHC_2H_5$ | | |
| 139 | 4-$C(CH_3)$=$NOCH_2CH$=$CH_2$ | $CHC_2H_5$ | | |
| 140 | 2-$CH_3$-4-$C(CH_3)$=$NOCH_2CH$=$CH_2$ | $CHC_2H_5$ | | |

TABLE IV

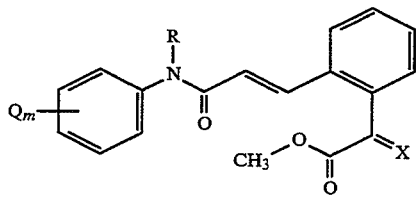

| No. | $Q_m$ | R | X | m.p. (°C.) | δ (C=C$\underline{H}$) |
|---|---|---|---|---|---|
| 1 | 3-F | H | $CHOCH_3$ | 165–168 | |
| 2 | 2,6-$F_2$ | H | $CHOCH_3$ | | |
| 3 | 2-Cl | H | $CHOCH_3$ | | |
| 4 | 3-Cl | H | $CHOCH_3$ | | |
| 5 | 4-Cl | H | $CHOCH_3$ | | |
| 6 | 2,6-$Cl_2$ | H | $CHOCH_3$ | | |
| 7 | 3,4-$Cl_2$ | H | $CHOCH_3$ | | |
| 8 | 3-Br | H | $CHOCH_3$ | | |
| 9 | 4-I | H | $CHOCH_3$ | | |
| 10 | 2-Cl, 6-F | H | $CHOCH_3$ | | |
| 11 | 2-$CH_3$ | H | $CHOCH_3$ | | |
| 12 | 3-$CH_3$ | H | $CHOCH_3$ | 150–152 | |
| 13 | 4-$CH_3$ | H | $CHOCH_3$ | | |
| 14 | 2,4-$(CH_3)_2$ | H | $CHOCH_3$ | | |
| 15 | 2,4,6-$(CH_3)_3$ | H | $CHOCH_3$ | | |
| 16 | 3-$C_2H_5$ | H | $CHOCH_3$ | | |
| 17 | 4-t-$C_4H_9$ | H | $CHOCH_3$ | | |
| 18 | 4-Cyclohexyl | H | $CHOCH_3$ | | |
| 19 | 3-$CH_2C_6H_5$ | H | $CHOCH_3$ | | |
| 20 | 2-$OCH_3$ | H | $CHOCH_3$ | | |
| 21 | 3-$OCH_3$ | H | $CHOCH_3$ | | |
| 22 | 4-$OCH_3$ | H | $CHOCH_3$ | | |
| 23 | 2-O-i-$C_3H_7$ | H | $CHOCH_3$ | | |
| 24 | 3-$OCH_2C_6H_5$ | H | $CHOCH_3$ | | |
| 25 | 3-$CF_3$ | H | $CHOCH_3$ | | |
| 26 | 3-$NO_2$ | H | $CHOCH_3$ | | |
| 27 | 4-$NO_2$ | H | $CHOCH_3$ | | |
| 28 | 3-Cyano | H | $CHOCH_3$ | | |
| 29 | 2-Cl, 4-$CH_3$ | H | $CHOCH_3$ | | |
| 30 | 2-$COOCH_3$ | H | $CHOCH_3$ | 140–143 | |

TABLE IV-continued

| No. | $Q_m$ | R | X | m.p. (°C.) | δ (C=CH) |
|---|---|---|---|---|---|
| 31 | 4-CH$_2$OCH$_3$ | H | CHOCH$_3$ | | |
| 32 | 4-COCH$_3$ | H | CHOCH$_3$ | | |
| 33 | 2-CH$_3$-4-COCH$_3$ | H | CHOCH$_3$ | | |
| 34 | 4-C(CH$_3$)=NOCH$_2$CH=CH$_2$ | H | CHOCH$_3$ | | |
| 35 | 2-CH$_3$-4-C(CH$_3$)=NOCH$_2$CH=CH$_2$ | H | CHOCH$_3$ | | |
| 36 | 3-F | CH$_3$ | CHOCH$_3$ | | |
| 37 | 2,6-F$_2$ | CH$_3$ | CHOCH$_3$ | | |
| 38 | 2-Cl | CH$_3$ | CHOCH$_3$ | | |
| 39 | 3-Cl | CH$_3$ | CHOCH$_3$ | | |
| 40 | 4-Cl | CH$_3$ | CHOCH$_3$ | | |
| 41 | 2,6-Cl$_2$ | CH$_3$ | CHOCH$_3$ | | |
| 42 | 3,4-Cl$_2$ | CH$_3$ | CHOCH$_3$ | | |
| 43 | 3-Br | CH$_3$ | CHOCH$_3$ | | |
| 44 | 4-I | CH$_3$ | CHOCH$_3$ | | |
| 45 | 2-Cl, 6-F | CH$_3$ | CHOCH$_3$ | | |
| 46 | 2-CH$_3$ | CH$_3$ | CHOCH$_3$ | | |
| 47 | 3-CH$_3$ | CH$_3$ | CHOCH$_3$ | | |
| 48 | 4-CH$_3$ | CH$_3$ | CHOCH$_3$ | | |
| 49 | 2,4-(CH$_3$)$_2$ | CH$_3$ | CHOCH$_3$ | | |
| 50 | 2,4,6-(CH$_3$)$_3$ | CH$_3$ | CHOCH$_3$ | | |
| 51 | 3-C$_2$H$_5$ | CH$_3$ | CHOCH$_3$ | | |
| 52 | 4-t-C$_4$H$_9$ | CH$_3$ | CHOCH$_3$ | | |
| 53 | 4-Cyclohexyl | CH$_3$ | CHOCH$_3$ | | |
| 54 | 3-CH$_2$C$_6$H$_5$ | CH$_3$ | CHOCH$_3$ | | |
| 55 | 2-OCH$_3$ | CH$_3$ | CHOCH$_3$ | | |
| 56 | 3-OCH$_3$ | CH$_3$ | CHOCH$_3$ | | |
| 57 | 4-OCH$_3$ | CH$_3$ | CHOCH$_3$ | | |
| 58 | 2-O-i-C$_3$H$_7$ | CH$_3$ | CHOCH$_3$ | | |
| 59 | 3-OCH$_2$C$_6$H$_5$ | CH$_3$ | CHOCH$_3$ | | |
| 60 | 3-CF$_3$ | CH$_3$ | CHOCH$_3$ | | |
| 61 | 3-NO$_2$ | CH$_3$ | CHOCH$_3$ | | |
| 62 | 4-NO$_2$ | CH$_3$ | CHOCH$_3$ | | |
| 63 | 3-Cyano | CH$_3$ | CHOCH$_3$ | | |
| 64 | 2-Cl, 4-CH$_3$ | CH$_3$ | CHOCH$_3$ | | |
| 65 | 2-COOCH$_3$ | CH$_3$ | CHOCH$_3$ | | |
| 66 | 4-CH$_2$OCH$_3$ | CH$_3$ | CHOCH$_3$ | | |
| 67 | 4-COCH$_3$ | CH$_3$ | CHOCH$_3$ | | |
| 68 | 2-CH$_3$-4-COCH$_3$ | CH$_3$ | CHOCH$_3$ | | |
| 69 | 4-C(CH$_3$)=NOCH$_2$CH=CH$_2$ | CH$_3$ | CHOCH$_3$ | | |
| 70 | 2-CH$_3$-4-C(CH$_3$)=NOCH$_2$CH=CH$_2$ | CH$_3$ | CHOCH$_3$ | | |
| 71 | 3-F | H | NOCH$_3$ | 138–141 | |
| 72 | 2,6-F$_2$ | H | NOCH$_3$ | | |
| 73 | 2-Cl | H | NOCH$_3$ | | |
| 74 | 3-Cl | H | NOCH$_3$ | | |
| 75 | 4-Cl | H | NOCH$_3$ | | |
| 76 | 2,6-Cl$_2$ | H | NOCH$_3$ | | |
| 77 | 3,4-Cl$_2$ | H | NOCH$_3$ | | |
| 78 | 3-Br | H | NOCH$_3$ | | |
| 79 | 4-I | H | NOCH$_3$ | | |
| 80 | 2-Cl, 6-F | H | NOCH$_3$ | | |
| 81 | 2-CH$_3$ | H | NOCH$_3$ | | |
| 82 | 3-CH$_3$ | H | NOCH$_3$ | 125–127 | |
| 83 | 4-CH$_3$ | H | NOCH$_3$ | | |
| 84 | 2,4-(CH$_3$)$_2$ | H | NOCH$_3$ | | |
| 85 | 2,4,6-(CH$_3$)$_3$ | H | NOCH$_3$ | | |
| 86 | 3-C$_2$H$_5$ | H | NOCH$_3$ | | |
| 87 | 4-t-C$_4$H$_9$ | H | NOCH$_3$ | | |
| 88 | 4-Cyclohexyl | H | NOCH$_3$ | | |
| 89 | 3-CH$_2$C$_6$H$_5$ | H | NOCH$_3$ | | |
| 90 | 2-OCH$_3$ | H | NOCH$_3$ | | |
| 91 | 3-OCH$_3$ | H | NOCH$_3$ | | |
| 92 | 4-OCH$_3$ | H | NOCH$_3$ | | |
| 93 | 2-O-i-C$_3$H$_7$ | H | NOCH$_3$ | | |
| 94 | 3-OCH$_2$C$_6$H$_5$ | H | NOCH$_3$ | | |
| 95 | 3-CF$_3$ | H | NOCH$_3$ | | |
| 96 | 3-NO$_2$ | H | NOCH$_3$ | | |
| 97 | 4-NO$_2$ | H | NOCH$_3$ | | |
| 98 | 3-Cyano | H | NOCH$_3$ | | |
| 99 | 2-Cl, 4-CH$_3$ | H | NOCH$_3$ | | |

TABLE IV-continued

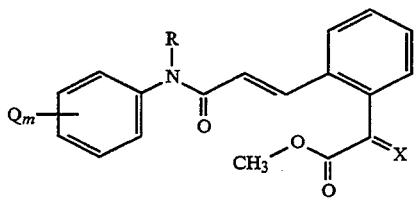

| No. | $Q_m$ | R | X | m.p. (°C.) | δ (C=C$\underline{H}$) |
|---|---|---|---|---|---|
| 100 | 2-COOCH$_3$ | H | NOCH$_3$ | 165 (decomp.) | |
| 101 | 4-CH$_2$OCH$_3$ | H | NOCH$_3$ | | |
| 102 | 4-COCH$_3$ | H | NOCH$_3$ | | |
| 103 | 2-CH$_3$-4-COCH$_3$ | H | NOCH$_3$ | | |
| 104 | 4-C(CH$_3$)=NOCH$_2$CH=CH$_2$ | H | NOCH$_3$ | | |
| 105 | 2-CH$_3$-4-C(CH$_3$)=NOCH$_2$CH=CH$_2$ | H | NOCH$_3$ | | |
| 106 | 3-F | CH$_3$ | NOCH$_3$ | | |
| 107 | 2,6-F$_2$ | CH$_3$ | NOCH$_3$ | | |
| 108 | 2-Cl | CH$_3$ | NOCH$_3$ | | |
| 109 | 3-Cl | CH$_3$ | NOCH$_3$ | | |
| 110 | 4-Cl | CH$_3$ | NOCH$_3$ | | |
| 111 | 2,6-Cl$_2$ | CH$_3$ | NOCH$_3$ | | |
| 112 | 3,4-Cl$_2$ | CH$_3$ | NOCH$_3$ | | |
| 113 | 3-Br | CH$_3$ | NOCH$_3$ | | |
| 114 | 4-I | CH$_3$ | NOCH$_3$ | | |
| 115 | 2-Cl, 6-F | CH$_3$ | NOCH$_3$ | | |
| 116 | 2-CH$_3$ | CH$_3$ | NOCH$_3$ | | |
| 117 | 3-CH$_3$ | CH$_3$ | NOCH$_3$ | | |
| 118 | 4-CH$_3$ | CH$_3$ | NOCH$_3$ | | |
| 119 | 2,4-(CH$_3$)$_2$ | CH$_3$ | NOCH$_3$ | | |
| 120 | 2,4,6-(CH$_3$)$_3$ | CH$_3$ | NOCH$_3$ | | |
| 121 | 3-C$_2$H$_5$ | CH$_3$ | NOCH$_3$ | | |
| 122 | 4-t-C$_4$H$_9$ | CH$_3$ | NOCH$_3$ | | |
| 123 | 4-Cyclohexyl | CH$_3$ | NOCH$_3$ | | |
| 124 | 3-CH$_2$C$_6$H$_5$ | CH$_3$ | NOCH$_3$ | | |
| 125 | 2-OCH$_3$ | CH$_3$ | NOCH$_3$ | | |
| 126 | 3-OCH$_3$ | CH$_3$ | NOCH$_3$ | | |
| 127 | 4-OCH$_3$ | CH$_3$ | NOCH$_3$ | | |
| 128 | 2-O-i-C$_3$H$_7$ | CH$_3$ | NOCH$_3$ | | |
| 129 | 3-OCH$_2$C$_6$H$_5$ | CH$_3$ | NOCH$_3$ | | |
| 130 | 3-CF$_3$ | CH$_3$ | NOCH$_3$ | | |
| 131 | 3-NO$_2$ | CH$_3$ | NOCH$_3$ | | |
| 132 | 4-NO$_2$ | CH$_3$ | NOCH$_3$ | | |
| 133 | 3-Cyano | CH$_3$ | NOCH$_3$ | | |
| 134 | 2-Cl, 4-CH$_3$ | CH$_3$ | NOCH$_3$ | | |
| 135 | 2-COOCH$_3$ | CH$_3$ | NOCH$_3$ | | |
| 136 | 4-CH$_2$OCH$_3$ | CH$_3$ | NOCH$_3$ | | |
| 137 | 4-COCH$_3$ | CH$_3$ | NOCH$_3$ | | |
| 138 | 2-CH$_3$-4-COCH$_3$ | CH$_3$ | NOCH$_3$ | | |
| 139 | 4-C(CH$_3$)=NOCH$_2$CH=CH$_2$ | CH$_3$ | NOCH$_3$ | | |
| 140 | 2-CH$_3$-4-C(CH$_3$)=NOCH$_2$CH=CH$_2$ | CH$_3$ | NOCH$_3$ | | |
| 141 | 3-F | H | CHCH$_3$ | | |
| 142 | 2,6-F$_2$ | H | CHCH$_3$ | | |
| 143 | 2-Cl | H | CHCH$_3$ | | |
| 144 | 3-Cl | H | CHCH$_3$ | | |
| 145 | 4-Cl | H | CHCH$_3$ | | |
| 146 | 2,6-Cl$_2$ | H | CHCH$_3$ | | |
| 147 | 3,4-Cl$_2$ | H | CHCH$_3$ | | |
| 148 | 3-Br | H | CHCH$_3$ | | |
| 149 | 4-I | H | CHCH$_3$ | | |
| 150 | 2-Cl, 6-F | H | CHCH$_3$ | | |
| 151 | 2-CH$_3$ | H | CHCH$_3$ | | |
| 152 | 3-CH$_3$ | H | CHCH$_3$ | | |
| 153 | 4-CH$_3$ | H | CHCH$_3$ | | |
| 154 | 2,4-(CH$_3$)$_2$ | H | CHCH$_3$ | | |
| 155 | 2,4,6-(CH$_3$)$_3$ | H | CHCH$_3$ | | |
| 156 | 3-C$_2$H$_5$ | H | CHCH$_3$ | | |
| 157 | 4-t-C$_4$H$_9$ | H | CHCH$_3$ | | |
| 158 | 4-Cyclohexyl | H | CHCH$_3$ | | |
| 159 | 3-CH$_2$C$_6$H$_5$ | H | CHCH$_3$ | | |
| 160 | 2-OCH$_3$ | H | CHCH$_3$ | | |
| 161 | 3-OCH$_3$ | H | CHCH$_3$ | | |
| 162 | 4-OCH$_3$ | H | CHCH$_3$ | | |
| 163 | 2-O-i-C$_3$H$_7$ | H | CHCH$_3$ | | |
| 164 | 3-OCH$_2$C$_6$H$_5$ | H | CHCH$_3$ | | |
| 165 | 3-CF$_3$ | H | CHCH$_3$ | | |
| 166 | 3-NO$_2$ | H | CHCH$_3$ | | |

TABLE IV-continued

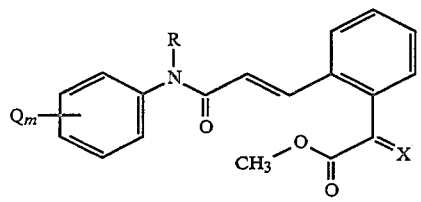

| No. | Q_m | R | X | m.p. (°C.) | δ (C=CH) |
|---|---|---|---|---|---|
| 167 | 4-NO$_2$ | H | CHCH$_3$ | | |
| 168 | 3-Cyano | H | CHCH$_3$ | | |
| 169 | 2-Cl, 4-CH$_3$ | H | CHCH$_3$ | | |
| 170 | 2-COOCH$_3$ | H | CHCH$_3$ | | |
| 171 | 4-CH$_2$OCH$_3$ | H | CHCH$_3$ | | |
| 172 | 4-COCH$_3$ | H | CHCH$_3$ | | |
| 173 | 2-CH$_3$-4-COCH$_3$ | H | CHCH$_3$ | | |
| 174 | 4-C(CH$_3$)=NOCH$_2$CH=CH$_2$ | H | CHCH$_3$ | | |
| 175 | 2-CH$_3$-4-C(CH$_3$)=NOCH$_2$CH=CH$_2$ | H | CHCH$_3$ | | |
| 176 | 3-F | CH$_3$ | CHCH$_3$ | | |
| 177 | 2,6-F$_2$ | CH$_3$ | CHCH$_3$ | | |
| 178 | 2-Cl | CH$_3$ | CHCH$_3$ | | |
| 179 | 3-Cl | CH$_3$ | CHCH$_3$ | | |
| 180 | 4-Cl | CH$_3$ | CHCH$_3$ | | |
| 181 | 2,6-Cl$_2$ | CH$_3$ | CHCH$_3$ | | |
| 182 | 3,4-Cl$_2$ | CH$_3$ | CHCH$_3$ | | |
| 183 | 3-Br | CH$_3$ | CHCH$_3$ | | |
| 184 | 4-I | CH$_3$ | CHCH$_3$ | | |
| 185 | 2-Cl, 6-F | CH$_3$ | CHCH$_3$ | | |
| 186 | 2-CH$_3$ | CH$_3$ | CHCH$_3$ | | |
| 187 | 3-CH$_3$ | CH$_3$ | CHCH$_3$ | | |
| 188 | 4-CH$_3$ | CH$_3$ | CHCH$_3$ | | |
| 189 | 2,4-(CH$_3$)$_2$ | CH$_3$ | CHCH$_3$ | | |
| 190 | 2,4,6-(CH$_3$)$_3$ | CH$_3$ | CHCH$_3$ | | |
| 191 | 3-C$_2$H$_5$ | CH$_3$ | CHCH$_3$ | | |
| 192 | 4-t-C$_4$H$_9$ | CH$_3$ | CHCH$_3$ | | |
| 193 | 4-Cyclohexyl | CH$_3$ | CHCH$_3$ | | |
| 194 | 3-CH$_2$C$_6$H$_5$ | CH$_3$ | CHCH$_3$ | | |
| 195 | 2-OCH$_3$ | CH$_3$ | CHCH$_3$ | | |
| 196 | 3-OCH$_3$ | CH$_3$ | CHCH$_3$ | | |
| 197 | 4-OCH$_3$ | CH$_3$ | CHCH$_3$ | | |
| 198 | 2-O-i-C$_3$H$_7$ | CH$_3$ | CHCH$_3$ | | |
| 199 | 3-OCH$_2$C$_6$H$_5$ | CH$_3$ | CHCH$_3$ | | |
| 200 | 3-CF$_3$ | CH$_3$ | CHCH$_3$ | | |
| 201 | 3-NO$_2$ | CH$_3$ | CHCH$_3$ | | |
| 202 | 4-NO$_2$ | CH$_3$ | CHCH$_3$ | | |
| 203 | 3-Cyano | CH$_3$ | CHCH$_3$ | | |
| 204 | 2-Cl, 4-CH$_3$ | CH$_3$ | CHCH$_3$ | | |
| 205 | 2-COOCH$_3$ | CH$_3$ | CHCH$_3$ | | |
| 206 | 4-CH$_2$OCH$_3$ | CH$_3$ | CHCH$_3$ | | |
| 207 | 4-COCH$_3$ | CH$_3$ | CHCH$_3$ | | |
| 208 | 2-CH$_3$-4-COCH$_3$ | CH$_3$ | CHCH$_3$ | | |
| 209 | 4-C(CH$_3$)=NOCH$_2$CH=CH$_2$ | CH$_3$ | CHCH$_3$ | | |
| 210 | 2-CH$_3$-4-C(CH$_3$)=NOCH$_2$CH=CH$_2$ | CH$_3$ | CHCH$_3$ | | |
| 211 | 3-F | H | CHC$_2$H$_5$ | | |
| 212 | 2,6-F$_2$ | H | CHC$_2$H$_5$ | | |
| 213 | 2-Cl | H | CHC$_2$H$_5$ | | |
| 214 | 3-Cl | H | CHC$_2$H$_5$ | | |
| 215 | 4-Cl | H | CHC$_2$H$_5$ | | |
| 216 | 2,6-Cl$_2$ | H | CHC$_2$H$_5$ | | |
| 217 | 3,4-Cl$_2$ | H | CHC$_2$H$_5$ | | |
| 218 | 3-Br | H | CHC$_2$H$_5$ | | |
| 219 | 4-I | H | CHC$_2$H$_5$ | | |
| 220 | 2-Cl, 6-F | H | CHC$_2$H$_5$ | | |
| 221 | 2-CH$_3$ | H | CHC$_2$H$_5$ | | |
| 222 | 3-CH$_3$ | H | CHC$_2$H$_5$ | | |
| 223 | 4-CH$_3$ | H | CHC$_2$H$_5$ | | |
| 224 | 2,4-(CH$_3$)$_2$ | H | CHC$_2$H$_5$ | | |
| 225 | 2,4,6-(CH$_3$)$_3$ | H | CHC$_2$H$_5$ | | |
| 226 | 3-C$_2$H$_5$ | H | CHC$_2$H$_5$ | | |
| 227 | 4-t-C$_4$H$_9$ | H | CHC$_2$H$_5$ | | |
| 228 | 4-Cyclohexyl | H | CHC$_2$H$_5$ | | |
| 229 | 3-CH$_2$C$_6$H$_5$ | H | CHC$_2$H$_5$ | | |
| 230 | 2-OCH$_3$ | H | CHC$_2$H$_5$ | | |
| 231 | 3-OCH$_3$ | H | CHC$_2$H$_5$ | | |
| 232 | 4-OCH$_3$ | H | CHC$_2$H$_5$ | | |
| 233 | 2-O-i-C$_3$H$_7$ | H | CHC$_2$H$_5$ | | |
| 234 | 3-OCH$_2$C$_6$H$_5$ | H | CHC$_2$H$_5$ | | |
| 235 | 3-CF$_3$ | H | CHC$_2$H$_5$ | | |

TABLE IV-continued

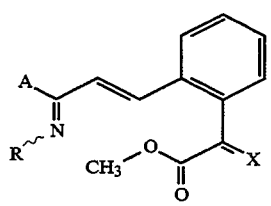

| No. | $Q_m$ | R | X | m.p. (°C.) | δ (C=C$\underline{H}$) |
|---|---|---|---|---|---|
| 236 | 3-NO$_2$ | H | CHC$_2$H$_5$ | | |
| 237 | 4-NO$_2$ | H | CHC$_2$H$_5$ | | |
| 238 | 3-Cyano | H | CHC$_2$H$_5$ | | |
| 239 | 2-Cl, 4-CH$_3$ | H | CHC$_2$H$_5$ | | |
| 240 | 2-COOCH$_3$ | H | CHC$_2$H$_5$ | | |
| 241 | 4-CH$_2$OCH$_3$ | H | CHC$_2$H$_5$ | | |
| 242 | 4-COCH$_3$ | H | CHC$_2$H$_5$ | | |
| 243 | 2-CH$_3$-4-COCH$_3$ | H | CHC$_2$H$_5$ | | |
| 244 | 4-C(CH$_3$)=NOCH$_2$CH=CH$_2$ | H | CHC$_2$H$_5$ | | |
| 245 | 2-CH$_3$-4-C(CH$_3$)=NOCH$_2$CH=CH$_2$ | H | CHC$_2$H$_5$ | | |
| 246 | 3-F | CH$_3$ | CHC$_2$H$_5$ | | |
| 247 | 2,6-F$_2$ | CH$_3$ | CHC$_2$H$_5$ | | |
| 248 | 2-Cl | CH$_3$ | CHC$_2$H$_5$ | | |
| 249 | 3-Cl | CH$_3$ | CHC$_2$H$_5$ | | |
| 250 | 4-Cl | CH$_3$ | CHC$_2$H$_5$ | | |
| 251 | 2,6-Cl$_2$ | CH$_3$ | CHC$_2$H$_5$ | | |
| 252 | 3,4-Cl$_2$ | CH$_3$ | CHC$_2$H$_5$ | | |
| 253 | 3-Br | CH$_3$ | CHC$_2$H$_5$ | | |
| 254 | 4-I | CH$_3$ | CHC$_2$H$_5$ | | |
| 255 | 2-Cl, 6-F | CH$_3$ | CHC$_2$H$_5$ | | |
| 256 | 2-CH$_3$ | CH$_3$ | CHC$_2$H$_5$ | | |
| 257 | 3-CH$_3$ | CH$_3$ | CHC$_2$H$_5$ | | |
| 258 | 4-CH$_3$ | CH$_3$ | CHC$_2$H$_5$ | | |
| 259 | 2,4-(CH$_3$)$_2$ | CH$_3$ | CHC$_2$H$_5$ | | |
| 260 | 2,4,6-(CH$_3$)$_3$ | CH$_3$ | CHC$_2$H$_5$ | | |
| 261 | 3-C$_2$H$_5$ | CH$_3$ | CHC$_2$H$_5$ | | |
| 262 | 4-t-C$_4$H$_9$ | CH$_3$ | CHC$_2$H$_5$ | | |
| 263 | 4-Cyclohexyl | CH$_3$ | CHC$_2$H$_5$ | | |
| 264 | 2-CH$_2$C$_6$H$_5$ | CH$_3$ | CHC$_2$H$_5$ | | |
| 265 | 2-OCH$_3$ | CH$_3$ | CHC$_2$H$_5$ | | |
| 266 | 3-OCH$_3$ | CH$_3$ | CHC$_2$H$_5$ | | |
| 267 | 4-OCH$_3$ | CH$_3$ | CHC$_2$H$_5$ | | |
| 268 | 2-O-i-C$_3$H$_7$ | CH$_3$ | CHC$_2$H$_5$ | | |
| 269 | 3-OCH$_2$C$_6$H$_5$ | CH$_3$ | CHC$_2$H$_5$ | | |
| 270 | 3-CF$_3$ | CH$_3$ | CHC$_2$H$_5$ | | |
| 271 | 3-NO$_2$ | CH$_3$ | CHC$_2$H$_5$ | | |
| 272 | 4-NO$_2$ | CH$_3$ | CHC$_2$H$_5$ | | |
| 273 | 3-Cyano | CH$_3$ | CHC$_2$H$_5$ | | |
| 274 | 2-Cl, 4-CH$_3$ | CH$_3$ | CHC$_2$H$_5$ | | |
| 275 | 2-COOCH$_3$ | CH$_3$ | CHC$_2$H$_5$ | | |
| 276 | 4-CH$_2$OCH$_3$ | CH$_3$ | CHC$_2$H$_5$ | | |
| 277 | 4-COCH$_3$ | CH$_3$ | CHC$_2$H$_5$ | | |
| 278 | 2-CH$_3$-4-COCH$_3$ | CH$_3$ | CHC$_2$H$_5$ | | |
| 279 | 4-C(CH$_3$)=NOCH$_2$CH=CH$_2$ | CH$_3$ | CHC$_2$H$_5$ | | |
| 280 | 2-CH$_3$-4-C(CH$_3$)=NOCH$_2$CH=CH$_2$ | CH$_3$ | CHC$_2$H$_5$ | | |

TABLE V

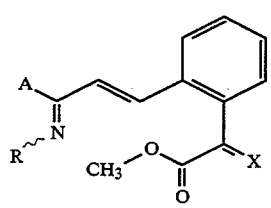

| No. | R | A | X | Isomer | m.p. (°C.) | δ (C=C$\underline{H}$) |
|---|---|---|---|---|---|---|
| 1 | CH$_3$ | H | CHOCH$_3$ | | | |
| 2 | t-C$_4$H$_9$ | H | CHOCH$_3$ | | | |
| 3 | C$_6$H$_5$ | H | CHOCH$_3$ | | | |
| 4 | 2-ClC$_6$H$_4$ | H | CHOCH$_3$ | | | |
| 5 | 3-ClC$_6$H$_4$ | H | CHOCH$_3$ | | | |
| 6 | 4-ClC$_6$H$_4$ | H | CHOCH$_3$ | | | |
| 7 | 2-CH$_3$C$_6$H$_4$ | H | CHOCH$_3$ | | | |
| 8 | 3-CH$_3$OC$_6$H$_4$ | H | CHOCH$_3$ | | | |
| 9 | 4-Cyano-C$_6$H$_4$ | H | CHOCH$_3$ | | | |
| 10 | 2,6-F$_2$—C$_6$H$_3$ | H | CHOCH$_3$ | | | |
| 11 | 3-Pyridyl | H | CHOCH$_3$ | | | |
| 12 | 2-Furyl | H | CHOCH$_3$ | | | |
| 13 | β-Naphthyl | H | CHOCH$_3$ | | | |
| 14 | CH$_3$ | CH$_3$ | CHOCH$_3$ | | | |

TABLE V-continued

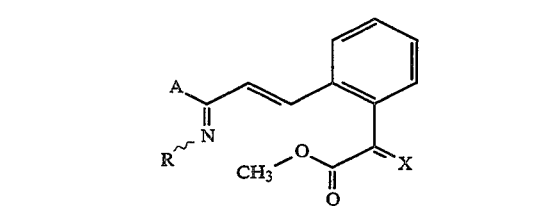

| No. | R | A | X | Isomer | m.p. (°C.) | δ (C=CH) |
|---|---|---|---|---|---|---|
| 15 | t-C$_4$H$_9$ | CH$_3$ | CHOCH$_3$ | | | |
| 16 | C$_6$H$_5$ | CH$_3$ | CHOCH$_3$ | | | |
| 17 | 2-ClC$_6$H$_4$ | CH$_3$ | CHOCH$_3$ | | | |
| 18 | 3-ClC$_6$H$_4$ | CH$_3$ | CHOCH$_3$ | | | |
| 19 | 4-ClC$_6$H$_4$ | CH$_3$ | CHOCH$_3$ | | | |
| 20 | 2-CH$_3$C$_6$H$_4$ | CH$_3$ | CHOCH$_3$ | | | |
| 21 | 3-CH$_3$OC$_6$H$_4$ | CH$_3$ | CHOCH$_3$ | | | |
| 22 | 4-Cyano-C$_6$H$_4$ | CH$_3$ | CHOCH$_3$ | | | |
| 23 | 2,6-F$_2$—C$_6$H$_3$ | CH$_3$ | CHOCH$_3$ | | | |
| 24 | 3-Pyridyl | CH$_3$ | CHOCH$_3$ | | | |
| 25 | 2-Furyl | CH$_3$ | CHOCH$_3$ | | | |
| 26 | β-Napthhyl | CH$_3$ | CHOCH$_3$ | | | |
| 27 | CH$_3$ | C$_6$H$_5$ | CHOCH$_3$ | | | |
| 28 | C$_6$H$_5$ | C$_6$H$_5$ | CHOCH$_3$ | | | |
| 29 | 2-CH$_3$C$_6$H$_4$ | C$_6$H$_5$ | CHOCH$_3$ | | | |
| 30 | 2,6-F$_2$C$_6$H$_3$ | C$_6$H$_5$ | CHOCH$_3$ | | | |
| 31 | CH$_3$ | H | NOCH$_3$ | | | |
| 32 | t-C$_4$H$_9$ | H | NOCH$_3$ | | | |
| 33 | C$_6$H$_5$ | H | NOCH$_3$ | | | |
| 34 | 2-ClC$_6$H$_4$ | H | NOCH$_3$ | | | |
| 35 | 3-ClC$_6$H$_4$ | H | NOCH$_3$ | | | |
| 36 | 4-ClC$_6$H$_4$ | H | NOCH$_3$ | | | |
| 37 | 2-CH$_3$C$_6$H$_4$ | H | NOCH$_3$ | | | |
| 38 | 3-CH$_3$OC$_6$H$_4$ | H | NOCH$_3$ | | | |
| 39 | 4-Cyano-C$_6$H$_4$ | H | NOCH$_3$ | | | |
| 40 | 2,6-F$_2$—C$_6$H$_3$ | H | NOCH$_3$ | | | |
| 41 | 3-Pyridyl | H | NOCH$_3$ | | | |
| 42 | 2-Furyl | H | NOCH$_3$ | | | |
| 43 | β-Naphthyl | H | NOCH$_3$ | | | |
| 44 | CH$_3$ | CH$_3$ | NOCH$_3$ | | | |
| 45 | t-C$_4$H$_9$ | CH$_3$ | NOCH$_3$ | | | |
| 46 | C$_6$H$_5$ | CH$_3$ | NOCH$_3$ | | | |
| 47 | 2-ClC$_6$H$_4$ | CH$_3$ | NOCH$_3$ | | | |
| 48 | 3-ClC$_6$H$_4$ | CH$_3$ | NOCH$_3$ | | | |
| 49 | 4-ClC$_6$H$_4$ | CH$_3$ | NOCH$_3$ | | | |
| 50 | 2-CH$_3$C$_6$H$_4$ | CH$_3$ | NOCH$_3$ | | | |
| 51 | 3-CH$_3$OC$_6$H$_4$ | CH$_3$ | NOCH$_3$ | | | |
| 52 | 4-Cyano-C$_6$H$_4$ | CH$_3$ | NOCH$_3$ | | | |
| 53 | 2,6-F$_2$—C$_6$H$_3$ | CH$_3$ | NOCH$_3$ | | | |
| 54 | 3-Pyridyl | CH$_3$ | NOCH$_3$ | | | |
| 55 | 2-Furyl | CH$_3$ | NOCH$_3$ | | | |
| 56 | β-Naphthyl | CH$_3$ | NOCH$_3$ | | | |
| 57 | CH$_3$ | C$_6$H$_5$ | NOCH$_3$ | | | |
| 58 | C$_6$H$_5$ | C$_6$H$_5$ | NOCH$_3$ | | | |
| 59 | 2-CH$_3$C$_6$H$_4$ | C$_6$H$_5$ | NOCH$_3$ | | | |
| 60 | 2,6-F$_2$C$_6$H$_3$ | C$_6$H$_5$ | NOCH$_3$ | | | |
| 61 | CH$_3$ | H | CHCH$_3$ | | | |
| 62 | t-C$_4$H$_9$ | H | CHCH$_3$ | | | |
| 63 | C$_6$H$_5$ | H | CHCH$_3$ | | | |
| 64 | 2-ClC$_6$H$_4$ | H | CHCH$_3$ | | | |
| 65 | 3-ClC$_6$H$_4$ | H | CHCH$_3$ | | | |
| 66 | 4-ClC$_6$H$_4$ | H | CHCH$_3$ | | | |
| 67 | 2-CH$_3$C$_6$H$_4$ | H | CHCH$_3$ | | | |
| 68 | 3-CH$_3$OC$_6$H$_4$ | H | CHCH$_3$ | | | |
| 69 | 4-Cyano-C$_6$H$_4$ | H | CHCH$_3$ | | | |
| 70 | 2,6-F$_2$—C$_6$H$_3$ | H | CHCH$_3$ | | | |
| 71 | 3-Pyridyl | H | CHCH$_3$ | | | |
| 72 | 2-Furyl | H | CHCH$_3$ | | | |
| 73 | β-Napthhyl | H | CHCH$_3$ | | | |
| 74 | CH$_3$ | CH$_3$ | CHCH$_3$ | | | |
| 75 | t-C$_4$H$_9$ | CH$_3$ | CHCH$_3$ | | | |
| 76 | C$_6$H$_5$ | CH$_3$ | CHCH$_3$ | | | |
| 77 | 2-ClC$_6$H$_4$ | CH$_3$ | CHCH$_3$ | | | |
| 78 | 3-ClC$_6$H$_4$ | CH$_3$ | CHCH$_3$ | | | |
| 79 | 4-ClC$_6$H$_4$ | CH$_3$ | CHCH$_3$ | | | |
| 80 | 2-CH$_3$C$_6$H$_4$ | CH$_3$ | CHCH$_3$ | | | |
| 81 | 3-CH$_3$OC$_6$H$_4$ | CH$_3$ | CHCH$_3$ | | | |
| 82 | 4-Cyano-C$_6$H$_4$ | CH$_3$ | CHCH$_3$ | | | |
| 83 | 2,6-F$_2$—C$_6$H$_3$ | CH$_3$ | CHCH$_3$ | | | |
| 84 | 3-Pyridyl | CH$_3$ | CHCH$_3$ | | | |
| 85 | 2-Furyl | CH$_3$ | CHCH$_3$ | | | |
| 86 | β-Naphthyl | CH$_3$ | CHCH$_3$ | | | |
| 87 | CH$_3$ | C$_6$H$_5$ | CHCH$_3$ | | | |
| 88 | C$_6$H$_5$ | C$_6$H$_5$ | CHCH$_3$ | | | |
| 89 | 2-CH$_3$C$_6$H$_4$ | C$_6$H$_5$ | CHCH$_3$ | | | |
| 90 | 2,6-F$_2$C$_6$H$_3$ | C$_6$H$_5$ | CHCH$_3$ | | | |
| 91 | CH$_3$ | H | CHC$_2$H$_5$ | | | |
| 92 | t-C$_4$H$_9$ | H | CHC$_2$H$_5$ | | | |
| 93 | C$_6$H$_5$ | H | CHC$_2$H$_5$ | | | |
| 94 | 2-ClC$_6$H$_4$ | H | CHC$_2$H$_5$ | | | |
| 95 | 3-ClC$_6$H$_4$ | H | CHC$_2$H$_5$ | | | |
| 96 | 4-ClC$_6$H$_4$ | H | CHC$_2$H$_5$ | | | |
| 97 | 2-CH$_3$C$_6$H$_4$ | H | CHC$_2$H$_5$ | | | |
| 98 | 3-CH$_3$OC$_6$H$_4$ | H | CHC$_2$H$_5$ | | | |
| 99 | 4-Cyano-C$_6$H$_4$ | H | CHC$_2$H$_5$ | | | |
| 100 | 2,6-F$_2$—C$_6$H$_3$ | H | CHC$_2$H$_5$ | | | |
| 101 | 3-Pyridyl | H | CHC$_2$H$_5$ | | | |
| 102 | 2-Furyl | H | CHC$_2$H$_5$ | | | |
| 103 | β-Napthhyl | H | CHC$_2$H$_5$ | | | |
| 104 | CH$_3$ | CH$_3$ | CHC$_2$H$_5$ | | | |
| 105 | t-C$_4$H$_9$ | CH$_3$ | CHC$_2$H$_5$ | | | |
| 106 | C$_6$H$_5$ | CH$_3$ | CHC$_2$H$_5$ | | | |
| 107 | 2-ClC$_6$H$_4$ | CH$_3$ | CHC$_2$H$_5$ | | | |
| 108 | 3-ClC$_6$H$_4$ | CH$_3$ | CHC$_2$H$_5$ | | | |
| 109 | 4-ClC$_6$H$_4$ | CH$_3$ | CHC$_2$H$_5$ | | | |
| 110 | 2-CH$_3$C$_6$H$_4$ | CH$_3$ | CHC$_2$H$_5$ | | | |
| 111 | 3-CH$_3$OC$_6$H$_4$ | CH$_3$ | CHC$_2$H$_5$ | | | |
| 112 | 4-Cyano-C$_6$H$_4$ | CH$_3$ | CHC$_2$H$_5$ | | | |
| 113 | 2,6-F$_2$—C$_6$H$_3$ | CH$_3$ | CHC$_2$H$_5$ | | | |
| 114 | 3-Pyridyl | CH$_3$ | CHC$_2$H$_5$ | | | |
| 115 | 2-Furyl | CH$_3$ | CHC$_2$H$_5$ | | | |
| 116 | β-Naphthyl | CH$_3$ | CHC$_2$H$_5$ | | | |
| 117 | CH$_3$ | C$_6$H$_5$ | CHC$_2$H$_5$ | | | |
| 118 | C$_6$H$_5$ | C$_6$H$_5$ | CHC$_2$H$_5$ | | | |
| 119 | 2-CH$_3$C$_6$H$_4$ | C$_6$H$_5$ | CHC$_2$H$_5$ | | | |
| 120 | 2,6-F$_2$C$_6$H$_3$ | C$_6$H$_5$ | CHC$_2$H$_5$ | | | |

TABLE VI

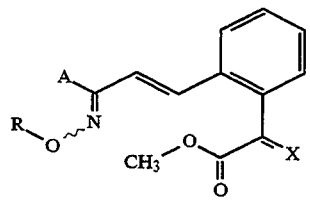

| No. | R | A | X | Isomer | m.p. (°C.) | δ(C=CH) |
|---|---|---|---|---|---|---|
| 1 | H | H | CHOCH$_3$ | | | |
| 2 | CH$_3$ | H | CHOCH$_3$ | | | |
| 3 | C$_2$H$_5$ | H | CHOCH$_3$ | | | |
| 4 | i-C$_3$H$_7$ | H | CHOCH$_3$ | | | |
| 5 | t-C$_4$H$_9$ | H | CHOCH$_3$ | | | |
| 6 | H$_2$C=CH—CH$_2$ | H | CHOCH$_3$ | | | |
| 7 | H$_2$C=CCl—CH$_2$ | H | CHOCH$_3$ | | | |
| 8 | CH$_3$—CCl=CH—CH$_2$ | H | CHOCH$_3$ | | | |
| 9 | H—C≡C—CH$_2$ | H | CHOCH$_3$ | | | |
| 10 | Cyclopropyl | H | CHOCH$_3$ | | | |
| 11 | C$_6$H$_5$ | H | CHOCH$_3$ | | | |
| 12 | 4-Pyridyl | H | CHOCH$_3$ | | | |
| 13 | C$_6$H$_5$CH$_2$ | H | CHOCH$_3$ | | | |
| 14 | 2-Pyridylmethyl | H | CHOCH$_3$ | | | |
| 15 | 5-Chlorothien-2-ylmethyl | H | CHOCH$_3$ | | | |
| 16 | CH$_3$CO | H | CHOCH$_3$ | | | |
| 17 | C$_6$H$_5$CO | H | CHOCH$_3$ | | | |
| 18 | 2-Furyl-CO | H | CHOCH$_3$ | | | |
| 19 | CH$_3$OOCCH$_2$ | H | CHOCH$_3$ | | | |
| 20 | N≡CCH$_2$ | H | CHOCH$_3$ | | | |
| 21 | H | CH$_3$ | CHOCH$_3$ | a | oil | 6.70/6.86 |
|    |   |      |          | s | oil | 6.93/6.54 |
| 22 | CH$_3$ | CH$_3$ | CHOCH$_3$ | a | oil | both 6.81 |
|    |   |      |          | s | oil | 6.90/7.42 |
| 23 | C$_2$H$_5$ | CH$_3$ | CHOCH$_3$ | a(80) | oil | both 6.81 |
|    |   |      |          | s(20) |     | 6.88/7.43 |
| 24 | i-C$_3$H$_7$ | CH$_3$ | CHOCH$_3$ | | oil | both 6.80 |
| 25 | t-C$_4$H$_9$ | CH$_3$ | CHOCH$_3$ | a(80) | oil | 6.76/6.84 |
|    |   |      |          | s(20) | oil | 6.85/7.46 |
| 26 | H$_2$C=CH—CH$_2$ | CH$_3$ | CHOCH$_3$ | a | oil | both 6.81 |
|    |   |      |          | s | oil | 6.90/7.46 |
| 27 | H$_2$C=CCl—CH$_2$ | CH$_3$ | CHOCH$_3$ | a | oil | 6.75/6.87 |
|    |   |      |          | s | oil | 6.92/7.47 |
| 28 | CH$_3$CCl=CH—CH$_2$ | CH$_3$ | CHOCH$_3$ | | | |
| 29 | H—C≡C—CH$_2$ | CH$_3$ | CHOCH$_3$ | | | |
| 30 | Cyclopropyl | CH$_3$ | CHOCH$_3$ | | | |
| 31 | C$_6$H$_5$ | CH$_3$ | CHOCH$_3$ | | | |
| 32 | 4-Pyridyl | CH$_3$ | CHOCH$_3$ | | | |
| 33 | C$_6$H$_5$CH$_2$ | CH$_3$ | CHOCH$_3$ | a(90) | 130–132 | |
|    |   |      |          | s(10) |     | |
| 34 | 2-Pyridylmethyl | CH$_3$ | CHOCH$_3$ | | | |
| 35 | 5-Chlorthien-2-ylmethyl | CH$_3$ | CHOCH$_3$ | | | |
| 36 | CH$_3$CO | CH$_3$ | CHOCH$_3$ | | | |
| 37 | C$_6$H$_5$CO | CH$_3$ | CHOCH$_3$ | | | |
| 38 | 2-Furyl-CO | CH$_3$ | CHOCH$_3$ | | | |
| 39 | CH$_3$OOCCH$_2$ | CH$_3$ | CHOCH$_3$ | | | |
| 40 | N≡CCH$_2$ | CH$_3$ | CHOCH$_3$ | | | |
| 41 | H | C$_6$H$_5$ | CHOCH$_3$ | | | |
| 42 | CH$_3$ | C$_6$H$_5$ | CHOCH$_3$ | | | |
| 43 | C$_6$H$_5$CH$_2$ | C$_6$H$_5$ | CHOCH$_3$ | | | |
| 44 | H$_2$C=CCl—CH$_2$ | C$_6$H$_5$ | CHOCH$_3$ | | | |
| 45 | N≡C—CH$_2$ | C$_6$H$_5$ | CHOCH$_3$ | | | |
| 46 | H | p-CH$_3$OC$_6$H$_4$ | CHOCH$_3$ | | | |
| 47 | CH$_3$ | p-CH$_3$OC$_6$H$_4$ | CHOCH$_3$ | | | |
| 48 | C$_6$H$_5$CH$_2$ | p-CH$_3$OC$_6$H$_4$ | CHOCH$_3$ | | | |
| 49 | H$_2$C=CCl—CH$_2$ | p-CH$_3$OC$_6$H$_4$ | CHOCH$_3$ | | | |
| 50 | N≡C—CH$_2$ | p-CH$_3$OC$_6$H$_4$ | CHOCH$_3$ | | | |
| 51 | H | H | NOCH$_3$ | a | oil | 6.58/6.82 |
| 52 | CH$_3$ | H | NOCH$_3$ | a | 86–88 | |
| 53 | C$_2$H$_5$ | H | NOCH$_3$ | | | |
| 54 | i-C$_3$H$_7$ | H | NOCH$_3$ | | | |
| 55 | t-C$_4$H$_9$ | H | NOCH$_3$ | | | |
| 56 | H$_2$C=CH—CH$_2$ | H | NOCH$_3$ | | | |
| 57 | H$_2$C=CCl—CH$_2$ | H | NOCH$_3$ | | oil | 6.60/6.82 |
|    |   |      |          |   | oil | 6.65/6.80 |
| 58 | CH$_3$—CCl=CH—CH$_2$ | H | NOCH$_3$ | | | |
| 59 | H—C≡C—CH$_2$ | H | NOCH$_3$ | | | |

TABLE VI-continued

| No. | R | A | X | Isomer | m.p. (°C.) | δ(C=CH) |
|---|---|---|---|---|---|---|
| 60 | Cyclopropyl | H | NOCH₃ | | | |
| 61 | C₆H₅ | H | NOCH₃ | | | |
| 62 | 4-Pyridyl | H | NOCH₃ | | | |
| 63 | C₆H₅CH₂ | H | NOCH₃ | a(85) s(15) | 81–83 | |
| 64 | 2-Pyridylmethyl | H | NOCH₃ | | | |
| 65 | 5-Chlorothien-2-ylmethyl | H | NOCH₃ | | | |
| 66 | CH₃CO | H | NOCH₃ | | | |
| 67 | C₆H₅CO | H | NOCH₃ | | | |
| 68 | 2-Furyl-CO | H | NOCH₃ | | | |
| 69 | CH₃OOCCH₂ | H | NOCH₃ | | | |
| 70 | N≡CCH₂ | H | NOCH₃ | | | |
| 71 | H | CH₃ | NOCH₃ | a s | 136–138 127–130 | |
| 72 | CH₃ | CH₃ | NOCH₃ | s a | 80–81 oil | 6.68/7.46 |
| 73 | C₂H₅ | CH₃ | NOCH₃ | a(85) s(15) | oil | 6.60/6.82 6.69/7.46 |
| 74 | i-C₃H₇ | CH₃ | NOCH₃ | a | oil | 6.58/6.84 |
| 75 | t-C₄H₉ | CH₃ | NOCH₃ | | | |
| 76 | H₂C=CH—CH₂ | CH₃ | NOCH₃ | | | |
| 77 | H₂C=CCl—CH₂ | CH₃ | NOCH₃ | a s | oil oil | 6.64/6.82 6.72/7.51 |
| 78 | CH₃CCl=CH—CH₂ | CH₃ | NOCH₃ | a | oil | 6.61/6.81 |
| 79 | H—C≡C—CH₂ | CH₃ | NOCH₃ | | | |
| 80 | Cyclopropyl | CH₃ | NOCH₃ | | | |
| 81 | C₆H₅ | CH₃ | NCCH₃ | | | |
| 82 | 4-Pyridyl | CH₃ | NOCH₃ | | | |
| 83 | C₆H₅CH₂ | CH₃ | NOCH₃ | a | oil | 6.62/6.82 |
| 84 | 2-Pyridylmethyl | CH₃ | NOCH₃ | | | |
| 85 | 5-Chlorothien-2-ylmethyl | CH₃ | NOCH₃ | a | oil | 6.63/6.81 |
| 86 | CH₃CO | CH₃ | NOCH₃ | | | |
| 87 | C₆H₅CO | CH₃ | NOCH₃ | | | |
| 88 | 2-Furyl-CO | CH₃ | NOCH₃ | | | |
| 89 | CH₃OOCCH₂ | CH₃ | NOCH₃ | a | oil | 6.65/6.80 |
| 90 | N≡CCH₂ | CH₃ | NOCH₃ | a | 81–85 | |
| 91 | H | C₆H₅ | NOCH₃ | a(70) s(30) | 164–165 | |
| 92 | CH₃ | C₆H₅ | NOCH₃ | a | 175–179 | |
| 93 | C₆H₅CH₂ | C₆H₅ | NOCH₃ | | | |
| 94 | H₂C=CCl—CH₂ | C₆H₅ | NOCH₃ | | | |
| 95 | N≡C—CH₂ | C₆H₅ | NOCH₃ | | | |
| 96 | H | p-CH₃OC₆H₄ | NOCH₃ | | | |
| 97 | CH₃ | p-CH₃OC₆H₄ | NOCH₃ | a(40) s(60) | 100–104 | |
| 98 | C₆H₅CH₂ | p-CH₃OC₆H₄ | NOCH₃ | | | |
| 99 | H₂C=CCl—CH₂ | p-CH₃OC₆H₄ | NOCH₃ | | | |
| 100 | N≡C—CH₂ | p-CH₃OC₆H₄ | NOCH₃ | | | |
| 101 | H | H | CHCH₃ | | | |
| 102 | CH₃ | H | CHCH₃ | | | |
| 103 | C₂H₅ | H | CHCH₃ | | | |
| 104 | i-C₃H₇ | H | CHCH₃ | | | |
| 105 | t-C₄H₉ | H | CHCH₃ | | | |
| 106 | H₂C=CH—CH₂ | H | CHCH₃ | | | |
| 107 | H₂C=CCl—CH₂ | H | CHCH₃ | | | |
| 108 | CH₃—CCl=CH—CH₂ | H | CHCH₃ | | | |
| 109 | H—C≡C—CH₂ | H | CHCH₃ | | | |
| 110 | Cyclopropyl | H | CHCH₃ | | | |
| 111 | C₆H₅ | H | CHCH₃ | | | |
| 112 | 4-Pyridyl | H | CHCH₃ | | | |
| 113 | C₆H₅CH₂ | H | CHCH₃ | | | |
| 114 | 2-Pyridylmethyl | H | CHCH₃ | | | |
| 115 | 5-Chlorothien-2-ylmethyl | H | CHCH₃ | | | |
| 116 | CH₃CO | H | CHCH₃ | | | |
| 117 | C₆H₅CO | H | CHCH₃ | | | |
| 118 | 2-Furyl-CO | H | CHCH₃ | | | |

TABLE VI-continued

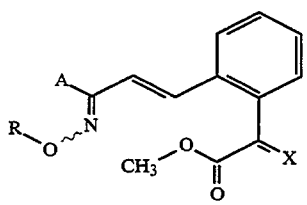

| No. | R | A | X | Isomer | m.p. (°C.) | δ(C=CH) |
|---|---|---|---|---|---|---|
| 119 | CH$_3$OOCCH$_2$ | H | CHCH$_3$ | | | |
| 120 | N≡CCH$_2$ | H | CHCH$_3$ | | | |
| 121 | H | CH$_3$ | CHCH$_3$ | | | |
| 122 | CH$_3$ | CH$_3$ | CHCH$_3$ | | | |
| 123 | C$_2$H$_5$ | CH$_3$ | CHCH$_3$ | | | |
| 124 | i-C$_3$H$_7$ | CH$_3$ | CHCH$_3$ | | | |
| 125 | t-C$_4$H$_9$ | CH$_3$ | CHCH$_3$ | | | |
| 126 | H$_2$C=CH—CH$_2$ | CH$_3$ | CHCH$_3$ | | | |
| 127 | H$_2$C=CCl—CH$_2$ | CH$_3$ | CHCH$_3$ | | | |
| 128 | CH$_3$CCl=CH—CH$_2$ | CH$_3$ | CHCH$_3$ | | | |
| 129 | H—C≡C—CH$_2$ | CH$_3$ | CHCH$_3$ | | | |
| 130 | Cyclopropyl | CH$_3$ | CHCH$_3$ | | | |
| 131 | C$_6$H$_5$ | CH$_3$ | CHCH$_3$ | | | |
| 132 | 4-Pyridyl | CH$_3$ | CHCH$_3$ | | | |
| 133 | C$_6$H$_5$CH$_2$ | CH$_3$ | CHCH$_3$ | | | |
| 134 | 2-Pyridylmethyl | CH$_3$ | CHCH$_3$ | | | |
| 135 | 5-Chlorothien-2-ylmethyl | CH$_3$ | CHCH$_3$ | | | |
| 136 | CH$_3$CO | CH$_3$ | CHCH$_3$ | | | |
| 137 | C$_6$H$_5$CO | CH$_3$ | CHCH$_3$ | | | |
| 138 | 2-Furyl-CO | CH$_3$ | CHCH$_3$ | | | |
| 139 | CH$_3$OOCCH$_2$ | CH$_3$ | CHCH$_3$ | | | |
| 140 | N≡CCH$_2$ | CH$_3$ | CHCH$_3$ | | | |
| 141 | H | C$_6$H$_5$ | CHCH$_3$ | | | |
| 142 | CH$_3$ | C$_6$H$_5$ | CHCH$_3$ | | | |
| 143 | C$_6$H$_5$CH$_2$ | C$_6$H$_5$ | CHCH$_3$ | | | |
| 144 | H$_2$C=CCl—CH$_2$ | C$_6$H$_5$ | CHCH$_3$ | | | |
| 145 | N≡C—CH$_2$ | C$_6$H$_5$ | CHCH$_3$ | | | |
| 146 | H | p-CH$_3$OC$_6$H$_4$ | CHCH$_3$ | | | |
| 147 | CH$_3$ | p-CH$_3$OC$_6$H$_4$ | CHCH$_3$ | | | |
| 148 | C$_6$H$_5$CH$_2$ | p-CH$_3$OC$_6$H$_4$ | CHCH$_3$ | | | |
| 149 | H$_2$C=CCl—CH$_2$ | p-CH$_3$OC$_6$H$_4$ | CHCH$_3$ | | | |
| 150 | N≡C—CH$_2$ | p-CH$_3$OC$_6$H$_4$ | CHCH$_3$ | | | |
| 151 | H | H | CHC$_2$H$_5$ | | | |
| 152 | CH$_3$ | H | CHC$_2$H$_5$ | | | |
| 153 | C$_2$H$_5$ | H | CHC$_2$H$_5$ | | | |
| 154 | i-C$_3$H$_7$ | H | CHC$_2$H$_5$ | | | |
| 155 | t-C$_4$H$_9$ | H | CHC$_2$H$_5$ | | | |
| 156 | H$_2$C=CH—CH$_2$ | H | CHC$_2$H$_5$ | | | |
| 157 | H$_2$C=CCl—CH$_2$ | H | CHC$_2$H$_5$ | | | |
| 158 | CH$_3$—CCl=CH—CH$_2$ | H | CHC$_2$H$_5$ | | | |
| 159 | H—C≡C—CH$_2$ | H | CHC$_2$H$_5$ | | | |
| 160 | Cyclopropyl | H | CHC$_2$H$_5$ | | | |
| 161 | C$_6$H$_5$ | H | CHC$_2$H$_5$ | | | |
| 162 | 4-Pyridyl | H | CHC$_2$H$_5$ | | | |
| 163 | C$_6$H$_5$CH$_2$ | H | CHC$_2$H$_5$ | | | |
| 164 | 2-Pyridylmethyl | H | CHC$_2$H$_5$ | | | |
| 165 | 5-Chlorothien-2-ylmethyl | H | CHC$_2$H$_5$ | | | |
| 166 | CH$_3$CO | H | CHC$_2$H$_5$ | | | |
| 167 | C$_6$H$_5$CO | H | CHC$_2$H$_5$ | | | |
| 168 | 2-Furyl-CO | H | CHC$_2$H$_5$ | | | |
| 169 | CH$_3$OOCCH$_2$ | H | CHC$_2$H$_5$ | | | |
| 170 | N≡CCH$_2$ | H | CHC$_2$H$_5$ | | | |
| 171 | H | CH$_3$ | CHC$_2$H$_5$ | | | |
| 172 | CH$_3$ | CH$_3$ | CHC$_2$H$_5$ | | | |
| 173 | C$_2$H$_5$ | CH$_3$ | CHC$_2$H$_5$ | | | |
| 174 | i-C$_3$H$_7$ | CH$_3$ | CHC$_2$H$_5$ | | | |
| 175 | t-C$_4$H$_9$ | CH$_3$ | CHC$_2$H$_5$ | | | |
| 176 | H$_2$C=CH—CH$_2$ | CH$_3$ | CHC$_2$H$_5$ | | | |
| 177 | H$_2$C=CCl—CH$_2$ | CH$_3$ | CHC$_2$H$_5$ | | | |
| 178 | CH$_3$CCl=CH—CH$_2$ | CH$_3$ | CHC$_2$H$_5$ | | | |
| 179 | H—C≡C—CH$_2$ | CH$_3$ | CHC$_2$H$_5$ | | | |
| 180 | Cyclopropyl | CH$_3$ | CHC$_2$H$_5$ | | | |
| 181 | C$_6$H$_5$ | CH$_3$ | CHC$_2$H$_5$ | | | |
| 182 | 4-Pyridyl | CH$_3$ | CHC$_2$H$_5$ | | | |
| 183 | C$_6$H$_5$CH$_2$ | CH$_3$ | CHC$_2$H$_5$ | | | |
| 184 | 2-Pyridylmethyl | CH$_3$ | CHC$_2$H$_5$ | | | |
| 185 | 5-Chlorothien- | CH$_3$ | CHC$_2$H$_5$ | | | |

TABLE VI-continued

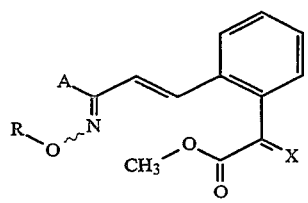

| No. | R | A | X | Isomer | m.p. (°C.) | δ(C=CH) |
|---|---|---|---|---|---|---|
| | 2-ylmethyl | | | | | |
| 186 | CH₃CO | CH₃ | CHC₂H₅ | | | |
| 187 | C₆H₅CO | CH₃ | CHC₂H₅ | | | |
| 188 | 2-Furyl—CO | CH₃ | CHC₂H₅ | | | |
| 189 | CH₃OOCCH₂ | CH₃ | CHC₂H₅ | | | |
| 190 | N=CCH₂ | CH₃ | CHC₂H₅ | | | |
| 191 | H | C₆H₅ | CHC₂H₅ | | | |
| 192 | CH₃ | C₆H₅ | CHC₂H₅ | | | |
| 193 | C₆H₅CH₂ | C₆H₅ | CHC₂H₅ | | | |
| 194 | H₂C=CCl—CH₂ | C₆H₅ | CHC₂H₅ | | | |
| 195 | N≡C—CH₂ | C₆H₅ | CHC₂H₅ | | | |
| 196 | H | p-CH₃OC₆H₄ | CHC₂H₅ | | | |
| 197 | CH₃ | p-CH₃OC₆H₄ | CHC₂H₅ | | | |
| 198 | C₆H₅CH₂ | p-CH₃OC₆H₄ | CHC₂H₅ | | | |
| 199 | H₂C=CCl—CH₂ | p-CH₃OC₆H₄ | CHC₂H₅ | | | |
| 200 | N≡C—CH₂ | p-CH₃OC₆H₄ | CHC₂H₅ | | | |
| 201 | n-C₄H₉ | CH₃ | CHOCH₃ | a(90) s(10) | oil | both 6.80 6.84/7.43 |
| 202 | 2-Methylallyl | CH₃ | CHOCH₃ | a(80) s(20) | oil | both 6.81 6.92/7.50 |
| 203 | 2-Bromoallyl | CH₃ | CHOCH₃ | a(75) s(25) | oil | 6.75/6.87 6.92/7.47 |
| 204 | 2-Isopropyl-6-hydroxy-pyrimidin-4-yl | CH₃ | CHOCH₃ | a(70) s(30) | 164–166 | |
| 205 | CH₃ | t-C₄H₉ | CHOCH₃ | | | |
| 206 | C₂H₅ | t-C₄H₉ | CHOCH₃ | | | |
| 207 | i-C₃H₇ | t-C₄H₉ | CHOCH₃ | | | |
| 208 | t-C₄H₉ | t-C₄H₉ | CHOCH₃ | | | |
| 209 | 2-Chloroallyl | t-C₄H₉ | CHOCH₃ | | | |
| 210 | Benzyl | t-C₄H₉ | CHOCH₃ | | | |
| 211 | CH₃ | CH₃O | CHOCH₃ | | | |
| 212 | t-C₄H₉ | CH₃O | CHOCH₃ | | | |
| 213 | 2-Chloroallyl | CH₃O | CHOCH₃ | | | |
| 214 | Benzyl | CH₃O | CHOCH₃ | | | |
| 215 | n-C₄H₉ | CH₃ | NOCH₃ | | | |
| 216 | 2-Methylallyl | CH₃ | NOCH₃ | a(80) s(20) | oil | 6.62/6.83 6.70/7.50 |
| 217 | 2-Bromoallyl | CH₃ | NOCH₃ | a(85) s(15) | oil | 6.64/6.80 6.78/7.51 |
| 218 | 2-Isopropyl-6-hydroxy-pyrimidin-4-yl | CH₃ | NOCH₃ | a(70) s(30) | 176–178 | |
| 219 | CH₃ | t-C₄H₉ | NOCH₃ | s | 84–86 | |
| 220 | C₂H₅ | t-C₄H₉ | NOCH₃ | | | |
| 221 | i-C₃H₇ | t-C₄H₉ | NOCH₃ | s | | 6.59/7.40 |
| 222 | t-C₄H₉ | t-C₄H₉ | NOCH₃ | s | oil | 6.60/7.49 |
| 223 | 2-Chloroallyl | t-C₄H₉ | NOCH₃ | s | oil | 6.60/7.22 |
| 224 | Benzyl | t-C₄H₉ | NOCH₃ | | | |
| 225 | CH₃ | CH₃O | NOCH₃ | | | |
| 226 | t-C₄H₉ | CH₃O | NOCH₃ | | | |
| 227 | 2-Chloroallyl | CH₃O | NOCH₃ | | | |
| 228 | Benzyl | CH₃O | NOCH₃ | | | |

TABLE VII

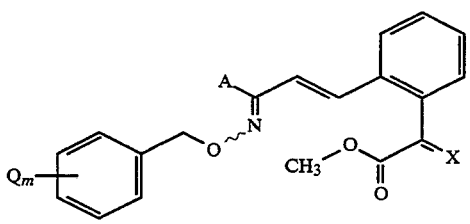

| No. | $Q_m$ | A | X | Isomer | m.p. (°C.) | δ (C=C$\underline{H}$) |
|---|---|---|---|---|---|---|
| 1 | 3-F | H | CHOCH$_3$ | | | |
| 2 | 2,6-F$_2$ | H | CHOCH$_3$ | | | |
| 3 | 2-Cl | H | CHOCH$_3$ | | | |
| 4 | 3-Cl | H | CHOCH$_3$ | | | |
| 5 | 4-Cl | H | CHOCH$_3$ | | | |
| 6 | 2,6-Cl$_2$ | H | CHOCH$_3$ | | | |
| 7 | 3,4-Cl$_2$ | H | CHOCH$_3$ | | | |
| 8 | 3-Br | H | CHOCH$_3$ | | | |
| 9 | 4-I | H | CHOCH$_3$ | | | |
| 10 | 2-Cl, 6-F | H | CHOCH$_3$ | | | |
| 11 | 2-CH$_3$ | H | CHOCH$_3$ | | | |
| 12 | 3-CH$_3$ | H | CHOCH$_3$ | | | |
| 13 | 4-CH$_3$ | H | CHOCH$_3$ | | | |
| 14 | 2,4-(CH$_3$)$_2$ | H | CHOCH$_3$ | | | |
| 15 | 4,6-(CH$_3$)$_3$ | H | CHOCH$_3$ | | | |
| 16 | 3-C$_2$H$_5$ | H | CHOCH$_3$ | | | |
| 17 | 4-t-C$_4$H$_9$ | H | CHOCH$_3$ | | | |
| 18 | 4-Cyclohexyl | H | CHOCH$_3$ | | | |
| 19 | 3-CH$_2$C$_6$H$_5$ | H | CHOCH$_3$ | | | |
| 20 | 2-OCH$_3$ | H | CHOCH$_3$ | | | |
| 21 | 3-OCH$_3$ | H | CHOCH$_3$ | | | |
| 22 | 4-OCH$_3$ | H | CHOCH$_3$ | | | |
| 23 | 2-O-i-C3H7 | H | CHOCH$_3$ | | | |
| 24 | 3-OCH$_2$C$_6$H$_5$ | H | CHOCH$_3$ | | | |
| 25 | 3-CF$_3$ | H | CHOCH$_3$ | | | |
| 26 | 3-NO$_2$ | H | CHOCH$_3$ | | | |
| 27 | 4-NO$_2$ | H | CHOCH$_3$ | | | |
| 28 | 3-Cyano | H | CHOCH$_3$ | | | |
| 29 | 2-Cl, 4-CH$_3$ | H | CHOCH$_3$ | | | |
| 30 | 2-COOCH$_3$ | H | CHOCH$_3$ | | | |
| 31 | 4-CH$_2$OCH$_3$ | H | CHOCH$_3$ | | | |
| 32 | 4-COCH$_3$ | H | CHOCH$_3$ | | | |
| 33 | 2-CH$_3$-4-COCH$_3$ | H | CHOCH$_3$ | | | |
| 34 | 4-C(CH$_3$)=NOCH$_2$CH=CH$_2$ | H | CHOCH$_3$ | | | |
| 35 | 2-CH$_3$-4-C(CH$_3$)=NOCH$_2$CH=CH$_2$ | H | CHOCH$_3$ | | | |
| 36 | 3-F | CH$_3$ | CHOCH$_3$ | a | oil | 6.77/6.83 |
| 37 | 2,6-F$_2$ | CH$_3$ | CHOCH$_3$ | a | 116–118 | |
| | | | | s | 180–82 | |
| 38 | 2-Cl | CH$_3$ | CHOCH$_3$ | | | |
| 39 | 3-Cl | CH$_3$ | CHOCH$_3$ | | | |
| 40 | 4-Cl | CH$_3$ | CHOCH$_3$ | | | |
| 41 | 2,6-Cl$_2$ | CH$_3$ | CHOCH$_3$ | a | 131–133 | |
| | | | | s | oil | 6.85/7.38 |
| 42 | 3,4-Cl$_2$ | CH$_3$ | CHOCH$_3$ | a | oil | 6.74/6.87 |
| 43 | 3-Br | CH$_3$ | CHOCH$_3$ | a | oil | 6.75/6.85 |
| 44 | 4-I | CH$_3$ | CHOCH$_3$ | | | |
| 45 | 2-Cl, 6-F | CH$_3$ | CHOCH$_3$ | | | |
| 46 | 2-CH$_3$ | CH$_3$ | CHOCH$_3$ | a | oil | both 6.82 |
| 47 | 3-CH$_3$ | CH$_3$ | CHOCH$_3$ | a(75) | oil | both 6.81 |
| | | | | s(25) | | 6.89/7.48 |
| 48 | 4-CH$_3$ | CH$_3$ | CHOCH$_3$ | a | oil | both 6.78 |
| 49 | 2,4-(CH$_3$)$_2$ | CH$_3$ | CHOCH$_3$ | | | |
| 50 | 2,4,6-(CH$_3$)$_3$ | CH$_3$ | CHOCH$_3$ | | | |
| 51 | 3-C$_2$H$_5$ | CH$_3$ | CHOCH$_3$ | | | |
| 52 | 4-t-C$_4$H$_9$ | CH$_3$ | CHOCH$_3$ | | | |
| 53 | 4-Cyclohexyl | CH$_3$ | CHOCH$_3$ | | | |
| 54 | 3-CH$_2$C$_6$H$_5$ | CH$_3$ | CHOCH$_3$ | | | |
| 55 | 2-OCH$_3$ | CH$_3$ | CHOCH$_3$ | | | |
| 56 | 3-OCH$_3$ | CH$_3$ | CHOCH$_3$ | | | |
| 57 | 4-OCH$_3$ | CH$_3$ | CHOCH$_3$ | | | |
| 58 | 2-O-i-C$_3$H$_7$ | CH$_3$ | CHOCH$_3$ | | | |
| 59 | 3-OCH$_2$C$_6$H$_5$ | CH$_3$ | CHOCH$_3$ | | | |
| 60 | 2-CF$_3$ | CH$_3$ | CHOCH$_3$ | a | oil | 6.76/6.86 |
| 61 | 3-NO$_2$ | CH$_3$ | CHOCH$_3$ | | | |
| 62 | 4-NO$_2$ | CH$_3$ | CHOCH$_3$ | | | |
| 63 | 3-Cyano | CH$_3$ | CHOCH$_3$ | a | oil | 6.73/6.84 |
| 64 | 2-Cl, 4-CH$_3$ | CH$_3$ | CHOCH$_3$ | | | |

TABLE VII-continued

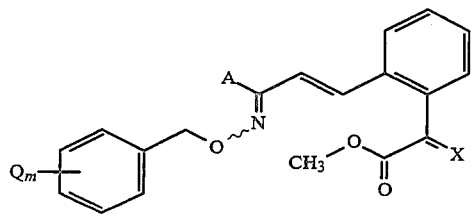

| No. | $Q_m$ | A | X | Isomer | m.p. (°C.) | δ (C=CH) |
|---|---|---|---|---|---|---|
| 65 | 2-COOCH$_3$ | CH$_3$ | CHOCH$_3$ | | | |
| 66 | 4-CH$_2$OCH$_3$ | CH$_3$ | CHOCH$_3$ | | | |
| 67 | 4-COCH$_3$ | CH$_3$ | CHOCH$_3$ | | | |
| 68 | 2-CH$_3$-4-OCH$_3$ | CH$_3$ | CHOCH$_3$ | | | |
| 69 | 4-C(CH$_3$)=NOCH$_2$CH=CH$_2$ | CH$_3$ | CHOCH$_3$ | | | |
| 70 | 2-CH$_3$-4-C(CH$_3$)=NOCH$_2$CH=CH$_2$ | CH$_3$ | CHOCH$_3$ | | | |
| 71 | 3-F | H | NOCH$_3$ | a | 83–85 | |
| 72 | 2,6-F$_2$ | H | NOCH$_3$ | a | 120–122 | |
| 73 | 2-Cl | H | NOCH$_3$ | | | |
| 74 | 3-Cl | H | NOCH$_3$ | | | |
| 75 | 4-Cl | H | NOCH$_3$ | | | |
| 76 | 2,6-Cl$_2$ | H | NOCH$_3$ | a(80) s(20) | 127–129 | |
| 77 | 3,4-Cl$_2$ | H | NOCH$_3$ | a | oil | 6.57/6.78 |
| 78 | 3-Br | H | NOCH$_3$ | a | 126–128 | |
| 79 | 4-I | H | NOCH$_3$ | | | |
| 80 | 2-Cl, 6-F | H | NOCH$_3$ | | | |
| 81 | 2-CH$_3$ | H | NOCH$_3$ | | | |
| 82 | 3-CH$_3$ | H | NOCH$_3$ | | | |
| 83 | 4-CH$_3$ | H | NOCH$_3$ | a | oil | 6.62/6.82 |
| 84 | 2,4-(CH$_3$)$_2$ | H | NOCH$_3$ | | | |
| 85 | 2,4,6-(CH$_3$)$_3$ | H | NOCH$_3$ | | | |
| 86 | 3-C$_2$H$_5$ | H | NOCH$_3$ | | | |
| 87 | 4-t-C$_4$H$_9$ | H | NOCH$_3$ | | | |
| 88 | 4-Cyclohexyl | H | NOCH$_3$ | | | |
| 89 | 3-CH$_2$C$_6$H$_5$ | H | NOCH$_3$ | | | |
| 90 | 2-OCH$_3$ | H | NOCH$_3$ | | | |
| 91 | 3-OCH$_3$ | H | NOCH$_3$ | | | |
| 92 | 4-OCH$_3$ | H | NOCH$_3$ | | | |
| 93 | 2-O-i-C$_3$H$_7$ | H | NOCH$_3$ | | | |
| 94 | 3-OCH$_2$C$_6$H$_5$ | H | NOCH$_3$ | | | |
| 95 | 3-CF$_3$ | H | NOCH$_3$ | a(80) s(20) | 63–66 | |
| 96 | 3-NO$_2$ | H | NOCH$_3$ | | | |
| 97 | 4-NO$_2$ | H | NOCH$_3$ | | | |
| 98 | 3-Cyano | H | NOCH$_3$ | a | oil | 6.58/6.78 |
| 99 | 2-Cl, 4-CH$_3$ | H | NOCH$_3$ | | | |
| 100 | 2-COOCH$_3$ | H | NOCH$_3$ | | | |
| 101 | 4-CH$_2$OCH$_3$ | H | NOCH$_3$ | | | |
| 102 | 4-COCH$_3$ | H | NOCH$_3$ | | | |
| 103 | 2-CH$_3$-4-COCH$_3$ | H | NOCH$_3$ | | | |
| 104 | 4-C(CH$_3$)=NOCH$_2$CH=CH$_2$ | H | NOCH$_3$ | | | |
| 105 | 2-CH$_3$-4-C(CH$_3$)=NOCH$_3$CH=CH$_2$ | H | NOCH$_3$ | | | |
| 106 | 3-F | CH$_3$ | NOCH$_3$ | a | oil | 6.62/6.80 |
| 107 | 2,6-F$_2$ | CH$_3$ | NOCH$_3$ | a | 82–83 (Zers.) | |
| 108 | 2-Cl | CH$_3$ | NOCH$_3$ | | | |
| 109 | 3-Cl | CH$_3$ | NOCH$_3$ | | | |
| 110 | 4-Cl | CH$_3$ | NOCH$_3$ | | | |
| 111 | 2,6-Cl$_2$ | CH$_3$ | NOCH$_3$ | a | 126–128 | |
| 112 | 3,4-Cl$_2$ | CH$_3$ | NOCH$_3$ | a | oil | 6.62/6.78 |
| 113 | 3-Br | CH$_3$ | NOCH$_3$ | a | oil | 6.63/6.82 |
| 114 | 4-I | CH$_3$ | NOCH$_3$ | | | |
| 115 | 2-Cl, 6-F | CH$_3$ | NOCH$_3$ | | | |
| 116 | 2-CH$_3$ | CH$_3$ | NOCH$_3$ | a | oil | 6.62/6.83 |
| 117 | 3-CH$_3$ | CH$_3$ | NOCH$_3$ | a(80) s(20) | oil | 6.60/6.82 6.75/7.49 |
| 118 | 4-CH$_3$ | CH$_3$ | NOCH$_3$ | | | |
| 119 | 2,4-(CH$_3$)$_2$ | CH$_3$ | NOCH$_3$ | | | |
| 120 | 2,4,6-(CH$_3$)$_3$ | CH$_3$ | NOCH$_3$ | | | |
| 121 | 3-C$_2$H$_5$ | CH$_3$ | NOCH$_3$ | | | |
| 122 | 4-t-C$_4$H$_9$ | CH$_3$ | NOCH$_3$ | | | |
| 123 | 4-Cyclohexyl | CH$_3$ | NOCH$_3$ | | | |
| 124 | 3-CH$_2$C$_6$H$_5$ | CH$_3$ | NOCH$_3$ | | | |
| 125 | 2-OCH$_3$ | CH$_3$ | NOCH$_3$ | | | |
| 126 | 3-OCH$_3$ | CH$_3$ | NOCH$_3$ | | | |

TABLE VII-continued

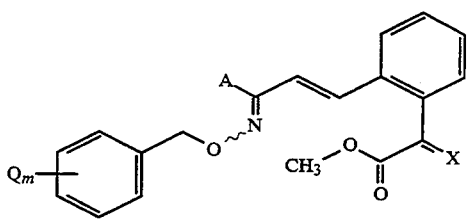

| No. | $Q_m$ | A | X | Isomer | m.p. (°C.) | δ (C=CH) |
|---|---|---|---|---|---|---|
| 127 | 4-OCH$_3$ | CH$_3$ | NOCH$_3$ | | | |
| 128 | 2-O-i-C$_3$H$_7$ | CH$_3$ | NOCH$_3$ | | | |
| 129 | OCH$_2$C$_6$H$_5$ | CH$_3$ | NOCH$_3$ | | | |
| 130 | 3-CF$_3$ | CH$_3$ | NOCH$_3$ | a | oil | 6.64/6.79 |
| 131 | 3-NO$_2$ | CH$_3$ | NOCH$_3$ | | | |
| 132 | 4-NO$_2$ | CH$_3$ | NOCH$_3$ | | oil | 6.65/6.79 |
| 133 | 3-Cyano | CH$_3$ | NOCH$_3$ | | oil | 6.64/6.79 |
| 134 | 2-Cl, 4-CH$_3$ | CH$_3$ | NOCH$_3$ | | | |
| 135 | 2-COOCH$_3$ | CH$_3$ | NOCH$_3$ | | | |
| 136 | 4-CH$_2$OCH$_3$ | CH$_3$ | NOCH$_3$ | | | |
| 137 | 4-COCH$_3$ | CH$_3$ | NOCH$_3$ | | | |
| 138 | 2-CH$_3$-4-COCH$_3$ | CH$_3$ | NOCH$_3$ | | | |
| 139 | 4-C(CH$_3$)=NOCH$_2$CH=CH$_2$ | CH$_3$ | NOCH$_3$ | | | |
| 140 | 2-CH$_3$-4-C(CH$_3$)=NOCH$_2$CH=CH$_2$ | CH$_3$ | NOCH$_3$ | | | |
| 141 | 3-F | H | CHCH$_3$ | | | |
| 142 | 2,6-F$_2$ | H | CHCH$_3$ | | | |
| 143 | 2-Cl | H | CHCH$_3$ | | | |
| 144 | 3-Cl | H | CHCH$_3$ | | | |
| 145 | 4-Cl | H | CHCH$_3$ | | | |
| 146 | 2,6-Cl$_2$ | H | CHCH$_3$ | | | |
| 147 | 3,4-Cl$_2$ | H | CHCH$_3$ | | | |
| 148 | 3-Br | H | CHCH$_3$ | | | |
| 149 | 4-I | H | CHCH$_3$ | | | |
| 150 | 2-Cl, 6-F | H | CHCH$_3$ | | | |
| 151 | 2-CH$_3$ | H | CHCH$_3$ | | | |
| 152 | 3-CH$_3$ | H | CHCH$_3$ | | | |
| 153 | 4-CH$_3$ | H | CHCH$_3$ | | | |
| 154 | 2,4-(CH$_3$) | H | CHCH$_3$ | | | |
| 155 | 2,4,6-(CH$_3$)$_3$ | H | CHCH$_3$ | | | |
| 156 | 3-C$_2$H$_5$ | H | CHCH$_3$ | | | |
| 157 | 4-t-C$_4$H$_9$ | H | CHCH$_3$ | | | |
| 158 | 4-Cyclohexyl | H | CHCH$_3$ | | | |
| 159 | 3-CH$_2$C$_6$H$_5$ | H | CHCH$_3$ | | | |
| 160 | 2-OCH$_3$ | H | CHCH$_3$ | | | |
| 161 | 3-OCH$_3$ | H | CHCH$_3$ | | | |
| 162 | 4-OCH$_3$ | H | CHCH$_3$ | | | |
| 163 | 2-O-i-C$_3$H$_7$ | H | CHCH$_3$ | | | |
| 164 | 3-OCH$_2$C$_6$H$_5$ | H | CHCH$_3$ | | | |
| 165 | 3-CF$_3$ | H | CHCH$_3$ | | | |
| 166 | 3-NO$_2$ | H | CHCH$_3$ | | | |
| 167 | 4-NO$_2$ | H | CHCH$_3$ | | | |
| 168 | 3-Cyano | H | CHCH$_3$ | | | |
| 169 | 2-Cl, 4-CH$_3$ | H | CHCH$_3$ | | | |
| 170 | 2-COOCH$_3$ | H | CHCH$_3$ | | | |
| 171 | 4-CH$_2$CCH$_3$ | H | CHCH$_3$ | | | |
| 172 | 4-COCH$_3$ | H | CHCH$_3$ | | | |
| 173 | 2-CH$_3$-4-COCH$_3$ | H | CHCH$_3$ | | | |
| 174 | 4-C(CH$_3$)=NOCH$_2$CH=CH$_2$ | H | CHCH$_3$ | | | |
| 175 | 2-CH$_3$-4-C(CH$_3$)=NOCH$_2$CH=CH$_2$ | H | CHCH$_3$ | | | |
| 176 | 3-F | CH$_3$ | CHCH$_3$ | | | |
| 177 | 2,6-F$_2$ | CH$_3$ | CHCH$_3$ | | | |
| 178 | 2-Cl | CH$_3$ | CHCH$_3$ | | | |
| 179 | 3-Cl | CH$_3$ | CHCH$_3$ | | | |
| 180 | 4-Cl | CH$_3$ | CHCH$_3$ | | | |
| 181 | 2,6-Cl$_2$ | CH$_3$ | CHCH$_3$ | | | |
| 182 | 3,4-Cl$_2$ | CH$_3$ | CHCH$_3$ | | | |
| 183 | 3-Br | CH$_3$ | CHCH$_3$ | | | |
| 184 | 4-I | CH$_3$ | CHCH$_3$ | | | |
| 185 | 2-Cl, 6-F | CH$_3$ | CHCH$_3$ | | | |
| 186 | 2-CH$_3$ | CH$_3$ | CHCH$_3$ | | | |
| 187 | 3-CH$_3$ | CH$_3$ | CHCH$_3$ | | | |
| 188 | 4-CH$_3$ | CH$_3$ | CHCH$_3$ | | | |
| 189 | 2,4-(CH$_3$)$_2$ | CH$_3$ | CHCH$_3$ | | | |
| 190 | 2,4,6-(CH$_3$)$_3$ | CH$_3$ | CHCH$_3$ | | | |
| 191 | 3-C$_2$H$_5$ | CH$_3$ | CHCH$_3$ | | | |
| 192 | 4-t-C$_4$H$_9$ | CH$_3$ | CHCH$_3$ | | | |

TABLE VII-continued

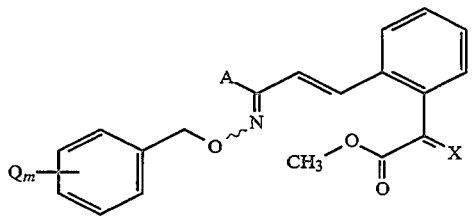

| No. | $Q_m$ | A | X | Isomer | m.p. (°C.) | δ (C=CH) |
|---|---|---|---|---|---|---|
| 193 | 4-Cyclohexyl | CH₃ | CHCH₃ | | | |
| 194 | 3-CH₂C₆H₅ | CH₃ | CHCH₃ | | | |
| 195 | 2-OCH₃ | CH₃ | CHCH₃ | | | |
| 196 | 3-OCH₃ | CH₃ | CHCH₃ | | | |
| 197 | 4-OCH₃ | CH₃ | CHCH₃ | | | |
| 198 | 2-O-i-C₃H₇ | CH₃ | CHCH₃ | | | |
| 199 | 3-OCH₂C₆H₅ | CH₃ | CHCH₃ | | | |
| 200 | 3-CF₃ | CH₃ | CHCH₃ | | | |
| 201 | 3-NO₂ | CH₃ | CHCH₃ | | | |
| 202 | 4-NO₂ | CH₃ | CHCH₃ | | | |
| 203 | 3-Cyano | CH₃ | CHCH₃ | | | |
| 204 | 2-Cl, 4-CH₃ | CH₃ | CHCH₃ | | | |
| 205 | 2-COOCH₃ | CH₃ | CHCH₃ | | | |
| 206 | 4-CH₂OCH₃ | CH₃ | CHCH₃ | | | |
| 207 | 4-COCH₃ | CH₃ | CHCH₃ | | | |
| 208 | 2-CH₃-4-COCH₃ | CH₃ | CHCH₃ | | | |
| 209 | 4-C(CH₃)=NOCH₂CH=CH₂ | CH₃ | CHCH₃ | | | |
| 210 | 2-CH₃-4-C(CH₃)=NOCH₂CH=CH₂ | CH₃ | CHCH₃ | | | |
| 211 | 3-F | H | CHC₂H₅ | | | |
| 212 | 2,6-F₂ | H | CHC₂H₅ | | | |
| 213 | 2-Cl | H | CHC₂H₅ | | | |
| 214 | 3-Cl | H | CHC₂H₅ | | | |
| 215 | 4-Cl | H | CHC₂H₅ | | | |
| 216 | 2,6-Cl₂ | H | CHC₂H₅ | | | |
| 217 | 3,4-Cl₂ | H | CHC₂H₅ | | | |
| 218 | 3-Br | H | CHC₂H₅ | | | |
| 219 | 4-I | H | CHC₂H₅ | | | |
| 220 | 2-Cl, 6-F | H | CHC₂H₅ | | | |
| 221 | 2-CH₃ | H | CHC₂H₅ | | | |
| 222 | 3-CH₃ | H | CHC₂H₅ | | | |
| 223 | 4-CH₃ | H | CHC₂H₅ | | | |
| 224 | 2,4-(CH₃)₂ | H | CHC₂H₅ | | | |
| 225 | 2,4,6-(CH₃)₃ | H | CHC₂H₅ | | | |
| 226 | 3-C₂H₅ | H | CHC₂H₅ | | | |
| 227 | 4-t-C₄H₉ | H | CHC₂H₅ | | | |
| 228 | 4-Cyclohexyl | H | CHC₂H₅ | | | |
| 229 | 3-CH₂C₆H₅ | H | CHC₂H₅ | | | |
| 230 | 2-OCH₃ | H | CHC₂H₅ | | | |
| 231 | 3-OCH₃ | H | CHC₂H₅ | | | |
| 232 | 4-OCH₃ | H | CHC₂H₅ | | | |
| 233 | 2-O-i-C₃H₇ | H | CHC₂H₅ | | | |
| 234 | 3-OCH₂C₆H₅ | H | CHC₂H₅ | | | |
| 235 | 3-CF₃ | H | CHC₂H₅ | | | |
| 236 | 3-NO₂ | H | CHC₂H₅ | | | |
| 237 | 4-NO₂ | H | CHC₂H₅ | | | |
| 238 | 3-Cyano | H | CHC₂H₅ | | | |
| 239 | 2-Cl, 4-CH₃ | H | CH₃C₃H₅ | | | |
| 240 | 2-COOCH₃ | H | CHC₂H₅ | | | |
| 241 | 4-CH₂OCH₃ | H | CHC₂H₅ | | | |
| 242 | 4-COCH₃ | H | CHC₂H₅ | | | |
| 243 | 2-CH₃-4-COCH₃ | H | CHC₂H₅ | | | |
| 244 | 4-C(CH₃)=NOCH₂CH=CH₂ | H | CHC₂H₅ | | | |
| 245 | 2-CH₃-4-C(CH₃)=NOCH₂CH=CH₂ | H | CHC₂H₅ | | | |
| 246 | 3-F | CH₃ | CHC₂H₅ | | | |
| 247 | 2,6-F₂ | CH₃ | CHC₂H₅ | | | |
| 248 | 2-Cl | CH₃ | CHC₂H₅ | | | |
| 249 | 3-Cl | CH₃ | CHC₂H₅ | | | |
| 250 | 4-Cl | CH₃ | CHC₂H₅ | | | |
| 251 | 2,6-Cl₂ | CH₃ | CHC₂H₅ | | | |
| 252 | 3,4-Cl₂ | CH₃ | CHC₂H₅ | | | |
| 253 | 3-Br | CH₃ | CHC₂H₅ | | | |
| 254 | 4-I | CH₃ | CHC₂H₅ | | | |
| 255 | 2-Cl, 6-F | CH₃ | CHC₂H₅ | | | |
| 256 | 2-CH₃ | CH₃ | CHC₂H₅ | | | |
| 257 | 3-CH₃ | CH₃ | CHC₂H₅ | | | |
| 258 | 4-CH₃ | CH₃ | CHC₂H₅ | | | |

TABLE VII-continued

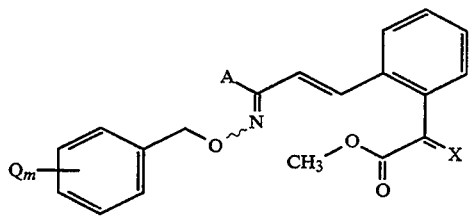

| No. | $Q_m$ | A | X | Isomer | m.p. (°C.) | δ (C=CH) |
|---|---|---|---|---|---|---|
| 259 | 2,4-(CH$_3$)$_2$ | CH$_3$ | CHC$_2$H$_5$ | | | |
| 260 | 2,4,6-(CH$_3$)$_3$ | CH$_3$ | CHC$_2$H$_5$ | | | |
| 261 | 3-C$_2$H$_5$ | CH$_3$ | CHC$_2$H$_5$ | | | |
| 262 | 4-t-C$_4$H$_9$ | CH$_3$ | CHC$_2$H$_5$ | | | |
| 263 | 4-Cyclohexyl | CH$_3$ | CHC$_2$H$_5$ | | | |
| 264 | 3-CH$_2$C$_6$H$_5$ | CH$_3$ | CHC$_2$H$_5$ | | | |
| 265 | 2-OCH$_3$ | CH$_3$ | CHC$_2$H$_5$ | | | |
| 266 | 3-OCH$_3$ | CH$_3$ | CHC$_2$H$_5$ | | | |
| 267 | 4-OCH$_3$ | CH$_3$ | CHC$_2$H$_5$ | | | |
| 268 | 2-O-i-C$_3$H$_7$ | CH$_3$ | CHC$_2$H$_5$ | | | |
| 269 | 3-OCH$_2$C$_6$H$_5$ | CH$_3$ | CHC$_2$H$_5$ | | | |
| 270 | 3-CF$_3$ | CH$_3$ | CHC$_2$H$_5$ | | | |
| 271 | 3-NO$_2$ | CH$_3$ | CHC$_2$H$_5$ | | | |
| 272 | 4-NO$_2$ | CH$_3$ | CHC$_2$H$_5$ | | | |
| 273 | 3-Cyano | CH$_3$ | CHC$_2$H$_5$ | | | |
| 274 | 2-Cl, 4-CH$_3$ | CH$_3$ | CHC$_2$H$_5$ | | | |
| 275 | 2-COOCH$_3$ | CH$_3$ | CHC$_2$H$_5$ | | | |
| 276 | 4-CH$_2$OCH$_3$ | CH$_3$ | CHC$_2$H$_5$ | | | |
| 277 | 4-COCH$_3$ | CH$_3$ | CHC$_2$H$_5$ | | | |
| 278 | 2-CH$_3$-4-COCH$_3$ | CH$_3$ | CHC$_2$H$_5$ | | | |
| 279 | 4-C(CH$_3$)=NOCH$_2$CH=CH$_2$ | CH$_3$ | CHC$_2$H$_5$ | | | |
| 280 | 2-CH$_3$-4-C(CH$_3$)=NOCH$_2$CH=CH$_2$ | CH$_3$ | | | | |
| 281 | 4-F | CH$_3$ | CHOCH$_3$ | a | oil | 6.76/6.83 |
| 282 | 2-OCH$_3$ | t-C$_4$H$_9$ | CHOCH$_3$ | | | |
| 283 | 3-F | t-C$_4$H$_9$ | CHOCH$_3$ | | | |
| 284 | 4-CH$_3$ | t-C$_4$H$_9$ | CHOCH$_3$ | | | |
| 285 | 3,5-Cl$_2$ | t-C$_4$H$_9$ | CHOCH$_3$ | | | |
| 286 | 2-OCH$_3$ | CH$_3$O | CHOCH$_3$ | | | |
| 287 | 3-CF$_3$ | CH$_3$O | CHOCH$_3$ | | | |
| 288 | 4-CH$_3$ | CH$_3$O | CHOCH$_3$ | | | |
| 289 | 3,5-Cl$_2$ | CH$_3$O | CHOCH$_3$ | | | |
| 290 | 4-F | CH$_3$ | NOCH$_3$ | a | oil | 6.62/6.80 |
| 291 | 2-OCH$_3$ | t-C$_4$H$_9$ | NOCH$_3$ | | | |
| 292 | 3-F | t-C$_4$H$_9$ | NOCH$_3$ | s | oil | 6.4/7.44 |
| 293 | 4-CH$_3$ | t-C$_4$H$_9$ | NOCH$_3$ | | | |
| 294 | 3,5-Cl$_2$ | t-C$_4$H$_9$ | NOCH$_3$ | | | |
| 295 | 2-OCH$_3$ | CH$_3$O | NOCH$_3$ | | | |
| 296 | 3-CF$_3$ | CH$_3$O | NOCH$_3$ | | | |
| 297 | 4-CH$_3$ | CH$_3$O | NOCH$_3$ | | | |
| 298 | 3,5-Cl$_2$ | CH$_3$O | NOCH$_3$ | | | |

TABLE VIII

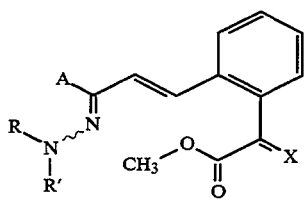

| No. | R | R' | A | X | Isomer | m.p. (°C.) | δ (C=CH) |
|---|---|---|---|---|---|---|---|
| 1 | H | H | H | CHOCH$_3$ | | | |
| 2 | CH$_3$ | H | H | CHOCH$_3$ | | | |
| 3 | t-C$_4$H$_9$ | H | H | CHOCH$_3$ | | | |
| 4 | C$_6$H$_5$ | H | H | CHOCH$_3$ | | | |
| 5 | 2-ClC$_6$H$_4$ | H | H | CHOCH$_3$ | | | |
| 6 | 3-NO$_2$C$_6$H$_4$ | H | H | CHOCH$_3$ | | | |
| 7 | 4-CH$_3$OC$_6$H$_4$ | H | H | CHOCH$_3$ | | | |
| 8 | C$_6$H$_5$CH$_2$ | H | H | CHOCH$_3$ | | | |
| 9 | 2-ClC$_6$H$_4$CH$_2$ | H | H | CHOCH$_3$ | | | |
| 10 | 3-NO$_2$C$_6$H$_4$CH$_2$ | H | H | CHOCH$_3$ | | | |

TABLE VIII-continued

| No. | R | R' | A | X | Isomer | m.p. (°C.) | δ (C=CH) |
|---|---|---|---|---|---|---|---|
| 11 | 4-CH$_3$OC$_6$H$_4$CH$_2$ | H | H | CHOCH$_3$ | | | |
| 12 | CH$_3$CO | H | H | CHOCH$_3$ | | | |
| 13 | C$_6$H$_5$CO | H | H | CHOCH$_3$ | | | |
| 14 | CH$_3$ | CH$_3$ | H | CHOCH$_3$ | | | |
| 15 | C$_6$H$_5$ | CH$_3$ | H | CHOCH$_3$ | | | |
| 16 | C$_6$H$_5$CH$_2$ | CH$_3$ | H | CHOCH$_3$ | | | |
| 17 | CH$_3$CO | CH$_3$ | H | CHOCH$_3$ | | | |
| 18 | C$_6$H$_5$CO | CH$_3$ | H | CHOCH$_3$ | | | |
| 19 | H | H | CH$_3$ | CHOCH$_3$ | | | |
| 20 | CH$_3$ | H | CH$_3$ | CHOCH$_3$ | | | |
| 21 | t-C$_4$H$_9$ | H | CH$_3$ | CHOCH$_3$ | | | |
| 22 | C$_6$H$_5$ | H | CH$_3$ | CHOCH$_3$ | | | |
| 23 | 2-Cl-C$_6$H$_4$ | H | CH$_3$ | CHOCH$_3$ | | | |
| 24 | 3-NO$_2$—C$_6$H$_4$ | H | CH$_3$ | CHOCH$_3$ | | | |
| 25 | 4-CH$_3$OC$_6$H$_4$ | H | CH$_3$ | CHOCH$_3$ | | | |
| 26 | C$_6$H$_5$CH$_2$ | H | CH$_3$ | CHOCH$_3$ | | | |
| 27 | 2-ClC$_6$H$_4$CH$_2$ | H | CH$_3$ | CHOCH$_3$ | | | |
| 28 | 3-NO$_2$C$_6$H$_4$CH$_2$ | H | CH$_3$ | CHOCH$_3$ | | | |
| 29 | 4-CH$_3$OC$_6$H$_4$CH$_2$ | H | CH$_3$ | CHOCH$_3$ | | | |
| 30 | CH$_3$CO | H | CH$_3$ | CHOCH$_3$ | | | |
| 31 | C$_6$H$_5$CO | H | CH$_3$ | CHOCH$_3$ | | | |
| 32 | CH$_3$ | CH$_3$ | CH$_3$ | CHOCH$_3$ | | | |
| 33 | C$_6$H$_5$ | CH$_3$ | CH$_3$ | CHOCH$_3$ | | | |
| 34 | C$_6$H$_5$CH$_2$ | CH$_3$ | CH$_3$ | CHOCH$_3$ | | | |
| 35 | CH$_3$CO | CH$_3$ | CH$_3$ | CHOCH$_3$ | | | |
| 36 | C$_6$H$_5$CO | CH$_3$ | CH$_3$ | CHOCH$_3$ | | | |
| 37 | CH$_3$ | H | C$_6$H$_5$ | CHOCH$_3$ | | | |
| 38 | C$_6$H$_5$ | H | C$_6$H$_5$ | CHOCH$_3$ | | | |
| 39 | C$_6$H$_5$CH$_2$ | H | C$_6$H$_5$ | CHOCH$_3$ | | | |
| 40 | CH$_3$CO | H | C$_6$H$_5$ | CHOCH$_3$ | | | |
| 41 | C$_6$H$_5$CO | H | C$_6$H$_5$ | CHOCH$_3$ | | | |
| 42 | CH$_3$ | CH$_3$ | C$_6$H$_5$ | CHOCH$_3$ | | | |
| 43 | C$_6$H$_5$ | CH$_3$ | C$_6$H$_5$ | CHOCH$_3$ | | | |
| 44 | C$_6$H$_5$CH$_2$ | CH$_3$ | C$_6$H$_5$ | CHOCH$_3$ | | | |
| 45 | CH$_3$CO | CH$_3$ | C$_6$H$_5$ | CHOCH$_3$ | | | |
| 46 | C$_6$H$_5$CO | CH$_3$ | C$_6$H$_5$ | CHOCH$_3$ | | | |
| 47 | H | H | H | NOCH$_3$ | | | |
| 48 | CH$_3$ | H | H | NOCH$_3$ | | | |
| 49 | t-C$_4$H$_9$ | H | H | NOCH$_3$ | | | |
| 50 | C$_6$H$_5$ | H | H | NOCH$_3$ | | | |
| 51 | 2-ClC$_6$H$_4$ | H | H | NOCH$_3$ | | | |
| 52 | 3-NO$_2$C$_6$H$_4$ | H | H | NOCH$_3$ | | | |
| 53 | 4-CH$_3$OC$_6$H$_4$ | H | H | NOCH$_3$ | | | |
| 54 | C$_6$H$_5$CH$_2$ | H | H | NOCH$_3$ | | | |
| 55 | 2-ClC$_6$H$_4$CH$_2$ | H | H | NOCH$_3$ | | | |
| 56 | 3-NO$_2$C$_6$H$_4$CH$_2$ | H | H | NOCH$_3$ | | | |
| 57 | 4-CH$_3$OC$_6$H$_4$CH$_2$ | H | H | NOCH$_3$ | | | |
| 58 | CH$_3$CO | H | H | NOCH$_3$ | | | |
| 59 | C$_6$H$_5$CO | H | H | NOCH$_3$ | | | |
| 60 | CH$_3$ | CH$_3$ | H | NOCH$_3$ | | | |
| 61 | C$_6$H$_5$ | CH$_3$ | H | NOCH$_3$ | | | |
| 62 | C$_6$H$_5$CH$_2$ | CH$_3$ | H | NOCH$_3$ | | | |
| 63 | CH$_3$CO | CH$_3$ | H | NOCH$_3$ | | | |
| 64 | C$_6$H$_5$CO | CH$_3$ | H | NOCH$_3$ | | | |
| 65 | H | H | CH$_3$ | NOCH$_3$ | | | |
| 66 | CH$_3$ | H | CH$_3$ | NOCH$_3$ | | | |
| 67 | t-C$_4$H$_9$ | H | CH$_3$ | NOCH$_3$ | | | |
| 68 | C$_6$H$_5$ | H | CH$_3$ | NOCH$_3$ | a | 155–158 | |
| 69 | 2-Cl-C$_6$H$_4$ | H | CH$_3$ | NOCH$_3$ | | | |
| 70 | 3-NO$_2$—C$_6$H$_4$ | H | CH$_3$ | NOCH$_3$ | a | 170 (decomp.) | |
| 71 | 4-CH$_3$OC$_6$H$_4$ | H | CH$_3$ | NOCH$_3$ | | | |
| 72 | C$_6$H$_5$CH$_2$ | H | CH$_3$ | NOCH$_3$ | | | |
| 73 | 2-ClC$_6$H$_4$CH$_2$ | H | CH$_3$ | NOCH$_3$ | | | |
| 74 | 3-NO$_2$C$_6$H$_4$CH$_2$ | H | CH$_3$ | NOCH$_3$ | | | |
| 75 | 4-CH$_3$OC$_6$H$_4$CH$_2$ | H | CH$_3$ | NOCH$_3$ | | | |
| 76 | CH$_3$CO | H | CH$_3$ | NOCH$_3$ | | | |
| 77 | C$_6$H$_5$CO | H | CH$_3$ | NOCH$_3$ | | | |

TABLE VIII-continued

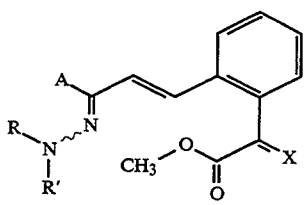

| No. | R | R' | A | X | Isomer | m.p. (°C.) | δ (C=CH) |
|---|---|---|---|---|---|---|---|
| 78 | CH₃ | CH₃ | CH₃ | NOCH₃ | | | |
| 79 | C₆H₅ | CH₃ | CH₃ | NOCH₃ | | | |
| 80 | C₆H₅CH₂ | CH₃ | CH₃ | NOCH₃ | | | |
| 81 | CH₃CO | CH₃ | CH₃ | NOCH₃ | | | |
| 82 | C₆H₅CO | CH₃ | CH₃ | NOCH₃ | | | |
| 83 | CH₃ | H | C₆H₅ | NOCH₃ | s | oil | 6.57/7.52 |
| 84 | C₆H₅ | H | C₆H₅ | NOCH₃ | | | |
| 85 | C₆H₅CH₂ | H | C₆H₅ | NOCH₃ | | | |
| 86 | CH₃CO | H | C₆H₅ | NOCH₃ | | | |
| 87 | C₆H₅CO | H | C₆H₅ | NOCH₃ | | | |
| 88 | CH₃ | CH₃ | C₆H₅ | NOCH₃ | | | |
| 89 | C₆H₅ | CH₃ | C₆H₅ | NOCH₃ | | | |
| 90 | C₆H₅CH₂ | CH₃ | C₆H₅ | NOCH₃ | | | |
| 91 | CH₃CO | CH₃ | C₆H₅ | NOCH₃ | | | |
| 92 | C₆H₅CO | CH₃ | C₆H₅ | NOCH₃ | | | |
| 93 | H | H | H | CHCH₃ | | | |
| 94 | CH₃ | H | H | CHCH₃ | | | |
| 95 | t-C₄H₉ | H | H | CHCH₃ | | | |
| 96 | C₆H₅ | H | H | CHCH₃ | | | |
| 97 | 2-ClC₆H₄ | H | H | CHCH₃ | | | |
| 98 | 3-NO₂C₆H₄ | H | H | CHCH₃ | | | |
| 99 | 4-CH₃OC₆H₄ | H | H | CHCH₃ | | | |
| 100 | C₆H₅CH₂ | H | H | CHCH₃ | | | |
| 101 | 2-ClC₆H₄CH₂ | H | H | CHCH₃ | | | |
| 102 | 3-NO₂C₆H₄CH₂ | H | H | CHCH₃ | | | |
| 103 | 4-CH₃OC₆H₄CH₂ | H | H | CHCH₃ | | | |
| 104 | CH₃CO | H | H | CHCH₃ | | | |
| 105 | C₆H₅CO | H | H | CHCH₃ | | | |
| 106 | CH₃ | CH₃ | H | CHCH₃ | | | |
| 107 | C₆H₅ | CH₃ | H | CHCH₃ | | | |
| 108 | C₆H₅CH₂ | CH₃ | H | CHCH₃ | | | |
| 109 | CH₃CO | CH₃ | H | CHCH₃ | | | |
| 110 | C₆H₅CO | CH₃ | H | CHCH₃ | | | |
| 111 | H | H | CH₃ | CHCH₃ | | | |
| 112 | CH₃ | H | CH₃ | CHCH₃ | | | |
| 113 | t-C₄H₉ | H | CH₃ | CHCH₃ | | | |
| 114 | C₆H₅ | H | CH₃ | CHCH₃ | | | |
| 115 | 2-Cl-C₆H₄ | H | CH₃ | CHCH₃ | | | |
| 116 | 3-NO₂—C₆H₄ | H | CH₃ | CHCH₃ | | | |
| 117 | 4-CH₃OC₆H₄ | H | CH₃ | CHCH₃ | | | |
| 118 | C₆H₅CH₂ | H | CH₃ | CHCH₃ | | | |
| 119 | 2-ClC₆H₄CH₂ | H | CH₃ | CHCH₃ | | | |
| 120 | 3-NO₂C₆H₄CH₂ | H | CH₃ | CHCH₃ | | | |
| 121 | 4-CH₃OC₆H₄CH₂ | H | CH₃ | CHCH₃ | | | |
| 122 | CH₃CO | H | CH₃ | CHCH₃ | | | |
| 123 | C₆H₅CO | H | CH₃ | CHCH₃ | | | |
| 124 | CH₃ | CH₃ | CH₃ | CHCH₃ | | | |
| 125 | C₆H₅ | CH₃ | CH₃ | CHCH₃ | | | |
| 126 | C₆H₅CH₂ | CH₃ | CH₃ | CHCH₃ | | | |
| 127 | CH₃CO | CH₃ | CH₃ | CHCH₃ | | | |
| 128 | C₆H₅CO | CH₃ | CH₃ | CHCH₃ | | | |
| 129 | CH₃ | H | C₆H₅ | CHCH₃ | | | |
| 130 | C₆H₅ | H | C₆H₅ | CHCH₃ | | | |
| 131 | C₆H₅CH₂ | H | C₆H₅ | CHCH₃ | | | |
| 132 | CH₃CO | H | C₆H₅ | CHCH₃ | | | |
| 133 | C₆H₅CO | H | C₆H₅ | CHCH₃ | | | |
| 134 | CH₃ | CH₃ | C₆H₅ | CHCH₃ | | | |
| 135 | C₆H₅ | CH₃ | C₆H₅ | CHCH₃ | | | |
| 136 | C₆H₅CH₂ | CH₃ | C₆H₅ | CHCH₃ | | | |
| 137 | CH₃CO | CH₃ | C₆H₅ | CHCH₃ | | | |
| 138 | C₆H₅CO | CH₃ | C₆H₅ | CHCH₃ | | | |
| 139 | H | H | H | CHC₂H₅ | | | |
| 140 | CH₃ | H | H | CHC₂H₅ | | | |
| 141 | t-C₄H₉ | H | H | CHC₂H₅ | | | |
| 142 | C₆H₅ | H | H | CHC₂H₅ | | | |
| 143 | 2-ClC₆H₄ | H | H | CHC₂H₅ | | | |
| 144 | 3-NO₂C₆H₄ | H | H | CHC₂H₅ | | | |
| 145 | 4-CH₃OC₆H₄ | H | H | CHC₂H₅ | | | |
| 146 | C₆H₅CH₂ | H | H | CHC₂H₅ | | | |

TABLE VIII-continued

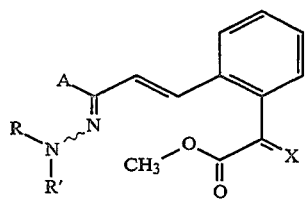

| No. | R | R' | A | X | Isomer | m.p. (°C.) | δ (C=CH) |
|---|---|---|---|---|---|---|---|
| 147 | 2-ClC6H4CH2 | H | H | CHC2H5 | | | |
| 148 | 3-NO2C6H4CH2 | H | H | CHC2H5 | | | |
| 149 | 4-CH3OC6H4CH2 | H | H | CHC2H5 | | | |
| 150 | CH3CO | H | H | CHC2H5 | | | |
| 151 | C6H5CO | H | H | CHC2H5 | | | |
| 152 | CH3 | CH3 | H | CHC2H5 | | | |
| 153 | C6H5 | CH3 | H | CHC2H5 | | | |
| 154 | C6H5CH2 | CH3 | H | CHC2H5 | | | |
| 155 | CH3CO | CH3 | H | CHC2H5 | | | |
| 156 | C6H5CO | CH3 | H | CHC2H5 | | | |
| 157 | H | H | CH3 | CHC2H5 | | | |
| 158 | CH3 | H | CH3 | CHC2H5 | | | |
| 159 | t-C4H9 | H | CH3 | CHC2H5 | | | |
| 160 | C6H5 | H | CH3 | CHC2H5 | | | |
| 161 | 2-Cl-C6H4 | H | CH3 | CHC2H5 | | | |
| 162 | 3-NO2—C6H4 | H | CH3 | CHC2H5 | | | |
| 163 | 4-CH3OC6H4 | H | CH3 | CHC2H5 | | | |
| 164 | C6H5CH2 | H | CH3 | CHC2H5 | | | |
| 165 | 2-ClC6H4CH2 | H | CH3 | CHC2H5 | | | |
| 166 | 3-NO2C6H4CH2 | H | CH3 | CHC2H5 | | | |
| 167 | 4-CH3OC6H4CH2 | H | CH3 | CHC2H5 | | | |
| 168 | CH3CO | H | CH3 | CHC2H5 | | | |
| 169 | C6H5CO | H | CH3 | CHC2H5 | | | |
| 170 | CH3 | CH3 | CH3 | CHC2H5 | | | |
| 171 | C6H5 | CH3 | CH3 | CHC2H5 | | | |
| 172 | C6H5CH2 | CH3 | CH3 | CHC2H5 | | | |
| 173 | CH3CO | CH3 | CH3 | CHC2H5 | | | |
| 174 | C6H5CO | CH3 | CH3 | CHC2H5 | | | |
| 175 | CH3 | H | C6H5 | CHC2H5 | | | |
| 176 | C6H5 | H | C6H5 | CHC2H5 | | | |
| 177 | C6H5CH2 | H | C6H5 | CHC2H5 | | | |
| 178 | CH3CO | H | C6H5 | CHC2H5 | | | |
| 179 | C6H5CO | H | C6H5 | CHC2H5 | | | |
| 180 | CH3 | CH3 | C6H5 | CHC2H5 | | | |
| 181 | C6H5 | CH3 | C6H5 | CHC2H5 | | | |
| 182 | C6H5CH2 | CH3 | C6H5 | CHC2H5 | | | |
| 183 | CH3CO | CH3 | C6H5 | CHC2H5 | | | |
| 184 | C6H5CO | CH3 | C6H5 | CHC2H5 | | | |

TABLE IX

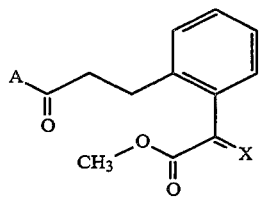

| No. | A | X | m.p. (°C.) | δ (CH2—CH2) |
|---|---|---|---|---|
| 1 | H | CHOCH3 | | |
| 2 | CH3 | CHOCH3 | | |
| 3 | t-C4H9 | CHOCH3 | | |
| 4 | C6H5 | CHOCH3 | | |
| 5 | 2-CH3C6H4 | CHOCH3 | | |
| 6 | 2-ClC6H4 | CHOCH3 | | |
| 7 | 3-CH3OC6H4 | CHOCH3 | | |
| 8 | 4-Cyano-C6H4 | CHOCH3 | | |
| 9 | 2,6-F2—C6H3 | CHOCH3 | | |
| 10 | β-Naphthyl | CHOCH3 | | |
| 11 | 3-Pyridyl | CHOCH3 | | |
| 12 | 2-Furyl | CHOCH3 | | |
| 13 | N-Methyl-3-indolyl | CHOCH3 | | |
| 14 | CF3 | CHOCH3 | | |
| 15 | HO | CHOCH3 | | |

TABLE IX-continued

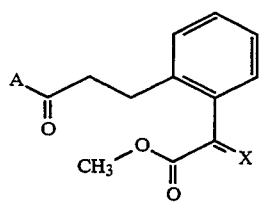

| No. | A | X | m.p. (°C.) | δ (CH₂—CH₂) |
|---|---|---|---|---|
| 16 | t-C₄H₉O | CHOCH₃ | | |
| 17 | CH₂=CH—CH₂O | CHOCH₃ | | |
| 18 | C₆H₅CH₂O | CHOCH₃ | | |
| 19 | 2-CH₃C₆H₄CH₂O | CHOCH₃ | | |
| 20 | 2-ClC₆H₄CH₂O | CHOCH₃ | | |
| 21 | 3-CH₃OC₆H₄CH₂O | CHOCH₃ | | |
| 22 | 4-Cyano-C₆H₄CH₂O | CHOCH₃ | | |
| 23 | 2,6-F₂—C₆H₃CH₂O | CHOCH₃ | | |
| 24 | 2-Pyridyl-methoxy | CHOCH₃ | | |
| 25 | t-C₄H₉—(CH₃)₂—SiO | CHOCH₃ | | |
| 26 | CH₃NH | CHOCH₃ | | |
| 27 | C₆H₅NH | CHOCH₃ | | |
| 28 | 2-CH₃C₆H₄NH | CHOCH₃ | | |
| 29 | 2-ClC₆H₄NH | CHOCH₃ | | |
| 30 | 3-CH₃OC₆H₄NH | CHOCH₃ | | |
| 31 | 4-Cyano-C₆H₄NH | CHOCH₃ | | |
| 32 | 2,6-F₂—C₆H₃NH | CHOCH₃ | | |
| 33 | C₆H₅NCH₃ | CHOCH₃ | | |
| 34 | 2-ClC₆H₄NCH₃ | CHOCH₃ | | |
| 35 | 4-Cyano-C₆H₄NCH₃ | CHOCH₃ | | |
| 36 | C₆H₅CH₂NH | CHOCH₃ | | |
| 37 | 2-CH₃C₆H₄CH₂NH | CHOCH₃ | | |
| 38 | 2-Cl—C₆H₄CH₂NH | CHOCH₃ | | |
| 39 | 3-CH₃O—C₆H₄CH₂NH | CHOCH₃ | | |
| 40 | 4-Cyano-C₆H₄CH₂NH | CHOCH₃ | | |
| 41 | 2,6-F₂C₆H₃CH₂NH | CHOCH₃ | | |
| 42 | C₆H₅CH₂NCH₃ | CHOCH₃ | | |
| 43 | 2-Cl—C₆H₄CH₂NCH₃ | CHOCH₃ | | |
| 44 | 4-Cyano-C₆H₄CH₂NCH₃ | CHOCH₃ | | |
| 45 | HS | CHOCH₃ | | |
| 46 | C₆H₅CH₂S | CHOCH₃ | | |
| 47 | H | NOCH₃ | | |
| 48 | CH₃ | NOCH₃ | oil | 2.69 (mc) |
| 49 | t-C₄H₉ | NOCH₃ | | |
| 50 | C₆H₅ | NOCH₃ | oil | |
| 51 | 2-CH₃C₆H₄ | NOCH₃ | | |
| 52 | 2-ClC₆H₄ | NOCH₃ | | |
| 53 | 3-CH₃OC₆H₄ | NOCH₃ | | |
| 54 | 4-Cyano-C₆H₄ | NOCH₃ | | |
| 55 | 2,6-F₂—C₆H₃ | NOCH₃ | | |
| 56 | β-Naphthyl | NOCH₃ | | |
| 57 | 3-Pyridyl | NOCH₃ | | |
| 58 | 2-Furyl | NOCH₃ | | |
| 59 | N-Methyl-3-indolyl | NOCH₃ | | |
| 60 | CF₃ | NOCH₃ | | |
| 61 | HO | NOCH₃ | | |
| 62 | t-C₄H₉O | NOCH₃ | | |
| 63 | CH₂=CH—CH₂O | NOCH₃ | | |
| 64 | C₆H₅CH₂O | NOCH₃ | | |
| 65 | 2-CH₃C₆H₄CH₂O | NOCH₃ | | |
| 66 | 2-ClC₆H₄CH₂O | NOCH₃ | | |
| 67 | 3-CH₃OC₆H₄CH₂O | NOCH₃ | | |
| 68 | 4-Cyano-C₆H₄CH₂O | NOCH₃ | | |
| 69 | 2,6-F₂—C₆H₃CH₂O | NOCH₃ | | |
| 70 | 2-Pyridyl-methoxy | NOCH₃ | | |
| 71 | t-C₄H₉—(CH₃)₂—SiO | NOCH₃ | | |
| 72 | CH₃NH | NOCH₃ | | |
| 73 | C₆H₅NH | NOCH₃ | | |
| 74 | 2-CH₃C₆H₄NH | NOCH₃ | | |
| 75 | 2-ClC₆H₄NH | NOCH₃ | | |
| 76 | 3-CH₃OC₆H₄NH | NOCH₃ | | |
| 77 | 4-Cyano-C₆H₄NH | NOCH₃ | | |
| 78 | 2,6-F₂—C₆H₃NH | NOCH₃ | | |
| 79 | C₆H₅NCH₃ | NOCH₃ | | |
| 80 | 2-ClC₆H₄NCH₃ | NOCH₃ | | |
| 81 | 4-Cyano-C₆H₄NCH₃ | NOCH₃ | | |
| 82 | C₆H₅CH₂NH | NOCH₃ | | |
| 83 | 2-CH₃C₆H₄CH₂NH | NOCH₃ | | |
| 84 | 2-Cl—C₆H₄CH₂NH | NOCH₃ | | |
| 85 | 3-CH₃O—C₆H₄CH₂NH | NOCH₃ | | |

TABLE IX-continued

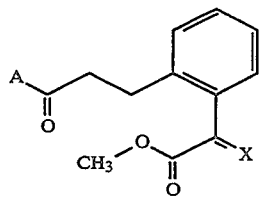

| No. | A | X | m.p. (°C.) | δ (CH₂—CH₂) |
|---|---|---|---|---|
| 86 | 4-Cyano-C₆H₄CH₂NH | NOCH₃ | | |
| 87 | 2,6-F₂C₆H₃CH₂NH | NOCH₃ | | |
| 88 | C₆H₅CH₂NCH₃ | NOCH₃ | | |
| 89 | 2-Cl—C₆H₄CH₂NCH₃ | NOCH₃ | | |
| 90 | 4-Cyano-C₆H₄CH₂NCH₃ | NOCH₃ | | |
| 91 | HS | NOCH₃ | | |
| 92 | C₆H₅CH₂S | NOCH₃ | | |
| 93 | H | CHCH₃ | | |
| 94 | CH₃ | CHCH₃ | | |
| 95 | t-C₄H₉ | CHCH₃ | | |
| 96 | C₆H₅ | CHCH₃ | | |
| 97 | 2-CH₃C₆H₄ | CHCH₃ | | |
| 98 | 2-ClC₆H₄ | CHCH₃ | | |
| 99 | 3-CH₃OC₆H₄ | CHCH₃ | | |
| 100 | 4-Cyano-C₆H₄ | CHCH₃ | | |
| 101 | 2,6-F₂—C₆H₃ | CHCH₃ | | |
| 102 | β-Naphthyl | CHCH₃ | | |
| 103 | 3-Pyridyl | CHCH₃ | | |
| 104 | 2-Furyl | CHCH₃ | | |
| 105 | N-Methyl-3-indolyl | CHCH₃ | | |
| 106 | CF₃ | CHCH₃ | | |
| 107 | HO | CHCH₃ | | |
| 108 | t-C₄H₉O | CHCH₃ | | |
| 109 | CH₂=CH—CH₂O | CHCH₃ | | |
| 110 | C₆H₅CH₂O | CHCH₃ | | |
| 111 | 2-CH₃C₆H₄CH₂O | CHCH₃ | | |
| 112 | 2-ClC₆H₄CH₂O | CHCH₃ | | |
| 113 | 3-CH₃OC₆H₄CH₂O | CHCH₃ | | |
| 114 | 4-Cyano-C₆H₄CH₂O | CHCH₃ | | |
| 115 | 2,6-F₂—C₆H₃CH₂O | CHCH₃ | | |
| 116 | 2-Pyridyl-methoxy | CHCH₃ | | |
| 117 | t-C₄H₉—(CH₃)₂—SiO | CHCH₃ | | |
| 118 | CH₃NH | CHCH₃ | | |
| 119 | C₆H₅NH | CHCH₃ | | |
| 120 | 2-CH₃C₆H₄NH | CHCH₃ | | |
| 121 | 2-ClC₆H₄NH | CHCH₃ | | |
| 122 | 3-CH₃OC₆H₄NH | CHCH₃ | | |
| 123 | 4-Cyano-C₆H₄NH | CHCH₃ | | |
| 124 | 2,6-F₂—C₆H₃NH | CHCH₃ | | |
| 125 | C₆H₅NCH₃ | CHCH₃ | | |
| 126 | 2-ClC₆H₄NCH₃ | CHCH₃ | | |
| 127 | 4-Cyano-C₆H₄NCH₃ | CHCH₃ | | |
| 128 | C₆H₅CH₂NH | CHCH₃ | | |
| 129 | 2-CH₃C₆H₄CH₂NH | CHCH₃ | | |
| 130 | 2-Cl—C₆H₄CH₂NH | CHCH₃ | | |
| 131 | 3-CH₃O—C₆H₄CH₂NH | CHCH₃ | | |
| 132 | 4-Cyano-C₆H₄CH₂NH | CHCH₃ | | |
| 133 | 2,6-F₂C₆H₃CH₂NH | CHCH₃ | | |
| 134 | C₆H₅CH₂NCH₃ | CHCH₃ | | |
| 135 | 2-Cl—C₆H₄CH₂NCH₃ | CHCH₃ | | |
| 136 | 4-Cyano-C₆H₄CH₂NCH₃ | CHCH₃ | | |
| 137 | HS | CHCH₃ | | |
| 138 | C₆H₅CH₂S | CHCH₃ | | |
| 139 | H | CHC₂H₅ | | |
| 140 | CH₃ | CHC₂H₅ | | |
| 141 | t-C₄H₉ | CHC₂H₅ | | |
| 142 | C₆H₅ | CHC₂H₅ | | |
| 143 | 2-CH₃C₆H₄ | CHC₂H₅ | | |
| 144 | 2-ClC₆H₄ | CHC₂H₅ | | |
| 145 | 3-CH₃OC₆H₄ | CHC₂H₅ | | |
| 146 | 4-Cyano-C₆H₄ | CHC₂H₅ | | |
| 147 | 2,6-F₂—C₆H₃ | CHC₂H₅ | | |
| 148 | β-Naphthyl | CHC₂H₅ | | |
| 149 | 3-Pyridyl | CHC₂H₅ | | |
| 150 | 2-Furyl | CHC₂H₅ | | |
| 151 | N-Methyl-3-indolyl | CHC₂H₅ | | |
| 152 | CF₃ | CHC₂H₅ | | |
| 153 | HO | CHC₂H₅ | | |
| 154 | t-C₄H₉O | CHC₂H₅ | | |
| 155 | CH₂=CH—CH₂O | CHC₂H₅ | | |

TABLE IX-continued

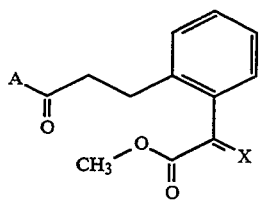

| No. | A | X | m.p. (°C.) | δ (C$\underline{H}_2$—C$\underline{H}_2$) |
|---|---|---|---|---|
| 156 | $C_6H_5CH_2O$ | $CHC_2H_5$ | | |
| 157 | $2\text{-}CH_3C_6H_4CH_2O$ | $CHC_2H_5$ | | |
| 158 | $2\text{-}ClC_6H_4CH_2O$ | $CHC_2H_5$ | | |
| 159 | $3\text{-}CH_3OC_6H_4CH_2O$ | $CHC_2H_5$ | | |
| 160 | $4\text{-}Cyano\text{-}C_6H_4CH_2O$ | $CHC_2H_5$ | | |
| 161 | $2,6\text{-}F_2\text{—}C_6H_3CH_2O$ | $CHC_2H_5$ | | |
| 162 | 2-Pyridyl-methoxy | $CHC_2H_5$ | | |
| 163 | $t\text{-}C_4H_9\text{—}(CH_3)_2\text{—}SiO$ | $CHC_2H_5$ | | |
| 164 | $CH_3NH$ | $CHC_2H_5$ | | |
| 165 | $C_6H_5NH$ | $CHC_2H_5$ | | |
| 166 | $2\text{-}CH_3C_6H_4NH$ | $CHC_2H_5$ | | |
| 167 | $2\text{-}ClC_6H_4NH$ | $CHC_2H_5$ | | |
| 168 | $3\text{-}CH_3OC_6H_4NH$ | $CHC_2H_5$ | | |
| 169 | $4\text{-}Cyano\text{-}C_6H_4NH$ | $CHC_2H_5$ | | |
| 170 | $2,6\text{-}F_2\text{—}C_6H_3NH$ | $CHC_2H_5$ | | |
| 171 | $C_6H_5NCH_3$ | $CHC_2H_5$ | | |
| 172 | $2\text{-}ClC_6H_4NCH_3$ | $CHC_2H_5$ | | |
| 173 | $4\text{-}Cyano\text{-}C_6H_4NCH_3$ | $CHC_2H_5$ | | |
| 174 | $C_6H_5CH_2NH$ | $CHC_2H_5$ | | |
| 175 | $2\text{-}CH_3C_6H_4CH_2NH$ | $CHC_2H_5$ | | |
| 176 | $2\text{-}Cl\text{—}C_6H_4CH_2NH$ | $CHC_2H_5$ | | |
| 177 | $3\text{-}CH_3O\text{—}C_6H_4CH_2NH$ | $CHC_2H_5$ | | |
| 178 | $4\text{-}Cyano\text{-}C_6H_4CH_2NH$ | $CHC_2H_5$ | | |
| 179 | $2,6\text{-}F_2C_6H_3CH_2NH$ | $CHC_2H_5$ | | |
| 180 | $C_6H_5CH_2NCH_3$ | $CHC_2H_5$ | | |
| 181 | $2\text{-}Cl\text{—}C_6H_4CH_2NCH_3$ | $CHC_2H_5$ | | |
| 182 | $4\text{-}Cyano\text{-}C_6H_4CH_2NCH_3$ | $CHC_2H_5$ | | |
| 183 | HS | $CHC_2H_5$ | | |
| 184 | $C_6H_5CH_2S$ | $CHC_2H_5$ | | |

TABLE X

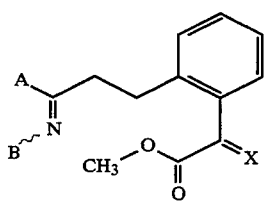

| No. | A | B | X | Isomer | m.p. (°C.) | δ (C$\underline{H}_2$—C$\underline{H}_2$) |
|---|---|---|---|---|---|---|
| 1 | H | $CH_3$ | $CHOCH_3$ | | | |
| 2 | H | $t\text{-}C_4H_9$ | $CHOCH_3$ | | | |
| 3 | H | $C_6H_5$ | $CHOCH_3$ | | | |
| 4 | H | $2\text{-}CH_3C_6H_4$ | $CHOCH_3$ | | | |
| 5 | H | $4\text{-}Cyano\text{-}C_6H_4$ | $CHOCH_3$ | | | |
| 6 | H | $2,6\text{-}F_2\text{—}C_6H_3$ | $CHOCH_3$ | | | |
| 7 | $CH_3$ | $CH_3$ | $CHOCH_3$ | | | |
| 8 | $CH_3$ | $t\text{-}C_4H_9$ | $CHOCH_3$ | | | |
| 9 | $CH_3$ | $C_6H_5$ | $CHOCH_3$ | | | |
| 10 | $CH_3$ | $2\text{-}CH_3C_6H_4$ | $CHOCH_3$ | | | |
| 11 | $CH_3$ | $4\text{-}Cyano\text{-}C_6H_4$ | $CHOCH_3$ | | | |
| 12 | $CH_3$ | $2,6\text{-}F_2C_6H_3$ | $CHOCH_3$ | | | |
| 13 | $C_6H_5$ | $CH_3$ | $CHOCH_3$ | | | |
| 14 | $C_6H_5$ | $C_6H_5$ | $CHOCH_3$ | | | |
| 15 | $C_6H_5$ | $2,6\text{-}F_2C_6H_3$ | $CHOCH_3$ | | | |
| 16 | H | HO | $CHOCH_3$ | | | |
| 17 | H | $CH_3O$ | $CHOCH_3$ | | | |
| 18 | H | $t\text{-}C_4H_9O$ | $CHOCH_3$ | | | |
| 19 | H | $H_2C\text{=}CClCH_2O$ | $CHOCH_3$ | | | |
| 20 | H | $C_6H_5CH_2O$ | $CHOCH_3$ | | | |
| 21 | H | $2\text{-}CH_3C_6H_4CH_2O$ | $CHOCH_3$ | | | |
| 22 | H | $2\text{-}ClC_6H_4CH_2O$ | $CHOCH_3$ | | | |
| 23 | H | $3\text{-}CH_3OC_6H_4CH_2O$ | $CHOCH_3$ | | | |
| 24 | H | $4\text{-}Cyano\text{-}C_6H_4CH_2O$ | $CHOCH_3$ | | | |

TABLE X-continued

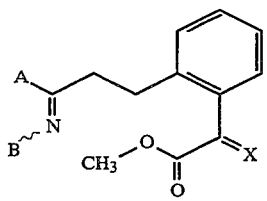

| No. | A | B | X | Isomer | m.p. (°C.) | δ (CH₂—CH₂) |
|---|---|---|---|---|---|---|
| 25 | H | 2,6-F₂C₆H₃CH₂O | CHOCH₃ | | | |
| 26 | H | 3-Pyridylmethoxy | CHOCH₃ | | | |
| 27 | H | 5-Chlorothien-2-ylmethoxy | CHOCH₃ | | | |
| 28 | H | CH₃CO | CHOCH₃ | | | |
| 29 | H | C₆H₅CO | CHOCH₃ | | | |
| 30 | CH₃ | HO | CHOCH₃ | | | |
| 31 | CH₃ | CH₃O | CHOCH₃ | | | |
| 32 | CH₃ | t-C₄H₉O | CHOCH₃ | | | |
| 33 | CH₃ | H₂C=CClCH₂O | CHOCH₃ | | | |
| 34 | CH₃ | C₆H₅CH₂O | CHOCH₃ | | | |
| 35 | CH₃ | 2-CH₃—C₆H₄CH₂O | CHOCH₃ | | | |
| 36 | CH₃ | 2-Cl—C₆H₄CH₂O | CHOCH₃ | | | |
| 37 | CH₃ | 3-CH₃OC₆H₄CH₂O | CHOCH₃ | | | |
| 38 | CH₃ | 4-Cyano-C₆H₄CH₂O | CHOCH₃ | | | |
| 39 | CH₃ | 2,6-F₂—C₆H₃—CH₂O | CHOCH₃ | | | |
| 40 | CH₃ | 3-Pyridylmethoxy | CHOCH₃ | | | |
| 41 | CH₃ | 5-Chlorothien-2-ylmethoxy | CHOCH₃ | | | |
| 42 | CH₃ | CH₃CO | CHOCH₃ | | | |
| 43 | CH₃ | C₆H₅CO | CHOCH₃ | | | |
| 44 | C₆H₅ | HO | CHOCH₃ | | | |
| 45 | C₆H₅ | CH₃O | CHOCH₃ | | | |
| 46 | C₆H₅ | H₂C=CClCH₂O | CHOCH₃ | | | |
| 47 | C₆H₅ | C₆H₅CH₂O | CHOCH₃ | | | |
| 48 | C₆H₅ | 2,6-F₂—C₆H₃CH₂O | CHOCH₃ | | | |
| 49 | C₆H₅ | CH₃O | CHOCH₃ | | | |
| 50 | H | CH₃NH | CHOCH₃ | | | |
| 51 | H | (CH₃)₂N | CHOCH₃ | | | |
| 52 | H | C₆H₅NH | CHOCH₃ | | | |
| 53 | H | 2-Cl—C₆H₄NH | CHOCH₃ | | | |
| 54 | H | C₆H₅NCH₃ | CHOCH₃ | | | |
| 55 | H | C₆H₅CH₂NH | CHOCH₃ | | | |
| 56 | H | 2-Cl—C₆H₄CH₂NH | CHOCH₃ | | | |
| 57 | H | C₆H₅CH₂NCH₃ | CHOCH₃ | | | |
| 58 | H | CH₃CO | CHOCH₃ | | | |
| 59 | H | C₆H₅CO | CHOCH₃ | | | |
| 60 | CH₃ | CH₃NH | CHOCH₃ | | | |
| 61 | CH₃ | (CH₃)₂N | CHOCH₃ | | | |
| 62 | CH₃ | C₆H₅NH | CHOCH₃ | | | |
| 63 | CH₃ | 2-ClC₆H₄NH | CHOCH₃ | | | |
| 64 | CH₃ | C₆H₅NCH₃ | CHOCH₃ | | | |
| 65 | CH₃ | C₆H₅CH₂NH | CHOCH₃ | | | |
| 66 | CH₃ | 2-Cl—C₆H₄CH₂NH | CHOCH₃ | | | |
| 67 | CH₃ | C₆H₅CH₂NCH₃ | CHOCH₃ | | | |
| 68 | CH₃ | CH₃CO | CHOCH₃ | | | |
| 69 | CH₃ | C₆H₅CO | CHOCH₃ | | | |
| 70 | C₆H₅ | CH₃NH | CHOCH₃ | | | |
| 71 | C₆H₅ | (CH₃)₂N | CHOCH₃ | | | |
| 72 | C₆H₅ | C₆H₅NH | CHOCH₃ | | | |
| 73 | C₆H₅ | C₆H₅NCH₃ | CHOCH₃ | | | |
| 74 | C₆H₅ | CH₃CO | CHOCH₃ | | | |
| 75 | C₆H₅ | C₆H₅CO | CHOCH₃ | | | |
| 76 | H | CH₃ | NOCH₃ | | | |
| 77 | H | t-C₄H₉ | NOCH₃ | | | |
| 78 | H | C₆H₅ | NOCH₃ | | | |
| 79 | H | 2-CH₃C₆H₄ | NOCH₃ | | | |
| 80 | H | 4-Cyano-C₆H₄ | NOCH₃ | | | |
| 81 | H | 2,6-F₂—C₆H₃ | NOCH₃ | | | |
| 82 | CH₃ | CH₃ | NOCH₃ | | | |
| 83 | CH₃ | t-C₄H₉ | NOCH₃ | | | |
| 84 | CH₃ | C₆H₅ | NOCH₃ | | | |
| 85 | CH₃ | 2-CH₃C₆H₄ | NOCH₃ | | | |
| 86 | CH₃ | 4-Cyano-C₆H₄ | NOCH₃ | | | |
| 87 | CH₃ | 2,6-F₂C₆H₃ | NOCH₃ | | | |
| 88 | C₆H₅ | CH₃ | NOCH₃ | | | |
| 89 | C₆H₅ | C₆H₅ | NOCH₃ | | | |
| 90 | C₆H₅ | 2,6-F₂C₆H₃ | NOCH₃ | | | |
| 91 | H | HO | NOCH₃ | | | |

TABLE X-continued

| No. | A | B | X | Isomer | m.p. (°C.) | δ (C$\underline{H}_2$—C$\underline{H}_2$) |
|---|---|---|---|---|---|---|
| 92 | H | CH$_3$O | NOCH$_3$ | | | |
| 93 | H | t-C$_4$H$_9$O | NOCH$_3$ | | | |
| 94 | H | H$_2$C=CClCH$_2$O | NOCH$_3$ | | | |
| 95 | H | C$_6$H$_5$CH$_2$O | NOCH$_3$ | | | |
| 96 | H | 2-CH$_3$C$_6$H$_4$CH$_2$O | NOCH$_3$ | | | |
| 97 | H | 2-ClC$_6$H$_4$CH$_2$O | NOCH$_3$ | | | |
| 98 | H | 3-CH$_3$OC$_6$H$_4$CH$_2$O | NOCH$_3$ | | | |
| 99 | H | 4-Cyano-C$_6$H$_4$CH$_2$O | NOCH$_3$ | | | |
| 100 | H | 2,6-F$_2$C$_6$H$_3$CH$_2$O | NOCH$_3$ | | | |
| 101 | H | 3-Pyridylmethoxy | NOCH$_3$ | | | |
| 102 | H | 5-Chlorothien-2-ylmethoxy | NOCH$_3$ | | | |
| 103 | H | CH$_3$CO | NOCH$_3$ | | | |
| 104 | H | C$_6$H$_5$CO | NOCH$_3$ | | | |
| 105 | CH$_3$ | HO | NOCH$_3$ | | | |
| 106 | CH$_3$ | CH$_3$O | NOCH$_3$ | | | |
| 107 | CH$_3$ | t-C$_4$H$_9$O | NOCH$_3$ | | | |
| 108 | CH$_3$ | H$_2$C=CClCH$_2$O | NOCH$_3$ | | | |
| 109 | CH$_3$ | C$_6$H$_5$CH$_2$O | NOCH$_3$ | | | |
| 110 | CH$_3$ | 2-CH$_3$—C$_6$H$_4$CH$_2$O | NOCH$_3$ | | | |
| 111 | CH$_3$ | 2-Cl—C$_6$H$_4$CH$_2$O | NOCH$_3$ | | | |
| 112 | CH$_3$ | 3-CH$_3$OC$_6$H$_4$CH$_2$O | NOCH$_3$ | | | |
| 113 | CH$_3$ | 4-Cyano-C$_6$H$_4$CH$_2$O | NOCH$_3$ | | | |
| 114 | CH$_3$ | 2,6-F$_2$—C$_6$H$_3$—CH$_2$O | NOCH$_3$ | | | |
| 115 | CH$_3$ | 3-Pyridylmethoxy | NOCH$_3$ | | | |
| 116 | CH$_3$ | 5-Chlorothien-2-ylmethoxy | NOCH$_3$ | | | |
| 117 | CH$_3$ | CH$_3$CO | NOCH$_3$ | | | |
| 118 | CH$_3$ | C$_6$H$_5$CO | NOCH$_3$ | | | |
| 119 | C$_6$H$_5$ | HO | NOCH$_3$ | | | |
| 120 | C$_6$H$_5$ | CH$_3$O | NOCH$_3$ | | | |
| 121 | C$_6$H$_5$ | H$_2$C=CClCH$_2$O | NOCH$_3$ | | | |
| 122 | C$_6$H$_5$ | C$_6$H$_5$CH$_2$O | NOCH$_3$ | | | |
| 123 | C$_6$H$_5$ | 2,6-F$_2$—C$_6$H$_3$CH$_2$O | NOCH$_3$ | | | |
| 124 | C$_6$H$_5$ | CH$_3$O | NOCH$_3$ | | | |
| 125 | H | CH$_3$NH | NOCH$_3$ | | | |
| 126 | H | (CH$_3$)$_2$N | NOCH$_3$ | | | |
| 127 | H | C$_6$H$_5$NH | NOCH$_3$ | | | |
| 128 | H | 2-Cl—C$_6$H$_4$NH | NOCH$_3$ | | | |
| 129 | H | C$_6$H$_5$NCH$_3$ | NOCH$_3$ | | | |
| 130 | H | C$_6$H$_5$CH$_2$NH | NOCH$_3$ | | | |
| 131 | H | 2-Cl—C$_6$H$_4$CH$_2$NH | NOCH$_3$ | | | |
| 132 | H | C$_6$H$_5$CH$_2$NCH$_3$ | NOCH$_3$ | | | |
| 133 | H | CH$_3$CO | NOCH$_3$ | | | |
| 134 | H | C$_6$H$_5$CO | NOCH$_3$ | | | |
| 135 | CH$_3$ | CH$_3$NH | NOCH$_3$ | | | |
| 136 | CH$_3$ | (CH$_3$)$_2$N | NOCH$_3$ | | | |
| 137 | CH$_3$ | C$_6$H$_5$NH | NOCH$_3$ | | | |
| 138 | CH$_3$ | 2-ClC$_6$H$_4$NH | NOCH$_3$ | | | |
| 139 | CH$_3$ | C$_6$H$_5$NCH$_3$ | NOCH$_3$ | | | |
| 140 | CH$_3$ | C$_6$H$_5$CH$_2$NH | NOCH$_3$ | | | |
| 141 | CH$_3$ | 2-Cl—C$_6$H$_4$CH$_2$NH | NOCH$_3$ | | | |
| 142 | CH$_3$ | C$_6$H$_5$CH$_2$NCH$_3$ | NOCH$_3$ | | | |
| 143 | CH$_3$ | CH$_3$CO | NOCH$_3$ | | | |
| 144 | CH$_3$ | C$_6$H$_5$CO | NOCH$_3$ | | | |
| 145 | C$_6$H$_5$ | CH$_3$NH | NOCH$_3$ | | | |
| 146 | C$_6$H$_5$ | (CH$_3$)$_2$N | NOCH$_3$ | | | |
| 147 | C$_6$H$_5$ | C$_6$H$_5$NH | NOCH$_3$ | | | |
| 148 | C$_6$H$_5$ | C$_6$H$_5$NCH$_3$ | NOCH$_3$ | | | |
| 149 | C$_6$H$_5$ | CH$_3$CO | NOCH$_3$ | | | |
| 150 | C$_6$H$_5$ | C$_6$H$_5$CO | NOCH$_3$ | | | |
| 151 | H | CH$_3$ | CHCH$_3$ | | | |
| 152 | H | t-C$_4$H$_9$ | CHCH$_3$ | | | |
| 153 | H | C$_6$H$_5$ | CHCH$_3$ | | | |
| 154 | H | 2-CH$_3$C$_6$H$_4$ | CHCH$_3$ | | | |
| 155 | H | 4-Cyano-C$_6$H$_4$ | CHCH$_3$ | | | |
| 156 | H | 2,6-F$_2$—C$_6$H$_3$ | CHCH$_3$ | | | |
| 157 | CH$_3$ | CH$_3$ | CHCH$_3$ | | | |
| 158 | CH$_3$ | t-C$_4$H$_9$ | CHCH$_3$ | | | |

TABLE X-continued

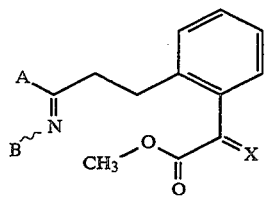

| No. | A | B | X | Isomer | m.p. (°C.) | δ (CH₂—CH₂) |
|---|---|---|---|---|---|---|
| 159 | CH₃ | C₆H₅ | CHCH₃ | | | |
| 160 | CH₃ | 2-CH₃C₆H₄ | CHCH₃ | | | |
| 161 | CH₃ | 4-Cyano-C₆H₄ | CHCH₃ | | | |
| 162 | CH₃ | 2,6-F₂C₆H₃ | CHCH₃ | | | |
| 163 | C₆H₅ | CH₃ | CHCH₃ | | | |
| 164 | C₆H₅ | C₆H₅ | CHCH₃ | | | |
| 165 | C₆H₅ | 2,6-F₂C₆H₃ | CHCH₃ | | | |
| 166 | H | HO | CHCH₃ | | | |
| 167 | H | CH₃O | CHCH₃ | | | |
| 168 | H | t-C₄H₉O | CHCH₃ | | | |
| 169 | H | H₂C=CClCH₂O | CHCH₃ | | | |
| 170 | H | C₆H₅CH₂O | CHCH₃ | | | |
| 171 | H | 2-CH₃C₆H₄CH₂O | CHCH₃ | | | |
| 172 | H | 2-ClC₆H₄CH₂O | CHCH₃ | | | |
| 173 | H | 3-CH₃OC₆H₄CH₂O | CHCH₃ | | | |
| 174 | H | 4-Cyano-C₆H₄CH₂O | CHCH₃ | | | |
| 175 | H | 2,6-F₂C₆H₃CH₂O | CHCH₃ | | | |
| 176 | H | 3-Pyridylmethoxy | CHCH₃ | | | |
| 177 | H | 5-Chlorothien-2-ylmethoxy | CHCH₃ | | | |
| 178 | H | CH₃CO | CHCH₃ | | | |
| 179 | H | C₆H₅CO | CHCH₃ | | | |
| 180 | CH₃ | HO | CHCH₃ | | | |
| 181 | CH₃ | CH₃O | CHCH₃ | | | |
| 182 | CH₃ | t-C₄H₉O | CHCH₃ | | | |
| 183 | CH₃ | H₂C=CClCH₂O | CHCH₃ | | | |
| 184 | CH₃ | C₆H₅CH₂O | CHCH₃ | | | |
| 185 | CH₃ | 2-CH₃—C₆H₄CH₂O | CHCH₃ | | | |
| 186 | CH₃ | 2-Cl—C₆H₄CH₂O | CHCH₃ | | | |
| 187 | CH₃ | 3-CH₃OC₆H₄CH₂O | CHCH₃ | | | |
| 188 | CH₃ | 4-Cyano-C₆H₄CH₂O | CHCH₃ | | | |
| 189 | CH₃ | 2,6-F₂—C₆H₄—CH₂O | CHCH₃ | | | |
| 190 | CH₃ | 3-Pyridylmethoxy | CHCH₃ | | | |
| 191 | CH₃ | 5-Chlorothien-2-ylmethoxy | CHCH₃ | | | |
| 192 | CH₃ | CH₃CO | CHCH₃ | | | |
| 193 | CH₃ | C₆H₅CO | CHCH₃ | | | |
| 194 | C₆H₅ | HO | CHCH₃ | | | |
| 195 | C₆H₅ | CH₃O | CHCH₃ | | | |
| 196 | C₆H₅ | H₂C=CClCH₂O | CHCH₃ | | | |
| 197 | C₆H₅ | C₆H₅CH₂O | CHCH₃ | | | |
| 198 | C₆H₅ | 2,6-F₂—C₆H₃CH₂O | CHCH₃ | | | |
| 199 | C₆H₅ | CH₃O | CHCH₃ | | | |
| 200 | H | CH₃NH | CHCH₃ | | | |
| 201 | H | (CH₃)₂N | CHCH₃ | | | |
| 202 | H | C₆H₅NH | CHCH₃ | | | |
| 203 | H | 2-Cl—C₆H₄NH | CHCH₃ | | | |
| 204 | H | C₆H₅NCH₃ | CHCH₃ | | | |
| 205 | H | C₆H₅CH₂NH | CHCH₃ | | | |
| 206 | H | 2-Cl—C₆H₄CH₂NH | CHCH₃ | | | |
| 207 | H | C₆H₅CH₂NCH₃ | CHCH₃ | | | |
| 208 | H | CH₃CO | CHCH₃ | | | |
| 209 | H | C₆H₅CO | CHCH₃ | | | |
| 210 | CH₃ | CH₃NH | CHCH₃ | | | |
| 211 | CH₃ | (CH₃)₂N | CHCH₃ | | | |
| 212 | CH₃ | C₆H₅NH | CHCH₃ | | | |
| 213 | CH₃ | 2-ClC₆H₄NH | CHCH₃ | | | |
| 214 | CH₃ | C₆H₅NCH₃ | CHCH₃ | | | |
| 215 | CH₃ | C₆H₅CH₂NH | CHCH₃ | | | |
| 216 | CH₃ | 2-Cl—C₆H₄CH₂NH | CHCH₃ | | | |
| 217 | CH₃ | C₆H₅CH₂NCH₃ | CHCH₃ | | | |
| 218 | CH₃ | CH₃CO | CHCH₃ | | | |
| 219 | CH₃ | C₆H₅CO | CHCH₃ | | | |
| 220 | C₆H₅ | CH₃NH | CHCH₃ | | | |
| 221 | C₆H₅ | (CH₃)₂N | CHCH₃ | | | |
| 222 | C₆H₅ | C₆H₅NH | CHCH₃ | | | |
| 223 | C₆H₅ | C₆H₅NCH₃ | CHCH₃ | | | |
| 224 | C₆H₅ | CH₃CO | CHCH₃ | | | |
| 225 | C₆H₅ | C₆H₅CO | CHCH₃ | | | |

TABLE X-continued

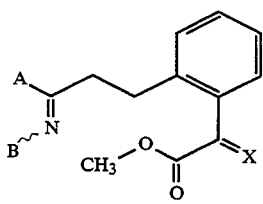

| No. | A | B | X | Isomer | m.p. (°C.) | δ (CH₂—CH₂) |
|---|---|---|---|---|---|---|
| 226 | H | CH₃ | CHC₂H₅ | | | |
| 227 | H | t-C₄H₉ | CHC₂H₅ | | | |
| 228 | H | C₆H₅ | CHC₂H₅ | | | |
| 229 | H | 2-CH₃C₆H₄ | CHC₂H₅ | | | |
| 230 | H | 4-Cyano-C₆H₄ | CHC₂H₅ | | | |
| 231 | H | 2,6-F₂—C₆H₃ | CHC₂H₅ | | | |
| 232 | CH₃ | CH₃ | CHC₂H₅ | | | |
| 233 | CH₃ | t-C₄H₉ | CHC₂H₅ | | | |
| 234 | CH₃ | C₆H₅ | CHC₂H₅ | | | |
| 235 | CH₃ | 2-CH₃C₆H₄ | CHC₂H₅ | | | |
| 236 | CH₃ | 4-Cyano-C₆H₄ | CHC₂H₅ | | | |
| 237 | CH₃ | 2,6-F₂C₆H₃ | CHC₂H₅ | | | |
| 238 | C₆H₅ | CH₃ | CHC₂H₅ | | | |
| 239 | C₆H₅ | C₆H₅ | CHC₂H₅ | | | |
| 240 | C₆H₅ | 2,6-F₂C₆H₃ | CHC₂H₅ | | | |
| 241 | H | HO | CHC₂H₅ | | | |
| 242 | H | CH₃O | CHC₂H₅ | | | |
| 243 | H | t-C₄H₉O | CHC₂H₅ | | | |
| 244 | H | H₂C=CClCH₂O | CHC₂H₅ | | | |
| 245 | H | C₆H₅CH₂O | CHC₂H₅ | | | |
| 246 | H | 2-CH₃C₆H₄CH₂O | CHC₂H₅ | | | |
| 247 | H | 2-ClC₆H₄CH₂O | CHC₂H₅ | | | |
| 248 | H | 3-CH₃OC₆H₄CH₂O | CHC₂H₅ | | | |
| 249 | H | 4-Cyano-C₆H₄CH₂O | CHC₂H₅ | | | |
| 250 | H | 2,6-F₂C₆H₃CH₂O | CHC₂H₅ | | | |
| 251 | H | 3-Pyridylmethoxy | CHC₂H₅ | | | |
| 252 | H | 5-Chlorothien-2-ylmethoxy | CHC₂H₅ | | | |
| 253 | H | CH₃CO | CHC₂H₅ | | | |
| 254 | H | C₆H₅CO | CHC₂H₅ | | | |
| 255 | CH₃ | HO | CHC₂H₅ | | | |
| 256 | CH₃ | CH₃O | CHC₂H₅ | | | |
| 257 | CH₃ | t-C₄H₉O | CHC₂H₅ | | | |
| 258 | CH₃ | H₂C=CClCH₂O | CHC₂H₅ | | | |
| 259 | CH₃ | C₆H₅CH₂O | CHC₂H₅ | | | |
| 260 | CH₃ | 2-CH₃—C₆H₄CH₂O | CHC₂H₅ | | | |
| 261 | CH₃ | 2-Cl—C₆H₄CH₂O | CHC₂H₅ | | | |
| 262 | CH₃ | 3-CH₃OC₆H₄CH₂O | CHC₂H₅ | | | |
| 263 | CH₃ | 4-Cyano-C₆H₄CH₂O | CHC₂H₅ | | | |
| 264 | CH₃ | 2,6-F₂—C₆H₃—CH₂O | CHC₂H₅ | | | |
| 265 | CH₃ | 3-Pyridylmethoxy | CHC₂H₅ | | | |
| 266 | CH₃ | 5-Chlorothien-2-ylmethoxy | CHC₂H₅ | | | |
| 267 | CH₃ | CH₃CO | CHC₂H₅ | | | |
| 268 | CH₃ | C₆H₅CO | CHC₂H₅ | | | |
| 269 | C₆H₅ | HO | CHC₂H₅ | | | |
| 270 | C₆H₅ | CH₃O | CHC₂H₅ | | | |
| 271 | C₆H₅ | H₂C=CClCH₂O | CHC₂H₅ | | | |
| 272 | C₆H₅ | C₆H₅CH₂O | CHC₂H₅ | | | |
| 273 | C₆H₅ | 2,6-F₂—C₆H₃CH₂O | CHC₂H₅ | | | |
| 274 | C₆H₅ | CH₃O | CHC₂H₅ | | | |
| 275 | H | CH₃NH | CHC₂H₅ | | | |
| 276 | H | (CH₃)₂N | CHC₂H₅ | | | |
| 277 | H | C₆H₅NH | CHC₂H₅ | | | |
| 278 | H | 2-Cl—C₆H₄NH | CHC₂H₅ | | | |
| 279 | H | C₆H₅NCH₃ | CHC₂H₅ | | | |
| 280 | H | C₆H₅CH₂NH | CHC₂H₅ | | | |
| 281 | H | 2-Cl—C₆H₄CH₂NH | CHC₂H₅ | | | |
| 282 | H | C₆H₅CH₂NCH₃ | CHC₂H₅ | | | |
| 283 | H | CH₃CO | CHC₂H₅ | | | |
| 284 | H | C₆H₅CO | CHC₂H₅ | | | |
| 285 | CH₃ | CH₃NH | CHC₂H₅ | | | |
| 286 | CH₃ | (CH₃)₂N | CHC₂H₅ | | | |
| 287 | CH₃ | C₆H₅NH | CHC₂H₅ | | | |
| 288 | CH₃ | 2-ClC₆H₄NH | CHC₂H₅ | | | |
| 289 | CH₃ | C₆H₅NCH₃ | CHC₂H₅ | | | |
| 290 | CH₃ | C₆H₅CH₂NH | CHC₂H₅ | | | |
| 291 | CH₃ | 2-Cl—C₆H₄CH₂NH | CHC₂H₅ | | | |
| 292 | CH₃ | C₆H₅CH₂NCH₃ | CHC₂H₅ | | | |

TABLE X-continued

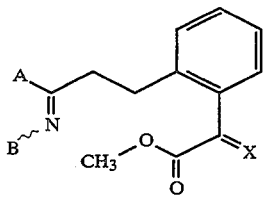

| No. | A | B | X | Isomer | m.p. (°C.) | δ (C$\underline{H}_2$—C$\underline{H}_2$) |
|-----|---|---|---|--------|------------|-----|
| 293 | CH$_3$ | CH$_3$CO | CHC$_2$H$_5$ | | | |
| 294 | CH$_3$ | C$_6$H$_5$CO | CHC$_2$H$_5$ | | | |
| 295 | C$_6$H$_5$ | CH$_3$NH | CHC$_2$H$_5$ | | | |
| 296 | C$_6$H$_5$ | (CH$_3$)$_2$N | CHC$_2$H$_5$ | | | |
| 297 | C$_6$H$_5$ | C$_6$H$_5$NH | CHC$_2$H$_5$ | | | |
| 298 | C$_6$H$_5$ | C$_6$H$_5$NCH$_3$ | CHC$_2$H$_5$ | | | |
| 299 | C$_6$H$_5$ | CH$_3$CO | CHC$_2$H$_5$ | | | |
| 300 | C$_6$H$_5$ | C$_6$H$_5$CO | CHC$_2$H$_5$ | | | |

TABLE XI

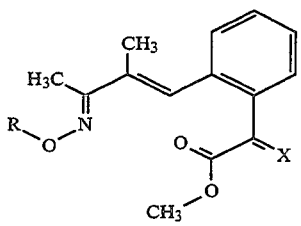

| No. | R | X | Isomer | m.p. (°C.) | δ(C=C$\underline{H}$) |
|-----|---|---|--------|------------|------|
| 1 | H | CHOCH$_3$ | | | |
| 2 | CH$_3$ | CHOCH$_3$ | | | |
| 3 | C$_2$H$_5$ | CHOCH$_3$ | | | |
| 4 | i-C$_3$H$_7$ | CHOCH$_3$ | | | |
| 5 | t-C$_4$H$_9$ | CHOCH$_3$ | a | oil | 6.65 |
| 6 | Allyl | CHOCH$_3$ | | | |
| 7 | 2-Chloroallyl | CHOCH$_3$ | | | |
| 8 | 2-Methylallyl | CHOCH$_3$ | | | |
| 9 | Benzyl | CHOCH$_3$ | | | |
| 10 | 2-Methoxybenzyl | CHOCH$_3$ | | | |
| 11 | 3-Trifluoromethylbenzyl | CHOCH$_3$ | | | |
| 12 | 4-Methylbenzyl | CHOCH$_3$ | | | |
| 13 | 3,5-Dichlorobenzyl | CHOCH$_3$ | | | |
| 14 | (2-Pyridyl)-methyl | CHOCH$_3$ | | | |
| 15 | 5-Chlorothien-2-ylmethyl | CHOCH$_3$ | | | |
| 16 | H | NOCH$_3$ | | | |
| 17 | CH$_3$ | NOCH$_3$ | | | |
| 18 | C$_2$H$_5$ | NOCH$_3$ | | | |
| 19 | i-C$_3$H$_7$ | NOCH$_3$ | | | |
| 20 | t-C$_4$H$_9$ | NOCH$_3$ | a | oil | 6.62 |
| 21 | Allyl | NOCH$_3$ | | | |
| 22 | 2-Chloroallyl | NOCH$_3$ | | | |
| 23 | 2-Methylallyl | NOCH$_3$ | | | |
| 24 | Benzyl | NOCH$_3$ | | | |
| 25 | 2-Methoxybenzyl | NOCH$_3$ | | | |
| 26 | 3-Trifluoromethylbenzyl | NOCH$_3$ | a | oil | 6.72 |
| 27 | 4-Methylbenzyl | NOCH$_3$ | | | |
| 28 | 3,5-Dichlorobenzyl | NOCH$_3$ | | | |
| 29 | (2-Pyridyl)-methyl | NOCH$_3$ | | | |
| 30 | 5-Chlorothien-2-ylmethyl | NOCH$_3$ | | | |
| 31 | H | CHCH$_3$ | | | |
| 32 | CH$_3$ | CHCH$_3$ | | | |
| 33 | C$_2$H$_5$ | CHCH$_3$ | | | |
| 34 | i-C$_3$H$_7$ | CHCH$_3$ | | | |
| 35 | t-C$_4$H$_9$ | CHCH$_3$ | | | |
| 36 | Allyl | CHCH$_3$ | | | |
| 37 | 2-Chloroallyl | CHCH$_3$ | | | |
| 38 | 2-Methylallyl | CHCH$_3$ | | | |
| 39 | Benzyl | CHCH$_3$ | | | |
| 40 | 2-Methoxybenzyl | CHCH$_3$ | | | |
| 41 | 3-Trifluoromethylbenzyl | CHCH$_3$ | | | |
| 42 | 4-Methylbenzyl | CHCH$_3$ | | | |
| 43 | 3,5-Dichlorobenzyl | CHCH$_3$ | | | |

TABLE XI-continued

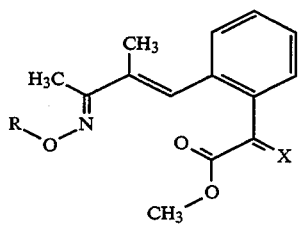

| No. | R | X | Isomer | m.p. (°C.) | δ(C=CH) |
|---|---|---|---|---|---|
| 44 | (2-Pyridyl)-methyl | CHCH$_3$ | | | |
| 45 | 5-Chlorothien-2-ylmethyl | CHCH$_3$ | | | |
| 46 | H | CHC$_2$H$_5$ | | | |
| 47 | CH$_3$ | CHC$_2$H$_5$ | | | |
| 48 | C$_2$H$_5$ | CHC$_2$H$_5$ | | | |
| 49 | i-C$_3$H$_7$ | CHC$_2$H$_5$ | | | |
| 50 | t-C$_4$H$_9$ | CHC$_2$H$_5$ | | | |
| 51 | Allyl | CHC$_2$H$_5$ | | | |
| 52 | 2-Chloroallyl | CHC$_2$H$_5$ | | | |
| 53 | 2-Methylallyl | CHC$_2$H$_5$ | | | |
| 54 | Benzyl | CHC$_2$H$_5$ | | | |
| 55 | 2-Methoxybenzyl | CHC$_2$H$_5$ | | | |
| 56 | 3-Trifluoromethylbenzyl | CHC$_2$H$_5$ | | | |
| 57 | 4-Methylbenzyl | CHC$_2$H$_5$ | | | |
| 58 | 3,5-Dichlorobenzyl | CHC$_2$H$_5$ | | | |
| 59 | (2-Pyridyl)-methyl | CHC$_2$H$_5$ | | | |
| 60 | 5-Chlorothien-2-ylmethyl | CHC$_2$H$_5$ | | | |

The novel compounds are suitable as fungicides.

The fungicidal compounds I, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are as follows:

I. A solution of 90 parts by weight of compound no. 2 and 10 parts by weight of N-methyl-α-pyrrolidone, which is suitable for application in the form of very fine drops.

II. A mixture of 20 parts by weight of compound no. 1/110, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 6/22, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 6/27, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hamer-milled mixture of 80 parts by weight of compound no. 6/72, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 6/77 and 97 parts by weight of particulate kaolin. The dust contains 3 wt % of the active ingredient.

VII. An intimate mixture of 30 parts by weight of compound no. 6/78, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 6/83, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 6/85, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi, or the seed, plants or materials threatened by fungus attack, or the soil with a fungicidally effective amount of the active ingredients.

Application is effected before or after infection of the materials, plants or seed by the fungi.

The compounds I are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), e.g., against *Paecilomyces variotii*.

The fungicidal agents generally contain from 0.1 to 95, and preferably from 0.5 to 90, wt % of active ingredient.

The application rates depend on the type of effect desired, and range from 0.02 to 3 kg of active ingredient per hectare.

When the active ingredients are used for treating seed, rates of 0.001 to 50, and preferably from 0.01 to 10, g per kg of seed are generally required.

When the agents according to the invention are used as fungicides, they may be present together with other active ingredients such as herbicides, insecticides, growth regulators, other fungicides, or fertilizers.

When the agents according to the invention are mixed with other fungicides, the spectrum of fungicidal action is frequently increased.

The active ingredient used for comparison purposes was methyl 2-(2-methylphenyl)-2-methoxyacrylate (A)- disclosed in EP 178 826.

USE EXAMPLES

Use Example 1

Action on wheat mildew

Leaves of pot-grown wheat seedlings of the "Frühgold" variety were sprayed with aqueous liquors containing (dry basis) 80% of active ingredient and 20% of emulsifier, and dusted, 24 hours after the sprayed-on layer had dried, with spores of wheat mildew (*Erysiphe graminis* var. *tritici*). The plants were then set up in the greenhouse at from 20° to 22° C. and a relative humidity of from 75 to 80%. The extent of mildew spread was assessed after 7 days.

The results show that active ingredients 2 from Table 1 (1/2), 1/110, 6/22, 6/27, 6/72, 6/77, 6/78, 6/83, 6/85, 6/89, 6/90, 7/36, 7/41a, 7/41s, 7/43, 7/60, 7/106, 7/107, 7/111, 7/112, 7/113, 7/116, 7/130 and 7/133, when applied as spray liquors containing the active ingredients in amounts of 250 ppm, have a better fungicidal action (90%) than prior art comparative compound A (50%).

Use Example 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 1/2, 1/12, 1/88, 1(115, 2/57, 3/55, 6/22, 6/27, 6/72, 6/77, 6/78, 6/83, 6/85, 6/89, 6/90, 6/97, 7/36, 7/41a, 7/41s, 7/43, 7/60, 7/106, 7/112, 7/113, 7/116, 7/130, 7/133, 8/70 and 9/50, when applied as spray liquors containing 250 ppm of active ingredient, have a better fungicidal action (90%) than prior art comparative agent A (0%).

We claim:

1. A compound of the formula I

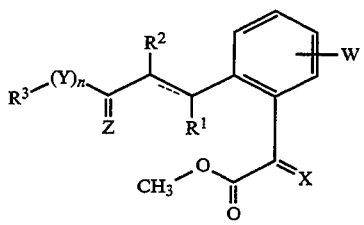

where n is 0 or 1,

W is hydrogen, halogen, unsubstituted or substituted $C_1$-$C_4$-alkyl or unsubstituted or substituted $C_1$-$C_4$-alkoxy, X is $CHOCH_3$, $NOCH_3$, $CHCH_3$ or $CHC_2H_5$, Y is oxygen, sulfur or $NR^4$, —O—$NR^4$—, —$NR^4$—O— or —$NR^4$—$NR^5$—, Z is oxygen, $NR^6$, $NOR^7$ or $N$—$NR^8R^9$ or, where n=1, sulfur, $R^1$ is hydrogen or unsubstituted or substituted $C_1$-$C_4$-alkyl, $R^2$ is independent of $R^1$ and is hydrogen unsubstituted or substituted $C_1$-$C_4$-alkyl, unsubstituted or substituted $C_3$-$C_6$-cycloalkyl, unsubstituted or substituted aryl, $C_1$-$C_4$-perfluoroalkyl or CO—V $R^3$ is hydrogen, unsubstituted or substituted $C_1$-$C_4$-alkyl, unsubstituted or substituted $C_2$-$C_4$-alkenyl, unsubstituted or substituted $C_3$-$C_6$-cycloalkyl, unsubstituted or substituted or fused aryl, unsubstituted or substituted aryl-$C_1$-$C_4$-alkyl, or unsubstituted or substituted aryl-$C_2$-$C_4$-alkenyl or, where n=0, cyano, $C_1$-$C_4$-perfluoroalkyl or unsubstituted or substituted $C_2$-$C_4$-alkynyl or, where n=1, and Y is oxygen, unsubstituted or substituted trialkylsilyl, $R^4$ and $R^5$ are independent of one another and are each hydrogen, unsubstituted or substituted $C_1$-$C_4$-alkyl or unsubstituted or substituted $C_3$-$C_6$-cycloalkyl, $R^6$ is unsubstituted or substituted $C_1$-$C_4$-alkyl, or unsubstituted or substituted or fused aryl, $R^7$ and $R^8$ are each hydrogen, unsubstituted or substituted $C_1$-$C_4$-alkyl, unsubstituted or substituted $C_2$-$C_4$-alkenyl, unsubstituted or substituted $C_2$-$C_4$-alkynyl, unsubstituted or substituted $C_3$-$C_6$-cycloalkyl, unsubstituted or substituted or fused aryl, unsubstituted or substituted aryl-$C_1$-$C_4$-alkyl, or $COR^{10}$, $R^9$ has the same meanings as $R^4$ and is independent of $R^8$, $R^{10}$ is unsubstituted or substituted $C_1$-$C_4$-alkyl, unsubstituted or substituted $C_3$-$C_6$-cycloalkyl, or unsubstituted or substituted aryl, V is unsubstituted or substituted $C_1$-$C_4$-alkyl, unsubstituted or substituted aryl, hydroxyl, unsubstituted or substituted $C_1$-$C_4$-alkoxy, unsubstituted or substituted allyloxy, unsubstituted or substituted benzyloxy or unsubstituted or substituted trialkylsilyloxy and ---- is a single bond or a double bond.

2. A compound as claimed in claim 1, wherein X is $CHOCH_3$.

3. A compound as claimed in claim 1, wherein X is $NOCH_3$.

4. A compound as claimed in claim 1, wherein X is $CHCH_3$ or $CHC_2H_5$.

5. A compound as claimed in claim 1, wherein the bond between the carbon atoms substituted by $R^1$ and $R^2$ is a single bond.

6. A compound as claimed in claim 1, wherein the bond between the carbon atoms substituted by $R^1$ and $R^2$ is a double bond.

7. A compound of the formula I as claimed in claim 1, wherein n is 0 and $R^3$—$(Y)_n$—C=Z is

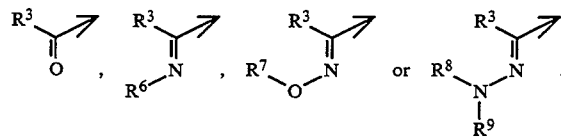

8. A compound of the formula I as claimed in claim 1, wherein n is 1 and $R^3$—$(Y)_n$—C=Z is

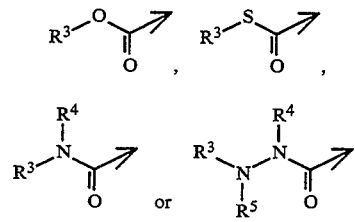

9. A compound of the formula II

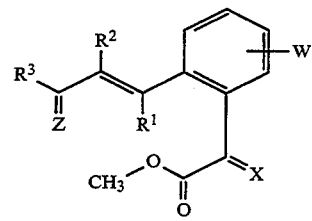

where

W is hydrogen, chlorine, methyl or methoxy,

X is $CHOCH_3$, $NOCH_3$, $CHCH_3$, or $CHC_2H_5$,

Z is oxygen, $NR^6$, $NOR^7$ or $N$—$NR^8R^9$, $R^1$ and $R^2$ are independent of one another and are each hydrogen or $C_1$-$C_4$-alkyl, $R^3$ is hydrogen, unsubstituted or substituted $C_1$-$C_4$-alkyl, unsubstituted or substituted $C_2$-$C_4$-alkenyl, unsubstituted or substituted $C_2$-$C_4$-alkynyl, unsubstituted or substituted $C_3$-$C_6$-cycloalkyl, unsubstituted or substituted or fused aryl, unsubstituted or substituted aryl-$C_1$-$C_4$-alkyl, or unsubstituted or substituted aryl-$C_2$-$C_4$-alkenyl $R^4$ is hydrogen, unsubstituted or substituted $C_1$-$C_4$-alkyl or unsubstituted or substituted $C_3$-$C_6$-cycloalkyl, $R^6$ is unsubstituted or substituted $C_1$-$C_4$-alkyl or unsubstituted or substituted or fused aryl, $R^7$ and $R^8$ are each hydrogen, unsubstituted or substituted $C_1$-$C_4$-alkyl, unsubstituted or substituted $C_2$-$C_4$-alkenyl, unsubstituted or substituted $C_2$-$C_4$-alkynyl, unsubstituted or substituted $C_3$-$C_6$-cycloalkyl, unsubstituted or substituted or fused aryl, unsubstituted or substituted aryl-$C_1$-$C_4$-alkyl, or $COR^{10}$, $R^9$ has the same meanings as $R^4$ and is independent of $R^8$ and $R^{10}$ is unsubstituted or substituted $C_1$-$C_4$-alkyl, unsubstituted or substituted $C_3$-$C_6$-cycloalkyl, or unsubstituted or substituted aryl.

10. A compound of the formula III

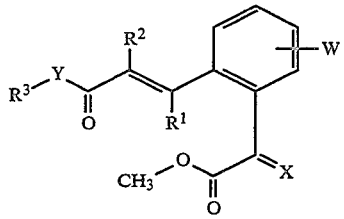

where
W is hydrogen, chlorine, methyl or methoxy,
X is $CHOCH_3$, $NOCH_3$, $CHCH_3$, or $CHC_2H_5$,
Y is oxygen, sulfur or $NR^4$
$R^1$ is hydrogen or $C_1$-$C_4$-alkyl,
$R^2$ is hydrogen, $C_1$-$C_4$-alkyl or CO—V,
$R^3$ is hydrogen, unsubstituted or substituted $C_1$-$C_4$-alkyl, unsubstituted or substituted or fused aryl, unsubstituted or substituted aryl-$C_1$-$C_4$-alkyl
$R^4$ is hydrogen, unsubstituted or substituted $C_1$-$C_4$-alkyl or unsubstituted or substituted $C_3$-$C_6$-cycloalkyl and
V is hydroxyl, $C_1$-$C_4$-alkoxy, allyloxy, trialkylsilyloxy or unsubstituted or substituted benzyloxy.

11. A compound as claimed in claim 9, wherean X is $CHOCH_3$.

12. A compound as claimed in claim 9, wherein X is $NOCH_3$.

13. A compound as claimed in claim 9, wherean X is $CHCH_3$ or $CHC_2H_5$.

14. A compound as claimed in claim 10, wherein X is $CHOCH_3$.

15. A compound as claimed in claim 10, wherein X is $NOCH_3$.

16. A compound as claimed in claim 10, wherein X is $CHCH_3$ or $CHC_2H_5$.

17. A compound of the formula IV

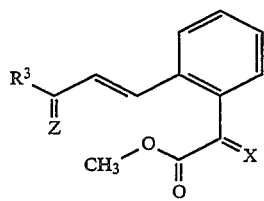

where
X is $CHOCH_3$, $NOCH_3$, $CHCH_3$, or $CHC_2H_5$,
Z is oxygen, $NOR^7$,
$R^3$ is hydrogen, unsubstituted or substituted $C_1$-$C_4$-alkyl, unsubstituted or substituted $C_2$-$C_4$-alkenyl, or unsubstituted or substituted or fused aryl,
$R^7$ is hydrogen, unsubstituted or substituted $C_1$-$C_4$-alkyl, unsubstituted or substituted $C_2$-$C_4$-alkenyl, unsubstituted or substituted aryl-$C_1$-$C_4$-alkyl, or $COR^{10}$ and
$R^{10}$ is unsubstituted or substituted $C_1$-$C_4$-alkyl, or unsubstituted or substituted aryl.

18. A compound of the formula V

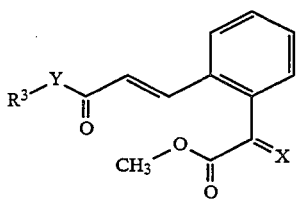

where
X is $CHOCH_3$, $NOCH_3$, $CHCH_3$, or $CHC_2H_5$,
Y is oxygen, $NR^4$,
$R^3$ is unsubstituted or substituted $C_1$-$C_4$-alkyl, unsubstituted or substituted or fused aryl, or unsubstituted or substituted aryl-$C_1$-$C_4$-alkyl, and
$R^4$ is hydrogen or $C_1$-$C_4$-alkyl.

19. A compound as claimed in claim 17, wherein X is $CHOCH_3$.

20. A compound as claimed in claim 17, wherein X is $NOCH_3$.

21. A compound as claimed in claim 17, wherein X is $CHCH_3$ or $CHC_2H_5$.

22. A compound as claimed in claim 18, wherein X is $CHOCH_3$.

23. A compound as claimed in claim 18, wherein X is $NOCH_3$.

24. A compound as claimed in claim 18, wherein X is $CHCH_3$ or $CHC_2H_5$.

25. A fungicide which contains an inert carrier and a fungicidal amount of the formula I

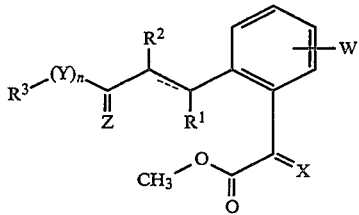

where
n is 0 or 1,

W is hydrogen, halogen, unsubstituted or substituted $C_1$–$C_4$-alkyl or unsubstituted or substituted $C_1$–$C_4$-alkoxy, X is $CHOCH_3$, $NOCH_3$, $CHCH_3$ or $CHC_2H_5$, Y is oxygen, sulfur or $NR^4$, —O—$NR^4$—, —$NR^4$—O— or —$NR^4$—$NR^5$—, Z is oxygen, $NR^6$, $NOR^7$ or N—$NR^8R^9$ or, where n=1, sulfur, $R^1$ is hydrogen or unsubstituted or substituted $C_1$–$C_4$-alkyl, $R^2$ is independent of $R^1$ and is hydrogen unsubstituted or substituted $C_1$–$C_4$-alkyl, unsubstituted or substituted $C_3$–$C_6$-cycloalkyl, unsubstituted or substituted aryl, or $C_1$–$C_4$-perfluoroalkyl or CO—V $R^3$ is hydrogen, unsubstituted or substituted $C_1$–$C_4$-alkyl, unsubstituted or substituted $C_2$–$C_4$-alkenyl, unsubstituted or substituted $C_3$–$C_6$-cycloalkyl, unsubstituted or substituted or fused aryl, unsubstituted or substituted aryl-$C_1$–$C_4$-alkyl, unsubstituted or substituted aryl-$C_2$–$C_4$-alkenyl or, where n=0, cyano, $C_1$–$C_4$-perfluoroalkyl or unsubstituted or substituted $C_2$–$C_4$-alkynyl or, where n=1, and Y is oxygen, unsubstituted or substituted trialkylsilyl, $R^4$ and $R^5$ are independent of one another and are each hydrogen, unsubstituted or substituted $C_1$–$C_4$-alkyl or unsubstituted or substituted $C_3$–$C_6$-Cycloalkyl, $R^6$ is unsubstituted or substituted $C_1$–$C_4$-alkyl, unsubstituted or substituted or fused aryl, $R^7$ and $R^8$ are each hydrogen, unsubstituted or substituted $C_1$–$C_4$-alkyl, unsubstituted or substituted $C_2$–$C_4$-alkenyl, unsubstituted or substituted $C_2$–$C_4$-alkynyl, unsubstituted or substituted $C_3$–$C_6$-cycloalkyl, unsubstituted or substituted or fused aryl, unsubstituted or substituted aryl-$C_1$–$C_4$-alkyl, or $COR^{10}$, $R^9$ has the same meanings as $R^4$ and is independent of $R^8$, $R^{10}$ is unsubstituted or substituted $C_1$–$C_4$-alkyl, unsubstituted or substituted $C_3$–$C_6$-cycloalkyl, or unsubstituted or substituted aryl, V is unsubstituted or substituted $C_1$–$C_4$-alkyl, unsubstituted or substituted aryl, hydroxyl, unsubstituted or substituted $C_1$–$C_4$-alkoxy, unsubstituted or substituted allyloxy, unsubstituted or substituted benzyloxy or unsubstituted or substituted trialkylsilyloxy.

26. A method for controlling fungi, wherein a fungicidal amount of a compound of the formula I

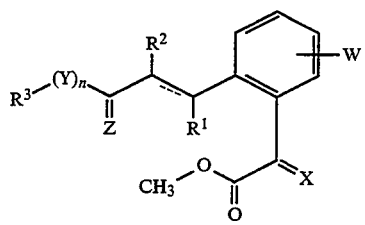

where n is 0 or 1,

W is hydrogen, halogen, unsubstituted or substituted $C_1$–$C_4$-alkyl or unsubstituted or substituted $C_1$–$C_4$-alkoxy, X is $CHOCH_3$, $NOCH_3$, $CHCH_3$ or $CHC_2H_5$, Y is oxygen, sulfur or $NR^4$, —O—$NR^4$—, —$NR^4$—O— or —$NR^4$—$NR^5$—, Z is oxygen, $NR^6$, $NOR^7$ or N—$NR^8R^9$ or, where n=1, sulfur, $R^1$ is hydrogen or unsubstituted or substituted $C_1$–$C_4$-alkyl, $R^2$ is independent of $R^1$ and is hydrogen unsubstituted or substituted $C_1$–$C_4$-alkyl, unsubstituted or substituted $C_3$–$C_6$-cycloalkyl, unsubstituted or substituted aryl, $C_1$–$C_4$-perfluoroalkyl or CO—V $R^3$ is hydrogen, unsubstituted or substituted $C_1$–$C_4$-alkyl, unsubstituted or substituted $C_2$–$C_4$-alkenyl, unsubstituted or substituted $C_3$–$C_6$-cycloalkyl, unsubstituted or substituted or fused aryl, unsubstituted or substituted aryl-$C_1$–$C_4$-alkyl, unsubstituted or substituted aryl-$C_2$–$C_4$-alkenyl or, where n=0, cyano, $C_1$–$C_4$-perfluoroalkyl or unsubstituted or substituted $C_2$–$C_4$-alkynyl or, where n=1, and Y is oxygen, unsubstituted or substituted trialkylsilyl, $R^4$ and $R^5$ are independent of one another and are each hydrogen, unsubstituted or substituted $C_1$–$C_4$-alkyl or unsubstituted or substituted $C_3$–$C_6$-cycloalkyl, $R^6$ is unsubstituted or substituted $C_1$–$C_4$-alkyl, or unsubstituted or substituted or fused aryl, $R^7$ and $R^8$ are each hydrogen, unsubstituted or substituted $C_1$–$C_4$-alkyl, unsubstituted or substituted $C_1$–$C_4$-alkenyl, unsubstituted or substituted $C_2$–$C_4$-alkynyl, unsubstituted or substituted $C_3$–$C_6$-cycloalkyl, unsubstituted or substituted or fused aryl, unsubstituted or substituted aryl-$C_1$–$C_4$-alkyl, or $COR^{10}$, $R^9$ has the same meanings as $R^4$ and is independent of $R^8$, $R^{10}$ is unsubstituted or substituted $C_1$–$C_4$-alkyl, unsubstituted or substituted $C_3$–$C_6$-cycloalkyl, or unsubstituted or substituted aryl, V is unsubstituted or substituted $C_1$–$C_4$-alkyl, unsubstituted or substituted aryl, hydroxyl, unsubstituted or substituted $C_1$–$C_4$-alkoxy, unsubstituted or substituted allyloxy, unsubstituted or substituted benzyloxy or unsubstituted or substituted trialkylsilyloxy is allowed to act on the fungi or plants, seeds or materials threatened by fungal attack or on the soil.

* * * * *